(12) United States Patent
Laby et al.

(10) Patent No.: US 10,758,714 B2
(45) Date of Patent: Sep. 1, 2020

(54) FLUID DRIVE SYSTEM FOR CATHETER ARTICULATION AND OTHER USES

(71) Applicant: Project Moray, Inc., Belmont, CA (US)

(72) Inventors: Keith Phillip Laby, Oakland, CA (US); Mark D. Barrish, Belmont, CA (US)

(73) Assignee: Project Moray, Inc., Belmont, CA (US)

( * ) Notice: Subject to any disclaimer, the term of this patent is extended or adjusted under 35 U.S.C. 154(b) by 533 days.

(21) Appl. No.: 15/080,979

(22) Filed: Mar. 25, 2016

(65) Prior Publication Data

US 2017/0021132 A1    Jan. 26, 2017

Related U.S. Application Data

(60) Provisional application No. 62/139,430, filed on Mar. 27, 2015, provisional application No. 62/175,095, (Continued)

(51) Int. Cl.
  *A61M 25/10*     (2013.01)
  *A61M 25/01*     (2006.01)
  (Continued)

(52) U.S. Cl.
  CPC ......... *A61M 25/1011* (2013.01); *A61B 34/20* (2016.02); *A61M 25/005* (2013.01);
  (Continued)

(58) Field of Classification Search
  CPC ............ A61M 25/1011; A61M 25/005; A61M 25/0155; A61M 25/1025; A61M 25/1034;
  (Continued)

(56) References Cited

U.S. PATENT DOCUMENTS 3,284,964 A    11/1966    Saito
3,459,221 A     8/1969    Axelrod
(Continued)

FOREIGN PATENT DOCUMENTS

JP    5293787 A2    11/1993
JP    2012075595 A2    4/2012
(Continued)

OTHER PUBLICATIONS

Biswal et al., "Development of an Active Catheter Mechanism using IPMC for in vivo Inspection", Journal of Mechatronics and Automation vol. 1, No. 1, http://www.academia.edu/10757534/Development_of_an_Active_Catheter_Mechanism_using_IPMC_for_in_vivo_Inspection, 2014.
(Continued)

*Primary Examiner* — Kevin C Sirmons
*Assistant Examiner* — Tezita Z Watts
(74) *Attorney, Agent, or Firm* — Kilpatrick Townsend & Stockton LLP

(57) ABSTRACT

Fluid control devices, systems, and methods are useful for articulating catheters and other elongate flexible structures. A modular manifold architecture includes plate-mounted valves to facilitate fluid communication along a plurality of fluid channels included in one or more multi-lumen shafts for articulating actuators comprising balloons within a balloon array, with the balloons often mounted on two or more extruded multi-lumen shafts. Valve/plate modules can be assembled in an array, and a proximal interface of the shaft(s) may have ports for accessing the balloon channels distributed along an axis of the interface. By aligning and engaging the proximal interface with a receptacle that traverses the plates of the manifold assembly, the ports can be quickly and easily sealed to associated channels of the various valve/plate modules using a quick-disconnect fitting.

17 Claims, 38 Drawing Sheets

Related U.S. Application Data filed on Jun. 12, 2015, provisional application No. 62/248,573, filed on Oct. 30, 2015, provisional application No. 62/263,231, filed on Dec. 4, 2015, provisional application No. 62/296,409, filed on Feb. 17, 2016.

(51) Int. Cl.

| | | |
|---|---|---|
| *A61M 25/00* | (2006.01) | |
| *A61B 34/20* | (2016.01) | |
| A61B 34/30 | (2016.01) | |
| A61B 17/00 | (2006.01) | |
| A61B 18/00 | (2006.01) | |

(52) U.S. Cl.
CPC .... *A61M 25/0155* (2013.01); *A61M 25/1025* (2013.01); *A61M 25/1034* (2013.01); *A61M 25/1036* (2013.01); *A61B 2017/00318* (2013.01); *A61B 2017/00557* (2013.01); *A61B 2018/00577* (2013.01); *A61B 2034/301* (2016.02); *A61M 2025/0166* (2013.01)

(58) Field of Classification Search
CPC ......... A61M 25/1036; A61B 2034/301; A61B 2017/00557; A61B 34/20
See application file for complete search history.

(56) References Cited

U.S. PATENT DOCUMENTS

| | | | |
|---|---|---|---|
| 3,523,547 A | 8/1970 | Hatch, Jr. et al. | |
| 3,915,194 A | 10/1975 | Friedrich | |
| 3,934,605 A | 1/1976 | Legris | |
| 4,082,324 A | 4/1978 | Obrecht | |
| 4,230,143 A | 10/1980 | Dettmann et al. | |
| 4,494,417 A | 1/1985 | Larson et al. | |
| 4,762,130 A | 8/1988 | Fogarty et al. | |
| 4,784,042 A | 11/1988 | Paynter | |
| 4,794,912 A | 1/1989 | Lia | |
| 4,838,859 A | 6/1989 | Strassmann | |
| 4,875,897 A | 10/1989 | Lee | |
| 4,893,613 A | 1/1990 | Hake | |
| 4,900,218 A | 2/1990 | Sutherland | |
| 4,983,165 A | 1/1991 | Loiterman | |
| 5,018,506 A | 5/1991 | Danna et al. | |
| 5,304,132 A | 4/1994 | Jang | |
| 5,308,356 A * | 5/1994 | Blackshear, Jr. ........................... A61M 25/1002 604/101.01 | |
| 5,337,733 A | 8/1994 | Bauerfeind et al. | |
| 5,469,756 A | 11/1995 | Feiten | |
| 5,476,100 A | 12/1995 | Galel | |
| 5,501,667 A | 3/1996 | Verduin, Jr. | |
| 5,529,088 A | 6/1996 | Asou | |
| 5,619,993 A | 4/1997 | Lee | |
| 6,066,125 A | 5/2000 | Webster et al. | |
| 6,146,339 A | 11/2000 | Biagtan et al. | |
| 6,178,872 B1 | 1/2001 | Schulz | |
| 6,503,194 B2 | 1/2003 | Pauker | |
| 6,527,739 B1 | 3/2003 | Bigus et al. | |
| 6,648,879 B2* | 11/2003 | Joye ........................ A61B 18/02 128/898 | |
| 6,811,550 B2* | 11/2004 | Holland ................. A61B 18/02 606/21 | |
| 6,875,170 B2 | 4/2005 | Francois et al. | |
| 6,928,313 B2 | 8/2005 | Peterson | |
| 6,951,226 B2 | 10/2005 | Eriksson et al. | |
| 7,060,062 B2 | 6/2006 | Joye et al. | |
| 7,373,955 B2 | 5/2008 | Steinberg | |
| 7,422,579 B2* | 9/2008 | Wahr ............... A61B 17/12045 604/509 | |
| 7,570,981 B2 | 8/2009 | Peterson | |
| 7,578,787 B2 | 8/2009 | Boese et al. | |
| 7,780,723 B2 | 8/2010 | Taylor | |
| 7,824,391 B2 | 11/2010 | Gesswein | |
| 7,850,683 B2 | 12/2010 | Elkins et al. | |
| 7,879,004 B2 | 2/2011 | Seibel et al. | |
| 7,957,790 B2 | 6/2011 | Kleen | |
| 7,963,911 B2 | 6/2011 | Turliuc | |
| 8,125,755 B2 | 2/2012 | Garcia et al. | |
| 8,201,473 B2 | 6/2012 | Knoll | |
| 8,372,055 B2 | 2/2013 | Thornton et al. | |
| 8,388,520 B2 | 3/2013 | Stefanchik et al. | |
| 8,398,540 B2 | 3/2013 | Hassidov et al. | |
| 8,469,059 B1 | 6/2013 | Forst | |
| 8,764,725 B2 | 7/2014 | Averbuch | |
| 8,845,523 B2 | 9/2014 | Lawrence et al. | |
| 8,863,608 B2 | 10/2014 | Fischer et al. | |
| 2002/0045929 A1 | 4/2002 | Diaz | |
| 2002/0049408 A1 | 4/2002 | Van Moorlegem et al. | |
| 2002/0058951 A1 | 5/2002 | Fiedler | |
| 2003/0069475 A1 | 4/2003 | Banik et al. | |
| 2005/0187467 A1 | 8/2005 | Kleen | |
| 2006/0074372 A1 | 4/2006 | Haga et al. | |
| 2006/0129142 A1 | 6/2006 | Reynolds | |
| 2006/0235368 A1 | 10/2006 | Oz | |
| 2007/0060997 A1 | 3/2007 | de et al. | |
| 2007/0100235 A1 | 5/2007 | Kennedy | |
| 2007/0169761 A1 | 7/2007 | Price et al. | |
| 2007/0270686 A1 | 11/2007 | Ritter et al. | |
| 2007/0288095 A1 | 12/2007 | Wirtel et al. | |
| 2008/0091073 A1 | 4/2008 | Park | |
| 2009/0076584 A1 | 3/2009 | Mao et al. | |
| 2011/0112632 A1 | 5/2011 | Chau et al. | |
| 2011/0270126 A1 | 11/2011 | Gunday et al. | |
| 2011/0295247 A1 | 12/2011 | Schlesinger et al. | |
| 2011/0295248 A1 | 12/2011 | Wallace et al. | |
| 2012/0089047 A1 | 4/2012 | Ryba et al. | |
| 2012/0271319 A1* | 10/2012 | Bromander ............ A61B 34/37 606/130 | |
| 2012/0310227 A1 | 12/2012 | Katou | |
| 2013/0091974 A1 | 4/2013 | Riwan et al. | |
| 2013/0096377 A1 | 4/2013 | Duindam et al. | |
| 2013/0103019 A1 | 4/2013 | Joye et al. | |
| 2013/0296983 A1* | 11/2013 | Keller ..................... A61F 7/123 607/105 | |
| 2014/0046250 A1 | 2/2014 | Jain et al. | |
| 2014/0142666 A1 | 5/2014 | Phelan et al. | |
| 2014/0243688 A1 | 8/2014 | Caron et al. | |
| 2014/0276933 A1 | 9/2014 | Hart et al. | |
| 2015/0265807 A1 | 9/2015 | Park et al. | |
| 2016/0279388 A1 | 9/2016 | Barrish et al. | |
| 2017/0021143 A1 | 1/2017 | Barrish et al. | |
| 2017/0157361 A1 | 6/2017 | Barrish et al. | |
| 2017/0157363 A1 | 6/2017 | Barrish et al. | |
| 2018/0071492 A1 | 3/2018 | Laby et al. | |
| 2018/0085559 A1 | 3/2018 | Laby et al. | |
| 2018/0200483 A1 | 7/2018 | Laby et al. | |

FOREIGN PATENT DOCUMENTS

| | | |
|---|---|---|
| WO | 2007053625 | 5/2007 |
| WO | 2012019156 A1 | 2/2012 |
| WO | 2014128507 | 8/2014 |
| WO | 2017096388 | 6/2017 |

OTHER PUBLICATIONS

Veeramani, "A transformative tool for minimally invasive procedures: design, modeling and real-time control of a polycrystalline shape memory alloy actuated robotic catheter", 2009.

Haga et al., "Active Bending Catheter and Endoscope Using Shape Memory Alloy Actuators", Available online at www.intechopen.com, Shape Memory Alloys, 2010, 21 pages.

Weber et al., "Side-Selective Atrial Transseptal Laser Puncture", The Journal of Innovations in Cardiac Rhythm Management, vol. 4, Available online at http://www.innovationsincrm.com/cardiac-rhythm-management/2013/december/524-side-selective-atrial-transseptal-laser-puncture, Dec. 2013, pp. 1481-1485.

(56) References Cited

OTHER PUBLICATIONS

3-D printing of electrically conductive materials literature review, Appropedia: The sustainability wiki, By Michigan Tech's Open Sustainability Technology Lab., 9 pages.
Accelerometer, Gyro and IMU Buying Guide, https://www.sparkfun.com/pages/accel_gyro_guide, 10 pages.
Arsalan et al., Comparison of Current Costs and Reimbursement for Transcatheter and Surgical Aortic Valve Replacement, J Am Coll Cardiol., vol. 67, Issue 13, ACC.i2 Interventional Cardiology, http://content.onlinejacc.org/article.aspx?articleid=2508037, Apr. 5, 2016, 2 pages.
Atzori et al., Indoor navigation system using image and sensor data processing on a smartphone, Optimization of Electrical and Electronic Equipment (OPTIM), 2012 13th International Conference on, https://www.researchgate.net/publication/261267019_Indoor_navigation_system_using_image_and_sensor_data_processing_on_a_smartphone, May 24-26, 2012, pp. 1158-1163.
Au et al., Microvalves and Micropumps for BioMEMS, Micromachines, vol. 2, ISSN 2072-666X www.mdpi.com/journal/micromachines, 2011, pp. 179-220.
Backer et al., Percutaneous Transcatheter Mitral Valve Replacement, Circulation: Cardiovascular Interventions http://circinterventions.ahajournals.org/content/7/3/400.full, 2014, pp. 400-409.
Bar-Cohen, Worldwide ElectroActive Polymers, EAP (Artificial Muscles) Newsletter, vol. 16, Issue 1, (The 31th issue), http://eap.jpl.nasa.gov, Jun. 2014, pp. 1-18.
BBC News, Nanotube yarns twist like muscles, http://www.bbc.co.uk/news/science-environment-15287185, Oct. 14, 2011, 8 pages.
Beahm et al., Catheter Bonding Technology Overview, www.beahmdesigns.com, Apr. 2012, 4 pages.
Bolling, Can We Predict Mitral Valve Repair Rates by Individual Surgeons' Mitral Volume?, Tex Heart Inst J., vol. 38, Issue 6, 8th Current Trends in Aortic and Cardiothoracic Surgery, http://www.ncbi.nlm.nih.gov/pmc/articles/PMC3233323/, 2011, pp. 703-704.
Buntz, Forget IoT: The Internet of Moving Things Is Where It Is At, Qmed, http://www.qmed.com/mpmn/medtechpulse/forget-iot-internet-moving-things-where-it, Dec. 10, 2014, 3 pages.
Buntz, Graphene Breakthrough Could Be a Boon to Flexible Electronics, Electronic Components, Qmed, http://www.qmed.com/mpmn/medtechpulse/graphene-breakthrough-could-be-boon-flexible-electronics?cid=nl.qmed02, Nov. 14, 2013, 1 page.
Buntz, How Tiny Artificial Muscles Could Be Huge Energy Savers, Motion Control, QMED http://www.qmed.com/mpmn/medtechpulse/how-tiny-artificial-muscles-could-be-huge-energy-savers?cid=nl.qmed02.20150223, Feb. 20, 2015, 3 pages.
Buntz, Using a T-Shirt Printer to Make Medical Circuits, QMED, Electronic Components, http://www.qmed.com/mpmn/medtechpulse/using-t-shirt-printer-make-medical-circuits, Nov. 17, 2014, 3 pages.
Catherine et al., Comparative review of endoscopic devices articulations technologies developed for minimally invasive medical procedures, Applied Bionics and Biomechanics, vol. 8, 2011, pp. 151-171.
Chakraborty et al., MEMS Micro-Valve for Space Applications, Sensors and Actuators A: Physical, vol. 83, Issue 1-3, 2000, pp. 188-193.
Chandgadkar, An Indoor Navigation System for Smartphones, http://www.doc.ic.ac.uk/teaching/distinguished-projects/2013/a.chandgadkar.pdf, Jun. 18, 2013, 80 pages.
Chang et al., Electrostatically-Actuated Reconfigurable Elastomer Microfluidics, http://people.eecs.berkeley.edu/~maharbiz/HH_paper_mpchang_0008.pdf, 4 pages.
Chen et al., High-pressure on-chip mechanical valves for thermoplastic microfluidic devices, The Royal Society of Chemistry, Lab Chip, vol. 9, 2009, pp. 3511-3516.
Clippard, New! 7 mm Electronic Valves, http://www.clippard.com/products/electronic-valve-7mm, 2 pages.
Conrad et al., Closed Loop Task Space Control of an Interleaved Continuum-Rigid Manipulator, IEEE International Conference on Robotics and Automation, http://robotics.engr.wisc.edu/cgi-bin/wikiwp/category/continuum-robotics/, 2015, 8 pages.
Corma Inc., Corrugators & Pulsating Corrugators, http://corma.com/products/corrugators-pulsating-corrugators/, 2011, 3 pages.
Coyne, Comprehensive Manufacturing of Microfluidic Diagnostic Devices, IVD, MDDI Medical Device and Diagnostic Industry, Jun. 17, 2014, 4 pages.
Creganna Tactx Medical, Deflectable & Steerable Catheter Handbook, Terminology Guide & Design Options, http://www.creganna.com/wp-content/uploads/SteeringandDeflectionTerminologyrev3.pdf, 7 pages.
Dabove et al., Inertial sensors for smartphones navigation, SpringerPlus, vol. 4, Issue 834 http://www.ncbi.nlm.nih.gov/pmc/articles/PMC4695469/, 2015, 18 pages.
D'Arcy et al., Valvular heart disease: the next cardiac epidemic, vol. 97, Issue 2, http://heart.bmj.com/content/97/2/91.extract, 2011, pp. 91-93.
De Sars et al., A practical approach to the design and control of active endoscopes, Mechatronics, vol. 20, http://www.elsevierscitech.com/pdfs/Mechatronics_DeSars.pdf, 2010, pp. 251-264.
DMQ Inc., Product Datasheet: silQflo™ Silicon Servo Valve, http://www.dmq-us.com/wp-content/uploads/2015/02/SSV-Datasheet-Rev-1.001.pdf, 2 pages.
Don et al., Novel velocity model to improve indoor localization using inertial navigation with sensors on a smart phone, http://arxiv.org/pdf/1601.03004.pdf, Jan. 12, 2016, 5 pages.
Dupont et al., Snakes, Worms and Catheters: Continuum and Serpentine Robots for Minimally Invasive Surgery, IEEE ICRA Full Day Workshop, May 3, 2010, 60 pages.
Eitel, The rise of soft robots and the actuators that drive them, http://machinedesign.com/robotics/rise-soft-robots-and-actuators-drive-them, Sep. 12, 2013, 7 pages.
Elveflow, Microfluidics and Microfluidic Devices: A Review, http://www.elveflow.com/microfluidic-tutorials/microfluidic-reviews-and-tutorials/microfluidics-and-microfluidic-device-a-review/, 2015, 10 pages.
EP Vantage Ltd., Edwards tightens transcatheter valve stranglehold, http://www.epvantage.com/Universal/View.aspx?type=Story&id=580885&isEPVantage=yes, Jun. 18, 2015, 2 pages.
Eucog Wiki, Compliant robots, http://www.eucognition.org/eucog-wiki/Compliant_robots, 2012, 5 pages.
Fedak et al., Evolving Concepts and Technologies in Mitral Valve Repair, American Heart Association, Inc., Contemporary Reviews in Cardiovascular Medicine, vol. 117, Issue 7 http://circ.ahajournals.org/content/117/7/963.full, Feb. 19, 2008, pp. 963-974.
Festo AG & Co. KG, Systematic expertise through continuous further development, Bionic Handling Assistant https://www.festo.com/net/supportportal/files/42050/brosch_fc_bha_3_0_en_lo.pdf, Apr., 2012, 6 pages.
Fite et al., A Gas-Actuated Anthropomorphic Prosthesis for Transhumeral Amputees, IEEE Transactions on Robotics, vol. 24, Issue 1, Feb. 2008, pp. 159-169.
Fornell, Transcatheter Mitral Valve Replacement Devices in Development, Diagnostic and Interventional Cardiology, http://www.dicardiology.com/article/transcatheter-mitral-valve-replacement-devices-development, Dec. 30, 2014, 5 pages.
Fu et al., Research on the axis shape of an active catheter, Int J Med Robot., vol. 4, Issue 1, Mar. 2008, pp. 69-76.
Fu et al., Steerable catheters in minimally invasive vascular surgery, Int J Med Robot., vol. 5, Issue 4, Dec. 2009, pp. 381-391.
Gionata et al., An Inertial and QR Code Landmarks-Based Navigation System for Impaired Wheelchair Users, https://www.researchgate.net/publication/261551014_An_inertial_and_QR_code_landmarks-based_navigation_system_for_impaired_wheelchair_users, May 29, 2014, pp. 205-214.
Grube, Development of a TMVR Device Challenge to Innovators, ICI meeting, Dec. 13-15, 2015, 30 pages.
Haga et al., Multi-functional Active Catheter, http://bdml.stanford.edu/twiki/pub/Haptics/DesignReferencesSummer2009/MultifunctionalActiveCatheter.pdf, pp. 147-186.
Herrmann et al., Novel Transcatheter Approaches, Heart Valve Summit, American association of Thoracic surgery, http://aats.org/multimedia/files/valve/2015/Presentations/Thursday/600-Herrmann.pdf, 2015, 26 pages.

(56) References Cited

OTHER PUBLICATIONS

Ikeuchi et al., Development of Pressure-Driven Micro Active Catheter using Membrane Micro Emboss Following Excimer Laser Ablation (MeME-X) Process, IEEE International Conference on Robotics and Automation, http://ir.nufnagoya-u.ac.jp/jspui/bitstream/2237/13924/1/ICRA09_MeMEX.pdf, May 12-17, 2009, pp. 4469-4472.
Jagadeesan, Design and Control of an Active Catheter, http://scholar.harvard.edu/jayender/activecatheter, 2 pages.
Jia et al., Online Camera-Gyroscope Auto-Calibration for Cellphones, IEEE Transactions on Image Processing http://users.ece.utexas.edu/~bevans/papers/2015/autocalibration/autocalibrationIEEETransImageProcPaperDraft.pdf, 2013, 11 pages.
John Muir Health, U.S. Aortic Stenosis Disease Prevalence & Treatment Statistics, Facts and Figures, https://www.johnmuirhealth.com/services/cardiovascular-services/intervention/transcatheter-aortic-valve-replacement/facts-and-figures.html, 2016, 3 pages.
Johnson, Modeling of Frictional Gas Flow in a Piezoelectrically Actuated High-Pressure Microvalve for Flowrate Control, Dec. 16, 2005, 197 pages.
Jung et al., A Modeling Approach for Continuum Robotic Manipulators: Effects of Nonlinear Internal Device Friction, IEEE/RSJ International Conference on Intelligent Robots and Systems, Sep. 25-30, 2011, pp. 5139-5146.
Kasahara et al., Surface Modification of Polyethylene terephthalate (PET) by 172-nm Excimer lamp, Technical paper, 2012, pp. 47-54.
Kato et al., An Inchworm Type In-pipe Mobile Microrobot Driven by Three Gas-liquid Phase-change Actuators, Proceedings of the Annual Meeting—American Society for Precision Engineering, 2003, pp. 295-298.
Kim et al., Materials for Multifunctional Balloon Catheters With Capabilities in Cardiac Electrophysiological Mapping and Ablation Therapy, Nat Mater., vol. 10, Issue 4 http://www.ncbi.nlm.nih.gov/pmc/articles/PMC3132573/, Apr. 2011, pp. 316-323.
Kirby et al., Microfluidic routing of aqueous and organic flows at high pressures: fabrication and characterization of integrated polymer microvalve elements, The Royal Society of Chemistry, Lab Chip, vol. 5, 2005, pp. 184-190.
Korane, Robot imitates an elephant's trunk, http://machinedesign.com/robotics/robot-imitates-elephant-s-trunk, Sep. 13, 2010, 5 pages.
Labsmith Inc., uProcess™ System, Microfluidic Automation, http://www.labsmith.com/products/LabSmith_uProcess_Brochure.pdf?_ga=1.142274551.472763250.1458083262., 2015, 6 pages.
Langelaar et al., Modeling of a Shape Memory Alloy Active Catheter, 45th AIAA/ASME/ASCE/AHS/ASC Structures, Structural Dynamics & Materials Conference, American Institute of Aeronautics and Astronautics http://citeseerx.ist.psu.edu/viewdoc/download?doi=10.1.1.125.1080&rep=rep1&type=pdf, Apr. 19-22, 2004, 16 pages.
Lee et al. Fabrication, Characterization, and Computational Modeling of a Piezoelectrically Actuated Microvalve for Liquid Flow Control, Journal of Microelectromechanical Systems, vol. 15, Issue 3, IEEE, Jun. 2006, pp. 686-696.
Levy, Tiny Ultrasound Camera Images Blood Vessel Interior in 3-D, Medical Imaging, QMED,http://www.qmed.com/mpmn/medtechpulse/tiny-ultrasound-camera-images-blood-vessel-interior-3-d?cid=nl.qmed02, Mar. 3, 2014, 5 pages.
Maglione et al., Ultra-High-Pressure Balloon Angioplasty for Treatment of Resistant Stenoses Within or Adjacent to Previously Implanted Pulmonary Arterial Stents, Circulation: Cardiovascular Interventions. http://circinterventions.ahajournals.org/content/2/1/52.full, 2009, pp. 52-58.
Malek et al., Femtosecond laser machining and lamination for large-area flexible organic microfluidic chips, European Physical Journal: Applied Physics, EDP Sciences https://hal.archives-ouvertes.fr/hal-00480155/document, Apr. 2009, 8 pages.
Mazzarese, Low-Profile Balloon Catheters are Critical to TAVR's Success, Medical Tubing Types by MDDI Staff, http://www.mddionline.com/article/low-profile-balloon-catheters-are-critical-tavr-success-10-21-2014?cid=nl.mddi01.20141023, Oct. 21, 2014, 3 pages.
MDDI, The Effect of Extrusion and Blow Molding Parameters on Angioplasty Balloon Production, Medical Plastics and Biomaterials, http://www.mddionline.com/article/effect-extrusion-and-blow-molding-parameters-angioplasty-balloon-production, May 1, 1998, 4 pages.
Medtronic, CoreValve™ System, 2014, 61 pages.
Messenger, A Comprehensive Guide to the U.S. TAVR Market: Surveying The Field, http://www.meddeviceonline.com/doc/a-comprehensive-guide-to-the-u-s-tavr-market-surveying-the-field-0001, Apr. 12, 2016, 7 pages.
Mohty et al., Valvular heart disease in elderly adults, http://www.uptodate.com/contents/valvular-heart-disease-in-elderly-adults, 2016, 6 pages.
Mount Sinai, Researchers Compare Two-Year Clinical Outcomes of Mitral Valve Replacement and Repair in Treating Severe Valve Regurgitation, Icahn School of Medicine at Mount Sinai, http://www.mountsinai.org/about-us/newsroom/press-releases/researchers-compare-twoyear-clinical-outcomes-of-mitral-valve-replacement-and-repair-, Nov. 9, 2015, 2 pages.
Mueller et al., An Overview of Mems-Based Micropropulsion Developments at JPL, Acta Astronautica, vol. 52, Issues 9-12, Selected Proceedings of the 3rd IAA International Symposium on Small Satellites for Earth Observation, May-Jun. 2003, 15 pages.
Mueller et al., Design and Fabrication of MEMS-Based Micropropulsion Devices at JPL, Proceedings of SPIE vol. 4558, 2001, pp. 57-71.
Muller et al., Remote control catheter navigation: options for guidance under MRI, Journal of Cardiovascular Magnetic Resonance, vol. 14, Issue 33, http://www.jcmr-online.com/content/14/1/33, 2012, pp. 1-9.
Newmarker, How Lasers Are Changing MedTech, Lasers, QMED, http://www.qmed.com/mpmn/medtechpulse/how-lasers-are-changing-medtech?cid=nl.qmed02, Jan. 14, 2014, 3 pages.
Newmarker, How Scotch Tape is Driving Diagnostics Breakthroughs, Medical Plastics, QMED, http://www.qmed.com/mpmn/medtechpulse/how-scotch-tape-driving-diagnostics-breakthroughs?cid=nl.qmed02.20141002, Oct. 1, 2014, 3 pages.
Nölker et al., Differences in Tissue Injury and Ablation Outcomes in Atrial Fibrillation Patients—Manual versus Robotic Catheters, Journal of Atrial Fibrillation, Department of Cardiology, Heart and Diabetes Center, vol. 6, Issue 2, Aug.-Sep. 2013, pp. 82-88.
Oh et al., A review of microvalves, Topical Review, Journal of Micromechanics and Microengineering, vol. 16, 2006, pp. R13-R39.
Ono et al., Development of a Cylinder Type Gas-Liquid Phase-Change Actuator, 2 pages.
Parmar, FDA Approves St. Jude Medical's Force-Sensing Ablation Catheters for AF, Regulatory and Compliance, MDDI Medical Device and Diagnostic Industry, http://www.mddionline.com/article/fda-approves-st-jude-medicals-force-sensing-ablation-catheters-af-102714?cid=nl.mddi01.20141028, Oct. 27, 2014, 3 pages.
Penning et al., A Combined Modal-Joint Space Control Approach for Minimally Invasive Surgical Continuum Manipulators, Advanced Robotics, vol. 28, Issue 16, Jul. 2014, 41 pages.
Penning et al., An Evaluation of Closed-Loop Control Options for Continuum Manipulators, IEEE, 2012, 6 pages.
Penning, ICRA 2012 Recap, http://robotics.engr.wisc.edu/cgi-bin/wikiwp/2012/11/icra-2012-recap/, Nov. 11, 2012, 2 pages.
Penning et al., Towards Closed Loop Control of a Continuum Robotic Manipulator for Medical Applications, IEEE, 2011, 6 pages.
Plastics, Corrugator technologies: overview and new developments, Corrugator technologies overview http://www.plastics.gl/extrusion-profile/corrugator-technologies-overview/, 2015, 8 pages.
Pollock, Bionic ants could be tomorrow's factory workers, http://www.reuters.com/article/2015/03/30/us-germany-bionic-ants-idUSKBN0MQ1WD20150330, Mar. 30, 2015, 3 pages.
Preston-Maher et al., A Technical Review of Minimally Invasive Mitral Valve Replacements, Cardiovascular Engineering and Technology, vol. 6, Issue 2, Jun. 2015, pp. 174-184.

(56) References Cited

OTHER PUBLICATIONS

Profilepipe Machinery Inc., Convoluted Tubing to an outer diameter of 65 mm, http://www.profilepipe.com/small_corrugators.html, 2015, 2 pages.
Qmed, Introducing 3-D Injection Molding, http://www.qmed.com/mpmn/gallery/image/4-introducing-3-d-injection-molding, 2014, 2 pages.
Qmed, Overcoming Engineering Challenges: Developing a Tiny Robotically Steerable Guidewire, Medtech Pulse Blog, http://www.qmed.com/mpmn/medtechpulse/overcoming-engineering-challenges-developing-tiny-robotically-steerable-guidewire?cid=nl_qmed_daily, Feb. 15, 2013, 2 pages.
Qmed, Tiny Artificial Muscles, http://www.qmed.com/mpmn/gallery/image/1-tiny-artificial-muscles, 1 page.
Qmed Staff, A Tiny Spectrometer that Costs 10 Bucks, http://www.qmed.com/mpmn/medtechpulse/tiny-spectrometer-costs-10-bucks?cid=nl.qmed02.20141216, Dec. 12, 2014, 3 pages.
Qmed Staff, How 3-D Printing Can Help Accelerate Fluidic Manifold Delivery, QMED, http://www.qmed.com/mpmn/medtechpulse/how-3-d-printing-can-help-accelerate-fluidic-manifold-delivery?cid=nl.qmed02.20150507, May 6, 2015, 3 pages.
Qmed Staff, How Micro-Location Could Boost Healthcare IoT, Electronic Components, http://www.qmed.com/mpmn/medtechpulse/how-micro-location-could-boost-healthcare-iot?cid=nl.x.qmed02.edt.aud.qmed.20160606, Jun. 3, 2016, 2 pages.
Quero et al., A Novel Pressure Balanced Microfluidic Valve, Proc. ISCAS, IEEE, 2002, pp. 1-4.
Rich et al., Costs for Mitral Valve Surgery According to STS Preoperative Risk: Implications for Transcatheter Mitral Therapies, American Association for Thoracic Surgery, http://aats.org/mitral/abstracts/2015/P165.cgi, 2016, 2 pages.
Roriz et al., Fiber Optic Intensity-Modulated Sensors: a Review in Biomechanics, Photonic Sensors, vol. 2, Issue 4, 2012, pp. 315-330.
Rossiter et al., Printing 3D dielectric elastomer actuators for soft robotics, SPIE Proceedings, vol. 7287, Apr. 6, 2009, 2 pages.
Schut, Corrugator Vacuum Forming, Plastics Technology, http://www.ptonline.com/articles/'corrugator-vacuum-forming, Jul. 2005, 4 pages.
Sensor Products Inc., The Benefits of Using Bend Sensors, www.sensorprod.com, 2 pages.
SGE, Scientific Tubing, Glass Lined Tubing (GLT™), www.sge.com, Fused Silica Tubing brochure PD-0230-Aw, 2001, 6 pages.
SGE, Tubing, SGE analytical science, 2011, 10 pages.
Shoa et al., Conducting Polymer Based Active Catheter for Minimally Invasive Interventions inside Arteries, Conf Proc IEEE Eng Med Biol Soc, http://mm.ece.ubc.ca/mediawiki/images/b/b7/PID616280.pdf, 2008, pp. 2063-2066.
Strickland, Inside an MRI, a Non-Metallic Robot Performs Prostate Surgery, http://spectrum.ieee.org/automaton/robotics/medical-robots/inside-an-mri-a-nonmetallic-robot-performs-prostate-surgery, Jul. 8, 2015, 3 pages.
Takizawa et al., Development of a Microfine Active Bending Catheter Equipped with MIF Tactile Sensors, http://www.ics.forth.gr/bioloch/internal/papers/Olympus.pdf, 1999, 7 pages.

Taramasso et al., Current challenges in interventional mitral valve treatment, J Thorac Dis., vol. 7, Issue 9 http://www.ncbi.nlm.nih.gov/pmc/articles/PMC4598533/, 2015, pp. 1536-1542.
Teleflex Incorporated, Balloons and Balloon Catheters, http://www.teleflexmedicaloem.com/diagnostic-and-interventional-catheters/balloon-catheters/, 2015, 3 pages.
Temiz et al., Lab-on-a-chip devices: How to close and plug the lab?, Microelectronic Engineering, vol. 132, 2015, pp. 156-175.
Tokai Medical Products Inc., PTA Sphere-Curve, http://www.tokaimedpro.co.jp/en/products/2009/000056.html, 2 pages.
Tung et al., Laser-Machined Shape Memory Alloy Actuators for Active Catheters, Mechatronics, IEEE/ASME Transactions on, vol. 12, Issue 4, Aug. 2007, pp. 439-446.
Van Oosten et al., Printed artificial cilia from liquid-crystal network actuators modularly driven by light, Nature Materials, vol. 8, http://www.nature.com/nmat/journal/v8/n8/full/nmat2487.html, 2009, pp. 677-682.
Vascular Solutions, Peripheral Dilatation Catheter Peripheral Dilatation System, PolarCath™ over-the-wire. www.vasc.com, pp. 1-12.
Walters, Gas-flow Calculations: Don't Choke, Applied Flow Technology, Chemical Engineering http://www.aft.com/documents/AFT-CE-Gasflow-Reprint.pdf, Jan. 2000, 8 pages.
Wasserman, Edwards and Medtronic turn up TAVR competition with positive study data, http://www.fiercemedicaldevices.com/story/edwards-and-medtronic-turn-tavr-competition-positive-study-data/2015-03-16, Mar. 16, 2015, 3 pages.
Webb et al., Transcatheter aortic valve implantation: The evolution of prostheses, delivery systems and approaches, Archives of Cardiovascular Disease, vol. 105, 2012, pp. 153-159.
Weber et al., Side-selective Atrial Transseptal Laser Puncture, The Journal of Innovations in Cardiac Rhythm Management, vol. 4 http://www.innovationsincrm.com/cardiac-rhythm-management/2013/december/524-side-selective-atrial-transseptal-laser-puncture, Dec. 2013, pp. 1481-1485.
Wirtl et al., White paper Piezo technology in pneumatic valves, Festo AG & Co. KG, 2014, pp. 1-9.
Wood, Early Results for Transcatheter Mitral Valve Replacement Reveal Complications and Challenges for the Long Road Ahead, http://www.tctmd.com/show.aspx?id=133937, Feb. 22, 2016, 6 pages.
Wutzler et al., Robotic Ablation of Atrial Fibrillation, Department of Cardiology, Vis. Exp. (99), e52560, http://www.jove.com/video/52560/robotic-ablation-of-atrial-fibrillation, 2015, 14 pages.
Yang et al., Leak-Tight Piezoelectric Microvalve for High-Pressure Gas Micropropulsion, Journal of Microelectromechanical Systems, vol. 13, Issue 5, IEEE, http://web.stevens.edu/ses/documents/fileadmin/documents/pdf/JMEMS_hp_valve.pdf, Oct. 2004, pp. 799-807.
Yarbasi et al., On the Design of a Continuum Robot with Extendable Balloons, Department of Mechanical Engineering, 2015, 1 page.
You et al., A doubly cross-linked nano-adhesive for the reliable sealing of flexible microfluidic devices, Lab Chip., vol. 13, Issue 7, http://www.ncbi.nlm.nih.gov/pubmed/23381132, Apr. 2013, pp. 1266-1272.

\* cited by examiner

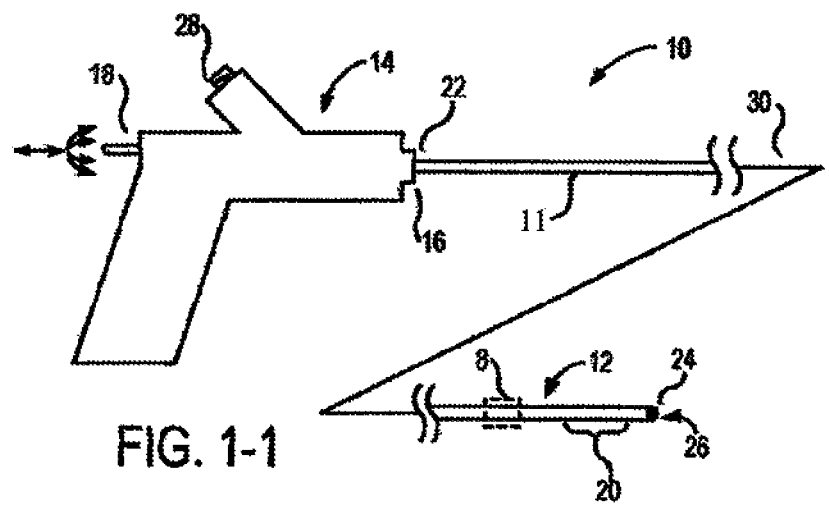
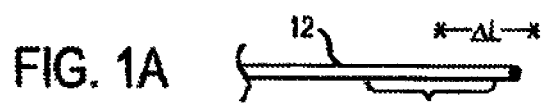
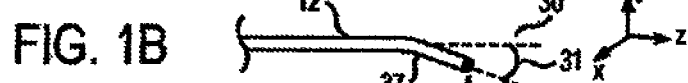
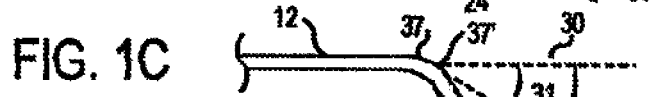
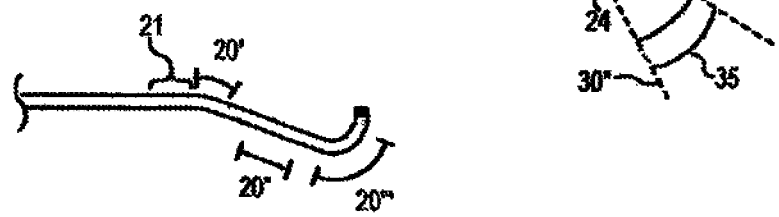

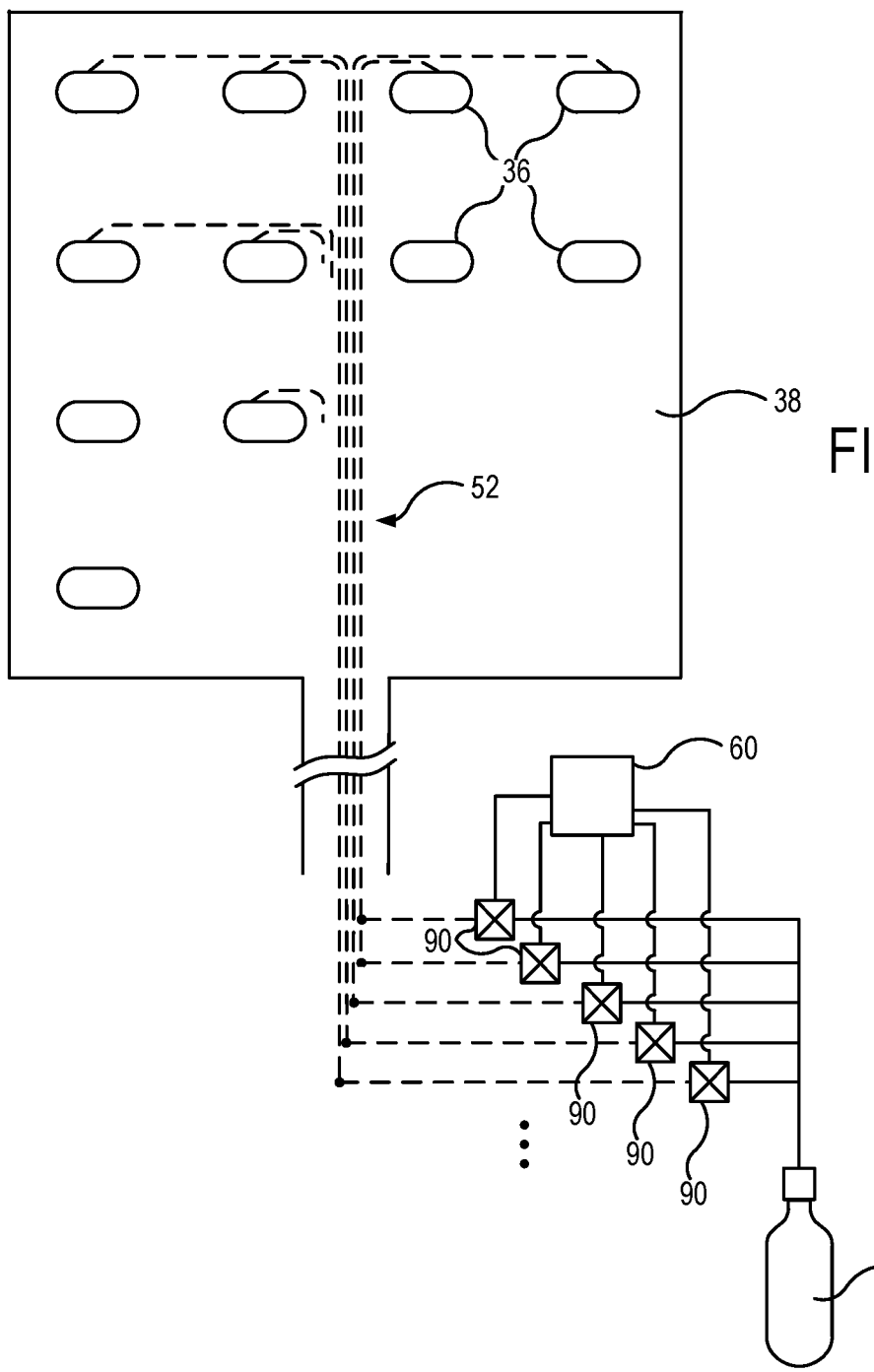

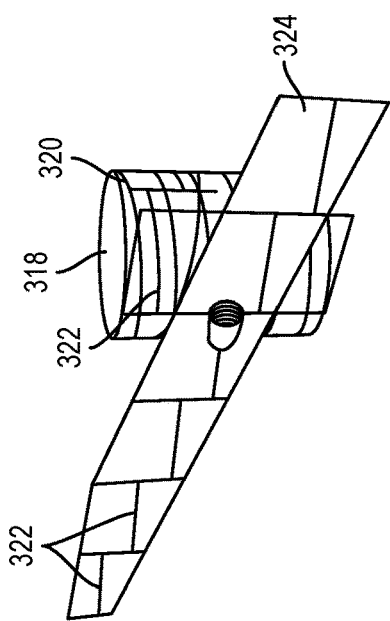
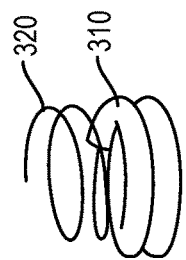
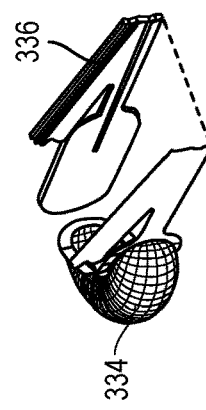
FIG. 10A
FIG. 10B
FIG. 10C
FIG. 10D

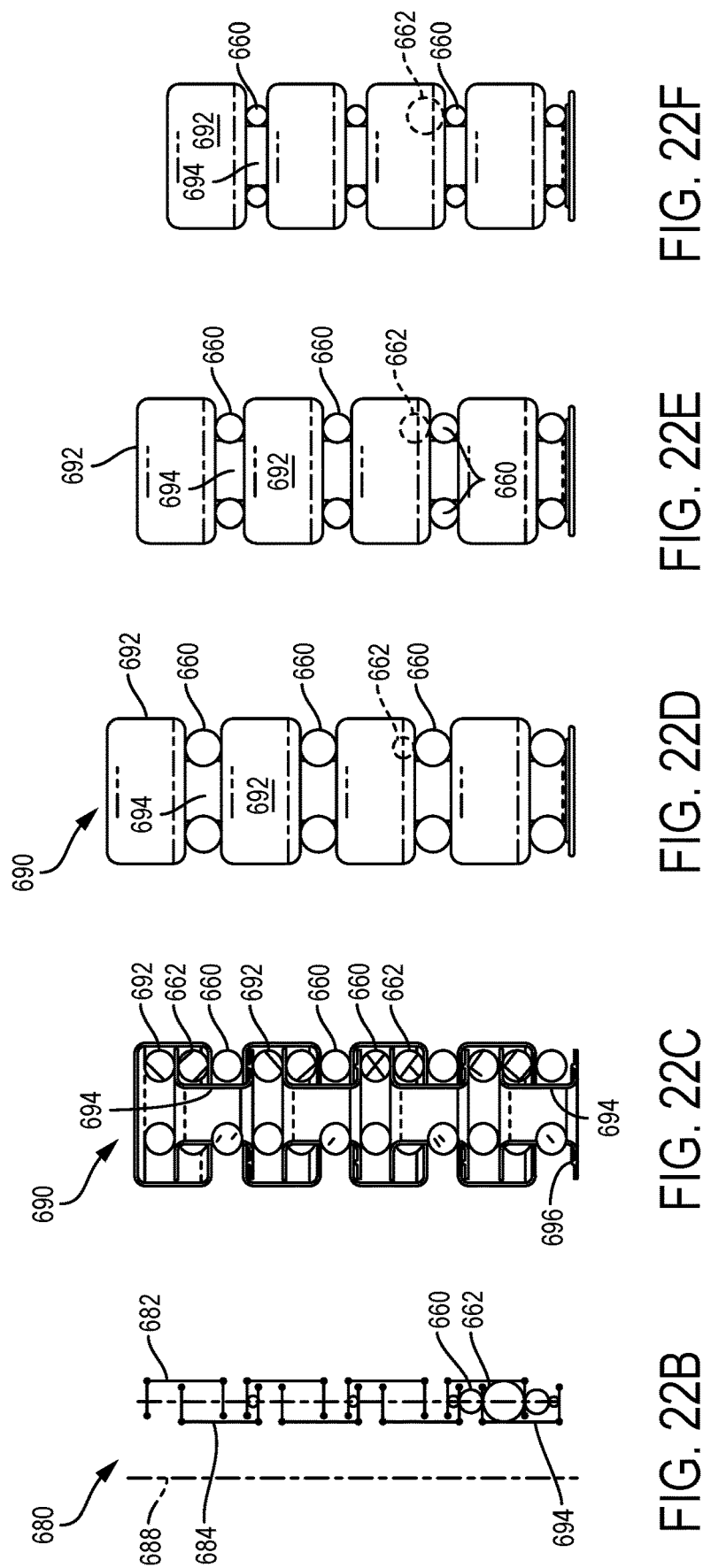

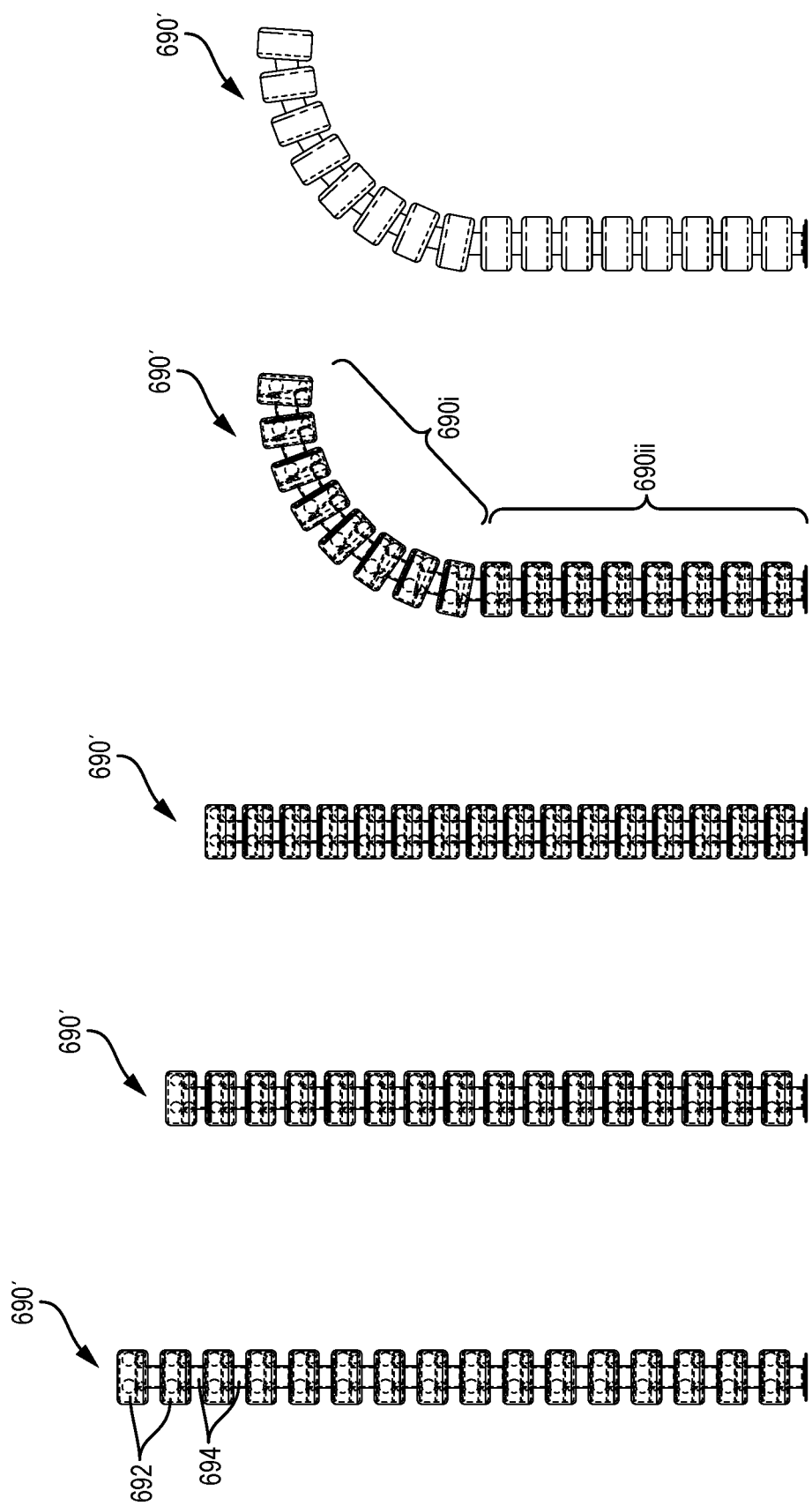

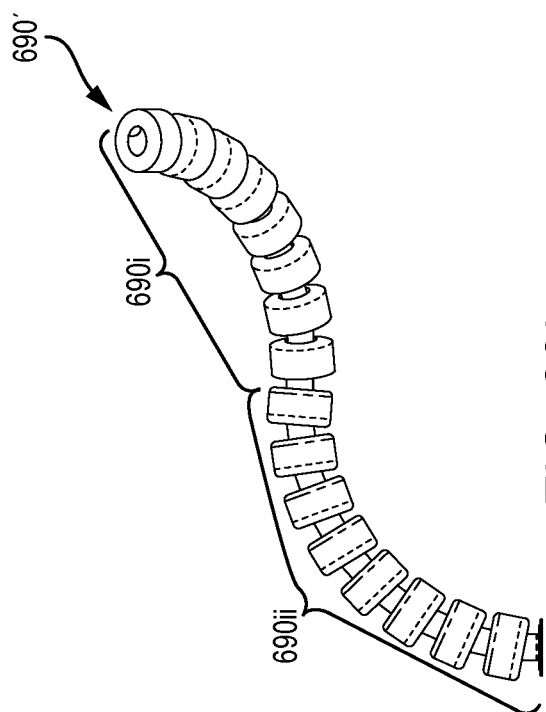
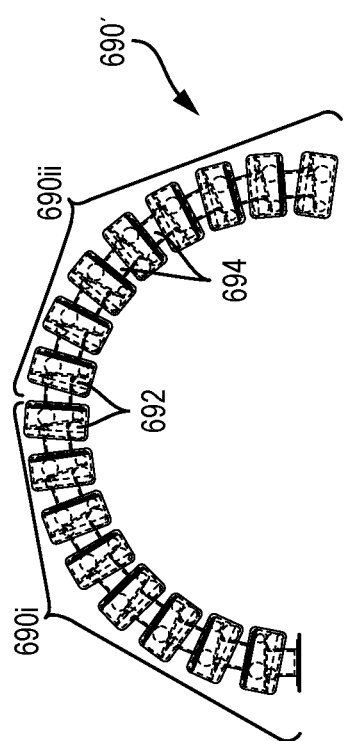
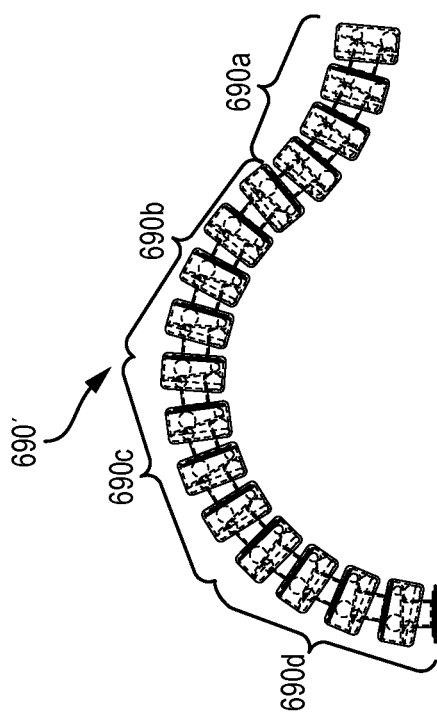
FIG. 23I
FIG. 23H
FIG. 23J

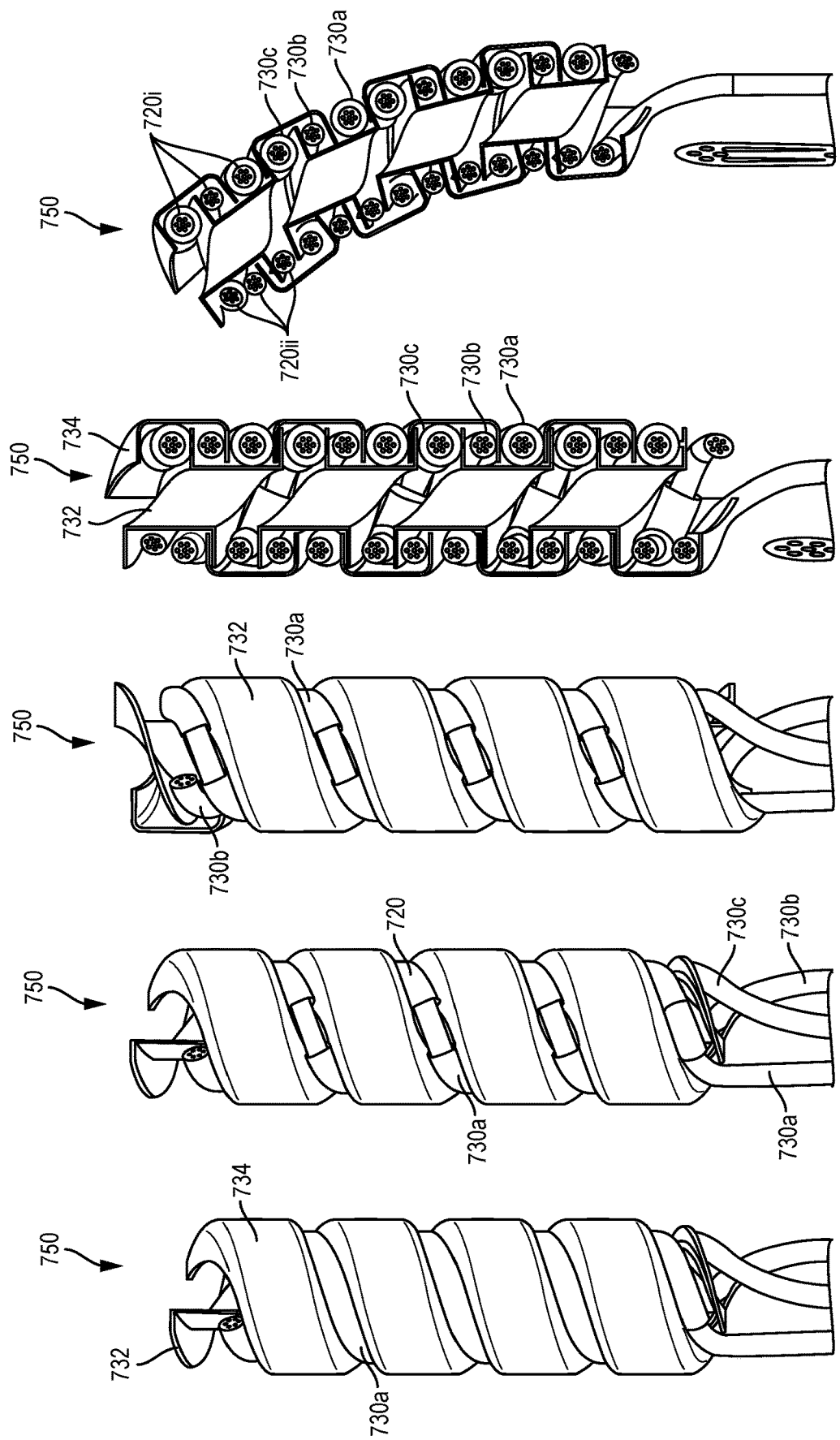

FLUID DRIVE SYSTEM FOR CATHETER ARTICULATION AND OTHER USES

CROSS REFERENCE TO RELATED APPLICATIONS

The present application claims the benefit of priority from co-assigned US Provisional Patent App. Nos. 62/139,430 filed Mar. 27, 2015, entitled "Articulation System for Catheters and Other Uses"; 62/175,095 filed Jun. 12, 2015, entitled "Selective Stiffening for Catheters and Other Uses"; 62/248,573 filed Oct. 30, 2015, entitled "Fluid Articulation for Catheters and Other Uses"; 62/263,231 filed Dec. 4, 2015, entitled "Input and Articulation System for Catheters and Other Uses"; and 62/296,409 filed Feb. 17, 2016, entitled "Local Contraction of Flexible Bodies using Balloon Expansion for Extension-Contraction Catheter Articulation and Other Uses"; the full disclosures which are incorporated herein by reference in their entirety for all purposes.

The subject matter of the present application is related to that of co-assigned U.S. patent application Ser. No. 15/081,026, filed Mar. 25, 2016, entitled "Articulation System, Devices, and Methods for Catheters and Other Uses"; and Ser. No. 15/080,949, also filed Mar. 25, 2016, entitled "Fluid-Expandable Body Articulation of Catheters and Other Flexible Structures"; the full disclosures which are also incorporated herein by reference in their entirety for all purposes.

FIELD OF THE INVENTION

In general, the present invention provides fluid handling devices, systems, and methods, often for articulating elongate flexible structures. In exemplary embodiments, the invention provides multi-channel fluid-drive systems that can be used to selectively energize actuators (ideally to selectably inflate balloons in a balloon array) so as to controllably alter the shape and/or stiffness of an elongate flexible structure. In preferred embodiments, the invention provides improved medical devices, systems, and methods, including improved articulation devices, systems, and methods for selectively bending of, altering the bend characteristics of, and/or altering the lengths of elongate flexible medical structures such as catheters, guidewires, and the like.

BACKGROUND OF THE INVENTION

Diagnosing and treating disease often involve accessing internal tissues of the human body. Once the tissues have been accessed, medical technology offers a wide range of diagnostic tools to evaluate tissues and identify lesions or disease states. Similarly, a number of therapeutic tools have been developed that can help surgeons interact with, remodel, deliver drugs to, or remove tissues associated with a disease state so as to improve the health and quality of life of the patient. Unfortunately, gaining access to and aligning tools with the appropriate internal tissues for evaluation or treatment can represent a significant challenge to the physician, can cause serious pain to the patient, and may (at least in the near term) be seriously detrimental to the patient's health.

Open surgery is often the most straightforward approach for gaining access to internal tissues. Open surgery can provide such access by incising and displacing overlying tissues so as to allow the surgeon to manually interact with the target internal tissue structures of the body. This standard approach often makes use of simple, hand-held tools such as scalpels, clamps, sutures, and the like. Open surgery remains, for many conditions, a preferred approach. Although open surgical techniques have been highly successful, they can impose significant trauma to collateral tissues, with much of that trauma being associated with gaining access to the tissues to be treated.

To help avoid the trauma associated with open surgery, a number of minimally invasive surgical access and treatment technologies have been developed. Many minimally invasive techniques involve accessing the vasculature, often through the skin of the thigh, neck, or arm. One or more elongate flexible catheter structures can then be advanced along the network of blood vessel lumens extending throughout the body and its organs. While generally limiting trauma to the patient, catheter-based endoluminal therapies are often reliant on a number of specialized catheter manipulation techniques to safely and accurately gain access to a target region, to position a particular catheter-based tool in alignment with a particular target tissue, and/or to activate or use the tool. In fact, some endoluminal techniques that are relatively simple in concept can be very challenging (or even impossible) in practice (depending on the anatomy of a particular patient and the skill of a particular physician). More specifically, advancing a flexible guidewire and/or catheter through a tortuously branched network of body lumens might be compared to pushing a rope. As the flexible elongate body advances around first one curve and then another, and through a series of branch intersections, the catheter/tissue forces, resilient energy storage (by the tissue and the elongate body), and movement interactions may become more complex and unpredictable, and control over the rotational and axial position of the distal end of a catheter can become more challenging and less precise. Hence, accurately aligning these elongate flexible devices with the desired luminal pathway and target tissues can be a significant challenge.

A variety of mechanisms can be employed to steer or variably alter deflection of a tip of a guidewire or catheter in one or more lateral directions to facilitate endoluminal and other minimally invasive techniques. Pull wires may be the most common catheter tip deflection structures and work well for many catheter systems by, for example, controllably decreasing separation between loops along one side of a helical coil, braid, or cut hypotube near the end of a catheter or wire. It is often desirable to provide positive deflection in opposed directions (generally by including opposed pull wires), and in many cases along two orthogonal lateral axes (so that three or four pull wires are included in some devices). Where additional steering capabilities are desired in a single device, still more pull wires may be included. Complex and specialized catheter systems having dozens of pull wires have been proposed and built, in some cases with each pull wire being articulated by a dedicated motor attached to the proximal end. Alternative articulation systems have also been proposed, including electrically actuated shape memory alloy structures, piezoelectric actuation, phase change actuation, and the like. As the capabilities of steerable systems increase, the range of therapies that can use these technologies should continue to expand.

Unfortunately, as articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. Hysteresis and friction of a pull-wire system may vary significantly with that sliding interaction and with different overall configurations of the bends, so that the articulation system response may be difficult to predict and control. Furthermore, more complex pull wire systems may add additional challenges. While opposed pull-wires can each be used to bend a catheter in opposite directions from a generally straight configuration, attempts to use both together—while tissues along the segment are applying unknown forces in unknown directions—may lead to widely inconsistent results. Hence, there could be benefits to providing more accurate small and precise motions, to improving the lag time, and/or to providing improved transmission of motion over known catheter pull-wire systems so as to avoid compromising the coordination, as experienced by the surgeon, between the input and output of catheters and other elongate flexible tools.

Along with catheter-based therapies, a number of additional minimally invasive surgical technologies have been developed to help treat internal tissues while avoiding at least some of the trauma associated with open surgery. Among the most impressive of these technologies is robotic surgery. Robotic surgeries often involve inserting one end of an elongate rigid shaft into a patient, and moving the other end with a computer-controlled robotic linkage so that the shaft pivots about a minimally invasive aperture. Surgical tools can be mounted on the distal ends of the shafts so that they move within the body, and the surgeon can remotely position and manipulate these tools by moving input devices with reference to an image captured by a camera from within the same workspace, thereby allowing precisely scaled micro-surgery. Alternative robotic systems have also been proposed for manipulation of the proximal end of flexible catheter bodies from outside the patient so as to position distal treatment tools. These attempts to provide automated catheter control have met with challenges, which may be in-part because of the difficulties in providing accurate control at the distal end of a flexible elongate body using pull-wires extending along bending body lumens. Still further alternative catheter control systems apply large magnetic fields using coils outside the patient's body to direct catheters inside the heart of the patient, and more recent proposals seek to combine magnetic and robotic catheter control techniques. While the potential improvements to control surgical accuracy make all of these efforts alluring, the capital equipment costs and overall burden to the healthcare system of these large, specialized systems is a concern.

In light of the above, it would be beneficial to provide new and improved devices, system, and methods for driving elongate flexible structures. It would also be beneficial to provide improved medical devices, systems, and methods, particularly those that involve the use of elongate flexible bodies such as catheters, guidewires, and other flexible minimally invasive surgical tools. It would be desirable to take advantage of recent advances in microfluidic technologies and fabrication techniques to provide fluid drive systems having a relatively large number of fluid channels that could be used to control catheters and other elongate flexible structures within a patient, or that could otherwise be used to accurately control flow to and/or within a multi-lumenal shaft, ideally without having to resort to large, expensive systems having large numbers of motors or the like.

BRIEF SUMMARY OF THE INVENTION

The present invention generally provides fluid control devices, systems, and methods that are particularly useful for articulating catheters and other elongate flexible structures. In exemplary embodiments the invention provides a manifold architecture that facilitates separate computer-controlled fluid-actuated articulation of a plurality of actuators disposed along the flexible body. The exemplary manifold includes fluid supply channels that are distributed across several regions of a manifold body, the manifold body optionally comprising modular plates with plate-mounted valves to facilitate fluid communication through a plurality of fluid transmission channels included in one or more multi-lumen shafts of the articulated flexible body. The actuators preferably comprise balloons within a balloon array, and will often be mounted on one, two, or more extruded multi-lumen shafts. Valve/plate modules can be assembled in an array or stack, and a proximal interface of the shaft(s) may have ports for accessing the transmission channels, with the ports being distributed along an axis of the proximal interface. By aligning and engaging the proximal interface with a receptacle that traverses the plates or regions of the manifold assembly, the ports can be quickly and easily sealed to associated channels of the various valve/plate modules using a quick-disconnect fitting.

In a first aspect, the invention provides an articulation system comprising an articulated structure including an elongate flexible body having a proximal end and a distal end with an axis therebetween. A proximal interface adjacent the proximal end has a plurality of ports, a plurality of actuators distal of the ports, and a plurality of lumens extending along the flexible body. Each lumen provides fluid communication between an associated port and an associated actuator. The system also includes a manifold having a manifold body. The manifold body has a proximal orientation and a distal orientation with a manifold axis therebetween. The manifold body has a plurality of regions distributed along the manifold axis, each region having a fluid supply channel. The manifold also has a receptacle that traverses the regions, and the receptacle can removably receive the proximal interface with each port in sealed fluid communication with an associated fluid supply channel such that, during use, fluid transmitted from the fluid supply channels can actuate the actuators and induce movement of the distal end.

In another aspect, the invention provides a manifold for use with an articulated structure. The articulated structure includes an elongate flexible body extending between a proximal interface and a distal end with a plurality of ports along the proximal interface, a plurality of actuators distal of the ports, and a plurality of lumens providing fluid communication between the ports and the actuators. The manifold comprises a manifold body with a proximal end and a distal end and a manifold axis therebetween. The manifold body has plurality of regions distributed along the manifold axis, each region having a fluid channel. A receptacle traverses the regions. The receptacle can removably receive the proximal portion of the elongate body with each port in sealed fluid communication with an associated fluid channel such that, during use, fluid transmitted from the fluid channels can induce movement of the distal end.

In another aspect, the invention provides an articulated structure for use with a manifold having a manifold body. The manifold has a plurality of regions, each region having a fluid channel. The manifold also has a receptacle traversing the regions so that the fluid channels are distributed along the receptacle. The articulated structure comprises an elongate flexible body having a proximal end and a distal end and defining an axis therebetween. The body has a proximal interface adjacent the proximal end and a plurality of ports along the proximal interface, a plurality of actuators distal of the ports and along the flexible body, and a plurality of lumens. Each lumen provides fluid communication between an associated port and an associated actuator. The proximal interface of the elongate body is removably receivable by the receptacle with each port in sealed fluid communication with an associated supply channel such that, during use, fluid transmitted from the fluid supply channels can induce movement of the distal end.

In yet another aspect, the invention provides an interface for use in an articulation system. The articulation system includes an articulated structure with an elongate flexible body having a proximal shaft portion and a distal end and defining an axis therebetween. A plurality of lumens and a plurality of actuators are disposed along the flexible body. The proximal shaft portion has a plurality of axially distributed shaft ports, and each lumen provides fluid communication between an associated shaft port and an associated actuator. The articulation system further includes a manifold having a manifold body with a plurality of fluid supply channels. The interface comprises an interface body having a proximal end and a distal end, the interface body comprising a plurality of deformable seals and a plurality of rigid structures including a proximal rigid structure and a distal rigid structure. The rigid structures are axially interleaved with the seals, and passages extend axially within the rigid structures and seals. The passages are aligned to form a receptacle extending between the distal rigid structure and the proximal rigid structure. An axial compression member couples the proximal rigid structure with the distal rigid structure so as to maintain an axial compressive force therebetween. The passage of the interface body is sized and configured to receive the proximal shaft of the elongate body when the compression member does not apply the axial compressive force. The axial compressive force between the proximal and distal rigid structures can induce protrusion of the seals radially inwardly along the receptacle so as to sealingly engage the proximal shaft portion between the shaft ports such that, during use, fluid transmitted from the fluid supply channels can actuate the actuators and induce movement of the distal end.

In many of the devices and systems described herein, the articulated structure comprises a catheter. Other articulated structures that can be used include guidewires, endoscopes and endoscope support devices, boroscopes, industrial manipulators or manipulator portions (such as grippers or the like), prostheses, and the like. The actuators of the articulated structures will often include a plurality of balloons, with the balloons often being included in a balloon array that is distributed axially and circumferentially about an elongate body of the articulated structure. In exemplary embodiments, the number of independent fluid channels that are coupled through the interface/receptacle pairing will be between 5 and 60, there typically being from 6 to 50 channels, preferably from 12 to 42 articulation fluid channels, and ideally from 12 to 24 articulation fluid channels included within 1-4 extruded multi-lumen shafts or other multi-lumen substrate structures.

In general, the manifold body may comprise a plurality of plates. Each plate will typically have opposed major surfaces, with the regions of the manifold body being bordered by the plate surfaces. The receptacle typically traverses the plates. Note that the plates of the manifold may optionally be included in modular valve/plate units, so that an assembly of the plates and valves controls and directs fluid flow. In other embodiments, the manifold may comprise a simple interface structure that can, for example, direct fluid between a more complex module assembly (having valves, pressure sensors, and the like) and one or more flexible multi-lumen shafts of the articulated body. The port-supporting proximal interface of the articulable structure optionally comprises a single rigid contiguous structure. Though the receptacle may span across several regions or plates of the manifold assembly, the receptacle of the assembled manifold often comprises a contiguous feature such that alignment of the proximal interface with the receptacle registers all the channels with all the ports. Note that there may be additional couplers or connectors that are flexibly attached to the proximal interface (such as one or more separately positionable electrical connector, optical fiber connector, and/or separate fluid connectors(s) for therapeutic fluids (such as for irrigation, aspiration, drug delivery, or the like) or even actuation (such as for a prosthesis deployment balloon or the like). When desired, one, some, or all of these connectors may be integrated into the proximal interface and receptacle. Regardless, one or more quick-disconnect fitting (such as the type that are manually movable between a first or latched configuration and a second or detachable configuration) may be used to facilitate and maintain sealed fluid communication between the ports and associated channels, and to allow quick and easy removal and replacement of the proximal portion so as to replace the articulated structure with a different alternative articulated structure.

The proximal interface of the articulatable structure can optionally facilitate one or more additional form of communication beyond the sealed port/channel fluid coupling. For example, the proximal interface may include a radio frequency identification (RFID) label, an electrical connector, and/or an optical fiber connector. In such embodiments, the receptacle will often include an RFID reader, an electrical connector, and/or an optical fiber connector, respectively. RFID data, or electronic identification data, optical identification data, or other forms of data can be used by a processor coupled to the manifold to identify a type of the articulable structure (and optionally the specific articulable structure itself). Transmitting this identification data across such a communication link between the proximal interface and the receptacle facilitates a plug-and-play operability of the system, allowing a processor of the system to tailor fluid transmissions between the manifold and the articulable structure to the particular type of articulable structure that is in use, allowing the system to induce desired articulations without having to manually reconfigure the processor or manifold. Identification data can also help prevent unsafe and inappropriate re-use of high-pressure balloon articulation devices. Articulation state feedback may be provided using electrical interface/receptacle connectors (such as using known electromagnetic internal navigation systems) or optical interface/receptacle connectors (such as using known optical fiber Bragg grating flex sensors). Such connectors may also be used by diagnostic or therapeutic tools carried by the articulatable structure.

The proximal interface and the receptacle may take any of a variety of specific (and typically corresponding) forms. The receptacle or the proximal interface may, for example, comprise an array of posts, with the other comprising an array of indentations. The posts will typically extend along parallel axes (often from an underlying surface of the proximal interface) and be matable with the indentations (typically being on the receptacle), often so that the posts can all be inserted into the indentations with a single movement of a proximal interface body toward the receptacle. Seals around the posts can provide sealed, isolated fluid communication between the ports and the channels.

The total cross-sectional area of the posts and indentations that is exposed to the fluid(s) therein may be limited to less than two square inches, and typically being less than one square inch, most often being less than 0.1 square inches, and ideally being about 0.025 square inches or less so as to avoid excessive ejection forces. In many such post-indentation embodiments, the articulable structure can transmit the fluid flows from the manifold toward the actuators using a multi-lumen shaft. To transmit a relatively large number of independent flows, the articulable structure may have a plurality of multi-lumen shafts, such as an integer number A of multi-lumen shafts extending distally from the proximal interface, A being greater than 1 (and typically being 2 or 3). Each multi-lumen shaft can have an integer number B of lumens with associated ports and associated actuators, B also being greater than 1 (and typically being from 3 to 15, more typically being 6 to 15). The array of posts may comprise an A×B array of posts, and the post/indentation engagements may be distributed among B valve module plates of the manifold. In exemplary embodiments, each plate comprises a plurality of plate layers, and each plate has a lateral plate receptacle member that is affixed to the plate layers. The receptacle can be defined by lateral surfaces of the receptacle members.

In alternative forms of the proximal interface and receptacle, the receptacle may be defined by receptacle passages that extend entirely through some, most, or even all of the plates of the manifold. The plates may be stacked into an array (typically with the opposed major surfaces in apposition), and the receptacle passages can be axially aligned in the assembled manifold so as to facilitate inserting the proximal interface therein. In such embodiments, the proximal interface of the articulatable body may comprise a shaft having axially distributed ports. Exemplary proximal interface structures may take the form of a simple extruded polymer multi-lumen shaft, with the ports comprising lateral holes drilled into the various lumens. The multi-lumen shaft itself may be inserted into and seal against the receptacle, or there may be an intermediate interface body having a tube or shaft that facilitates the use of the manifold with different articulable structures. Regardless, the shaft can be configured and sized to be inserted into the receptacle so as to provide sealing engagement between the ports, and which can result in sealed communication between the ports and their associated fluid channels. Optionally, a compression member couples the plates of the manifold together so as to impose axial compression. Deformable seals may be disposed between the plates, and those seals may protrude radially inwardly into the receptacle so as to seal between the ports when the compression member squeezes the plates together. Alternative seal structures may protrude radially outwardly to provide sealing against a surrounding surface.

The manifold bodies provided herein may optionally use of a modular manifold assembly structure having an array of interchangeable plate modules. The plate modules include valves and one or more plate layers. The plate layers of each module define a proximal major surface of the module and a distal major surface of the plate module. The major surfaces of adjacent plate modules may be in direct apposition with direct plate material-plate material contact (optionally with the engaging plate surfaces fused together), but may more typically have deformable sealing material (such as O-rings, formed in place gasket material, laser cut gaskets, 3D printed sealing material, or the like) or with a flexible film (such as a flex circuit substrate and/or a deformable sealing member adhesively bonded to one of the adjoining plates) between the plate structures. In some embodiments (particularly those in which the plates are laterally supported by a receptacle member) there may be gaps between some or all of the plates in the array. Regardless, an axial spacing between the ports of the proximal interface can correspond to a module-to-module separation between the fluid channels of the adjacent modules. Hence, alignment of the proximal interface with the receptacle can, when the axes of the interface and the receptacle are aligned, register each of the ports with an associated fluid channel (despite the channels being included on different plate modules). Alternative module body structures may comprise 3D printed structures, with valves, sensors and the like optionally being integrally printed or affixed to the manifold body.

The plate modules will optionally be disposed between a proximal end cap of the manifold and a distal end cap of the manifold. The plate modules may each include a plurality of plate module layers, with the fluid channels typically being disposed between the layers (such as by molding or laser micromachining an open channel into the surface of one layer and sealing the channel by bonding another layer over the open channel). In some embodiments, inflation passages extend through some, most, or even all of the modular plate layers, and these inflation passages can be aligned in the stacked plates of the modular manifold assembly to form a continuous inflation fluid header (with the ends of the inflation header typically being sealed by the end caps). Inflation valves can be disposed along inflation channels between the inflation header and the receptacle so as to control a flow of pressurized inflation fluid transmitted from the header toward a particular port of the articulated structure. Optionally, deflation passages may similarly extend through some, most, or all of the plate layers and align in the modular manifold assembly to form a continuous deflation header, deflation valves being disposed along deflation channels between the deflation header and the receptacle. Alternative embodiments may simply port the deflation fluid from each plate directly to the atmosphere, foregoing the deflation header. However, use of the deflation header may be provide advantages; a deflation plenum can be in fluid communication with the deflation header, and a deflation valve can be disposed between the deflation plenum and a deflation exhaust port (for releasing deflation fluid to the atmosphere of the like). By coupling a pressure sensor to the deflation plenum, the deflation back-pressure can be monitored and/or controlled.

In most of the manifold assemblies provided herein, a plurality of pressure sensors are coupled to the channels of the plate modules. The pressure sensors are also coupled to a processor, and the processor transmits valve commands to valves of the plate modules in response to pressure signals from the pressure sensors. Preferably, most or all of the channels having an associated port in the articulated assembly will also have a pressure sensor coupled thereto so as to all the pressures of fluids passing through the ports of the interface to the monitored and controlled.

In exemplary embodiments, a pressurized canister containing inflation fluid is used in the inflation fluid source. The inflation fluid preferably comprises an inflation liquid in the canister, though the inflation liquid will often vaporize to an inflation gas for use within the actuators. The pressurized canister can be mated with a canister receptacle or socket of the manifold so as to transmit the inflation fluid toward the fluid channels, with the socket often having a pin that pierces a frangible seal of the canister. The vaporization of liquid in the canister can help maintain a constant fluid inflation pressure without having to resort to pumps or the like. An exemplary inflation fluid comprises a cryogenic fluid such as nitrous oxide, with the canister preferably containing less than 10 oz. of the inflation fluid, often from 0.125 oz. to 7½ oz., typically from 0.25 oz to 3 oz. Fluid pressures in the manifold may range up to about 55 atm. or more, with controlled pressures often being in a range from about 3 atm. to about 40, optionally being less than about 35, and in many cases being about 27 atm. or less.

The valve of the fluid control manifolds described herein may include an inflation valve disposed between the fluid source and a first balloon, and a deflation valve disposed between a second balloon and a surrounding atmosphere. The first valve can be configured to independently transmit minimum increments of 50 nl or less of the liquid, with the flowing cooling fluid often remaining liquid till it traverses a throat of the valve. The second valve can be configured to independently transmit at least 0.1 scc/s of the gas. Including such valves in the system for inflation lumen of the articulated device may facilitate independent pressure control over the balloons (or the subsets of balloons, with each subset being inflated using a common inflation lumen). For many embodiments, the minimum liquid increment may be 25 nl (or even 15 nl) or less, while the minimum gas flow may be 0.5 scc/s (or even 1 scc/s) or more. Some embodiments may employ multi-way valves that can be used to control both inflation fluid flowing into the balloon and deflation fluid exhausted from the balloon, with accuracy of control (despite the different inflation and deflation flows) being maintained by differing valve throats, by differing orifices or other flow restricting devices adjacent the valve, by proportional flow control of sufficient range, and/or by a sufficiently rapid valve response rate. In some embodiments, a pressure-controlled plenum can be disposed between the fluid source and the first and second balloon, or the liquid may otherwise vaporize to the gas before the valve so that none of the liquid transits a valves between the plenum and the balloons.

To facilitate the safe use of inflation fluids for articulation of catheters and other articulatable structures, a fluid shutoff valve may be disposed upstream of the fluid channels. Moreover, a vacuum source and a vacuum sensing system may also be included, with the actuators being disposed within a sealed chamber of the articulation structure and the vacuum source being coupleable to that chamber. The vacuum sensing system can couple the chamber to the shutoff valve so as to inhibit transmission of inflation fluid to the actuators of the articulable structure in response to deterioration of vacuum within the chamber. Advantageously, the vacuum source may comprise a simple positive displacement pump (such as a syringe pump with a latchable handle)), and electronic sensing of the vacuum can provide continuous safety monitoring. The chamber of the articulatable structure can be provided using an outer sheath around the balloon array, and optionally an inner sheath within a helical or other annular balloon array arrangement. By sealing the array proximally and distally of the balloons, the space surrounding the array can form a vacuum chamber in which the vacuum will deteriorate if any leakage of the inflation fluid out of the array, and or any leakage of blood, air, or other surrounding fluids into the chamber.

Having processor-controlled valves is an optional feature of the systems and devices described herein, and any of a range of refinements may be included to further enhance capabilities of the system. Rather than having to resort to heavy and complex motors and pumps, by using a simple fluid source (such as a pre-pressurized canister or the like) and processor controlled valves (optionally including at least 8, 16, 32, or even 64 valves), the system can control shape and/or stiffness of an elongate flexible system with large number of degrees of freedom. Where a processor is provided, a plurality of pressure sensors may couple some of the channels with the processor, the processor configured to actuate the valves so as to control pressure within the subsets of balloons. With or without processor controlled valves, another optional feature is that the articulation devices may have balloon arrays with at least 9, 18, 36, 72, or even 108 balloons. Where the articulated catheter has an outer cross-sectional diameter, the balloon array may have an axial density of at least 3, 4, 6, 8, or even 9 balloons per diameter of axial length to provide, for example, a desirable bend capability. The manifold/catheter interface may provide an axial density of at least 1, 2, 3, 4, or even 6 channels per diameter of axial length of the receptacle. Having structural features, including small profile seals between balloons and between relatively high-density, high pressure channels within the catheter/manifold quick-disconnect interface structures may significantly impact the utility of the system.

In another aspect, the invention provides an articulation system comprising an articulated structure including an elongate flexible body having a proximal end and a distal end with an axis therebetween. A proximal interface adjacent the proximal end has a plurality of ports, a plurality of actuators distal of the ports, and a plurality of lumens extending along the flexible body. Each lumen provides fluid communication between an associated port and an associated actuator. The system also includes a modular fluid supply assembly, with the assembly comprising a plurality of plates. Each plate has opposed major surfaces and a fluid supply channel. A receptacle traverses the plates, and the receptacle can removably receive the proximal interface with each port in sealed fluid communication with an associated fluid supply channel such that, during use, fluid transmitted from the fluid supply channels can actuate the actuators and induce movement of the distal end.

In another aspect, the invention provides a modular fluid supply assembly for use with an articulated structure. The articulated structure includes an elongate flexible body extending between a proximal interface and a distal end (with a plurality of ports along the proximal interface), a plurality of actuators distal of the ports, and a plurality of lumens providing fluid communication between the ports and the actuators. The modular fluid supply comprises a plurality of plates, each plate having opposed major surfaces and a fluid channel. A receptacle traverses the plates. The receptacle can removably receive the proximal portion of the elongate body with each port in sealed fluid communication with an associated fluid channel such that, during use, fluid transmitted from the fluid channels can induce movement of the distal end.

In yet another embodiment, the invention provides a fluid supply system for use with a device. The fluid supply system comprises a modular fluid manipulation assembly comprising a plurality of plate modules. Each module includes a plate having opposed major surfaces, a valve, and a fluid channel, the plates in an array having a receptacle traversing the plates. The receptacle removably receives an interface of the device so that a plurality of ports of the interface are each in sealed fluid communication with an associated fluid supply channel of the plates such that, during use, fluid transmitted from the fluid supply channels can be independently transmitted to the ports.

In a yet further embodiment, the invention provides a method for assembling a manifold or interface for use with a device. The device has an interface with a plurality of ports. The method comprises aligning a plurality of plates in an array. Each plate has opposed major surfaces, a receptacle surface portion extending between the major surfaces, and a channel coupled to the receptacle portion. The receptacle portions are affixed in alignment so that the receptacle portions form a receptacle. The receptacle is configured to removably receive the device and to provide sealed fluid communication between the channels and the ports.

In a yet further embodiment, the invention provides a method for preparing an articulation system for use. The method comprises providing an articulated structure having a proximal interface and a distal end with a flexible body therebetween. The proximal interface has a plurality of ports with associated actuators disposed along the flexible body. The proximal interface is coupled with a receptacle of a modular manipulator assembly. The manipulator assembly has a plurality of plate modules, each plate module having a plate with opposed major surfaces, a fluid channel, and a valve along the channel. The coupling of the proximal interface is performed by aligning the ports with the channels and sealing between the ports so as to facilitate independent control of fluid flow through the ports.

In another aspect, the invention provides an articulation system comprising an articulated structure including an elongate flexible body having a proximal end and a distal end with an axis therebetween. A proximal interface adjacent the proximal end has a plurality of ports, a plurality of actuators distal of the ports, and a plurality of lumens extending along the flexible body. Each lumen provides fluid communication between an associated port and an associated actuator. A manifold has a manifold body with a plurality of fluid supply channels, the manifold having a receptacle that removably receives the proximal interface of the articulated structure with each port in sealed fluid communication with an associated fluid supply channel such that, during use, fluid transmitted from the fluid supply channels can actuate the actuators and induce movement of the distal end, and the fluid can flow from the actuators back to the manifold body without mixing of the fluid of different actuators. Optionally, the fluid may comprise a liquid in the manifold, may vaporize and expand so that the fluid comprises a gas in the actuators, and the gas may flow back to the manifold.

BRIEF DESCRIPTION OF THE DRAWINGS

FIG. 1-1 schematically illustrates a catheter articulation system having a hand-held proximal housing and a catheter with a distal articulatable portion in a relaxed state.

FIGS. 1A-1C schematically illustrate a plurality of alternative articulation states of the distal portion of the catheter in the system of FIG. 1.

FIG. 2 schematically illustrates an alternative distal structure having a plurality of articulatable sub-regions or segments so as to provide a desired total number of degrees of freedom and range of movement.

FIG. 5A is a simplified schematic of an alternative balloon array and fluid control system, in which a plurality of valves coupled with the proximal end of the catheter can be used to direct fluid to any of a plurality of channels of the array and thereby selectably determine a subset of balloons to be expanded.

FIGS. 10A-10D are perspective drawings showing an exemplary flat-pattern substrate and associated balloon array generated by unwinding a helical balloon pattern, along with an exemplary bonded balloon fabrication technique.

FIGS. 18A-18C are perspective views showing an alternative modular manifold assembly having modules that each include valves, supply fluid channels, exhaust fluid channels, and passages through the plates of the modules that align in the stacked-plate assembly for use as multi-lumen shaft receptacles, fluid headers, and the like.

FIGS. 20A-22A schematically illustrate skeletons structures having frames or members with balloons mounted in opposition so as to axially extend with inflation of one subset of the balloons, and to axially contract with inflation of another subset of balloons.

FIGS. 22B and 22C are a schematic illustration of an exemplary axial expansion/contraction skeleton with axial expansion and axial contraction balloons; and a corresponding cross-section of a skeleton having an axial series of annular members or rings articulated by the axial expansion and axial contraction balloons, respectively.

FIGS. 22D-22H are illustrations of elongate flexible articulated structures having annular skeletons with three opposed sets of balloons, and show how varying inflation of the balloons can be used to axially contract some portions of the frame and axially extend other portions to bend or elongate the frame and to control a pose or shape of the frame in three dimensions.

FIGS. 23A-23J are illustrations of alternative elongate articulated flexible structures having annular skeletons and two sets of opposed balloons, and show how a plurality of independently controllable axial segments can be combined to allow control of the overall elongate structure with 6 or more degrees of freedom.

FIGS. 25A-25F illustrate exemplary elongate articulated flexible structures having helical skeleton members and three helical balloon assemblies supported in opposition along the skeleton, and also show how selective inflation of subsets of the balloons can locally axially elongate and/or contract the skeleton to bend the structure laterally and/or alter the overall length of the structure.

DETAILED DESCRIPTION OF THE INVENTION

Figure 1:
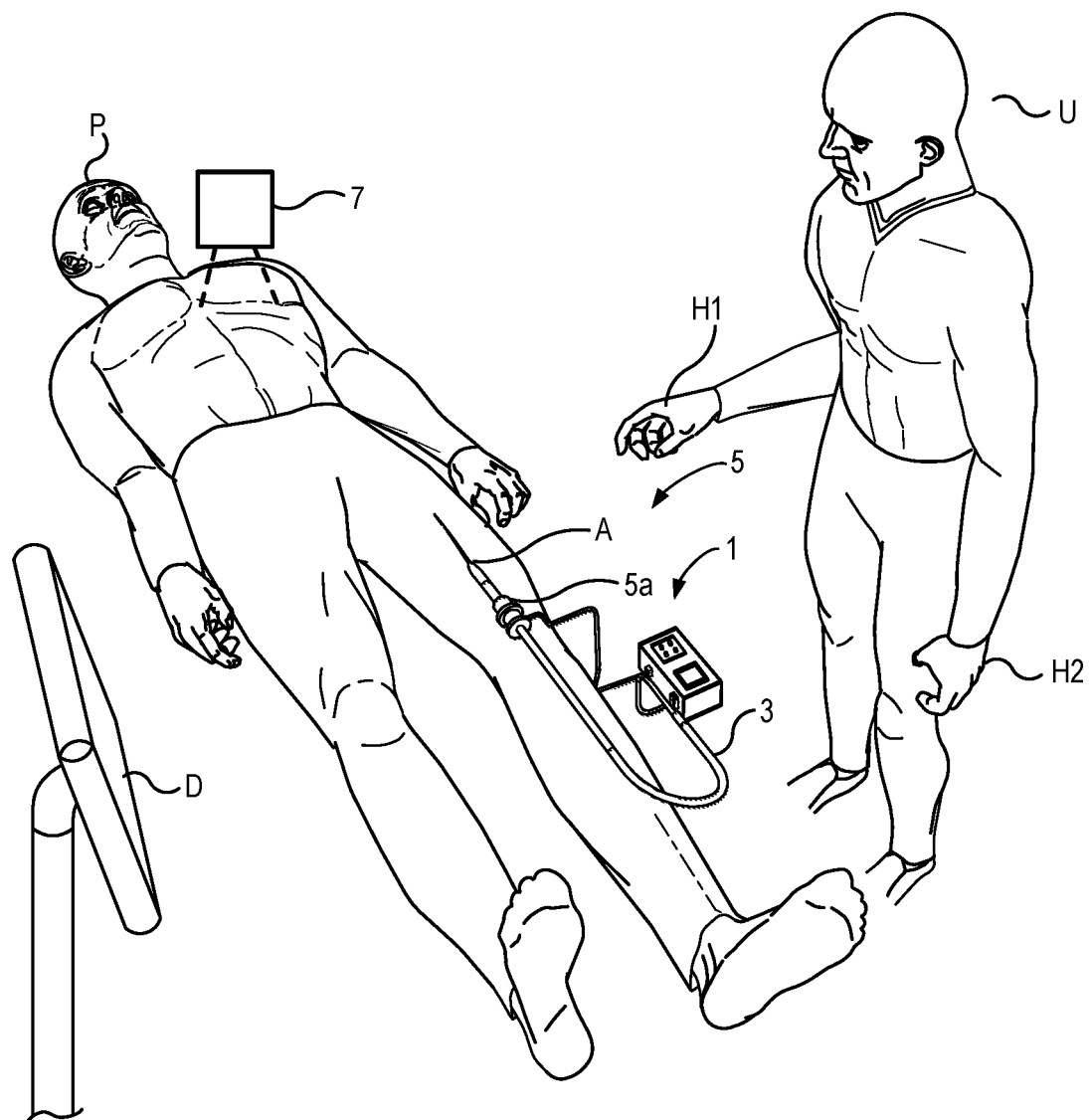
FIG. 1 is a simplified perspective view of a medical procedure in which a physician can input commands into an catheter system so that a catheter is articulated using systems and devices described herein.

The present invention generally provides fluid control devices, systems, and methods that are particularly useful for articulating catheters and other elongate flexible structures. In exemplary embodiments the invention provides a modular manifold architecture that includes plate-mounted valves to facilitate fluid communication along a plurality of fluid channels included in one or more multi-lumen shafts, often for articulating actuators of a catheter. Preferred actuators include balloons or other fluid-expandable bodies, and the modular manifold assemblies are particularly well suited for independently controlling a relatively large number of fluid pressures and/or flows. The individual plate modules may include valves that control fluid supplied to a catheter or other device, and/or fluid exhausted from the catheter or other device. A receptacle extending across a stack of such modules can receive a fluid flow interface having a large number of individual fluid coupling ports, with the total volume of the modular valve assembly, including the paired receptacle and fluid flow interface of the device often being quite small. In fact, the modular manifold will preferably be small enough to hold in a single hand, even when a controller (such as a digital processor), a pressurized fluid source (such as a canister of cryogenic fluid), and an electrical power source (such as a battery) are included. When used to transmit liquids that will vaporize to a gas that inflates a selected subset of microballoons within a microballoon array, control over the small quantities of inflation liquids may direct microfluidic quantities of inflation fluids. Microelectromechanical system (MEMS) valves and sensors may find advantageous use in these systems; fortunately, suitable microfluidic and MEMS structures are now commercially available.

Embodiments provided herein may use balloon-like structures to effect articulation of the elongate catheter or other body. The term "articulation balloon" may be used to refer to a component which expands on inflation with a fluid and is arranged so that on expansion the primary effect is to cause articulation of the elongate body. Note that this use of such a structure is contrasted with a conventional interventional balloon whose primary effect on expansion is to cause substantial radially outward expansion from the outer profile of the overall device, for example to dilate or occlude or anchor in a vessel in which the device is located. Independently, articulated medial structures described herein will often have an articulated distal portion, and an unarticulated proximal portion, which may significantly simplify initial advancement of the structure into a patient using standard catheterization techniques.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transvers to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Catheter 3 may be used by user U in different modes during a single procedure, including two or more of a manual manipulation mode, an automated and powered shape-changing mode, and a combination mode in which the user manually moves the proximal end while a computer articulates the distal portion. More specifically, at least a portion of the distal advancement of catheter 3 within the patient may be performed in a manual mode, with system user U manually manipulating the exposed proximal portion of the catheter relative to the patient using hands H1, H2. Catheter 3 may, for example, be manually advanced over a guidewire, using either over-the-wire or rapid exchange techniques. Catheter 3 may also be self-guiding during manual advancement (so that for at least a portion of the advancement of catheter 3, a distal tip of the catheter may guide manual distal advancement). Automated lateral deflection of a distal portion of the catheter may impose a desired distal steering bend prior to a manual movement, such as near a vessel bifurcation, followed by manual movement through the bifurcation. In addition to such manual movement modes, catheter system 1 may also have a 3-D automated movement mode using computer controlled articulation of at least a portion of the length of catheter 3 disposed within the body of the patient to change the shape of the catheter portion, often to advance or position the distal end of the catheter. Movement of the distal end of the catheter within the body will often be provided per real-time or near real-time movement commands input by user U, with the portion of the catheter that changes shape optionally being entirely within the patient so that the movement of the distal portion of the catheter is provided without movement of a shaft or cable extending through the access site. Still further modes of operation of system 1 may also be implemented, including concurrent manual manipulation with automated articulation, for example, with user U manually advancing the proximal shaft through access site A while computer-controlled lateral deflections and/or changes in stiffness over a distal portion of the catheter help the distal end follow a desired path or reduce resistance to the axial movement.

Referring next to FIG. 1-1 components which may be included in or used with catheter system 1 or catheter 3 (described above) can be more fully understood with reference to an alternative catheter system 10 and its catheter 11 (or other articulated structure). Catheter 11 generally includes an elongate flexible catheter body 12 and is detachably coupled to a handle 14, preferably by a quick-disconnect coupler 16. Catheter body 12 has an axis 30, and an input 18 of handle 14 can be moved by a user so as to locally alter the axial bending characteristics along catheter body 12, often for variably articulating an actuated portion 20 of the catheter body. Catheter body 12 will often have a working lumen 26 into or through which a therapeutic and/or diagnostic tool may be advanced from a proximal port 28 of handle 14. Alternative embodiments may lack a working lumen, may have one or more therapeutic or diagnostic tools incorporated into the catheter body near or along actuated portion 20, may have a sufficiently small outer profile to facilitate use of the body as a guidewire, may carry a tool or implant near actuated portion 20 or near distal end 26, or the like. In particular embodiments, catheter body 12 may support a therapeutic or diagnostic tool 8 proximal of, along the length of, and/or distal of actuated portion 20. Alternatively, a separate elongate flexible catheter body may be guided distally to a target site once catheter body 20 has been advanced (with the elongate body for such uses often taking the form and use of a guidewire or guide catheter).

The particular tool or tools included in, advanceable over, and/or introducible through the working lumen of catheter body 20 may include any of a wide range of therapeutic and/or treatment structures. Examples include cardiovascular therapy and diagnosis tools (such as angioplasty balloons, stent deployment balloons or other devices, atherectomy devices, tools for detecting, measuring, and/or characterizing plaque or other occlusions, tools for imaging or other evaluation of, and/or treatment of, the coronary or peripheral arteries, structural heart tools (including prostheses or other tools for valve procedures, for altering the morphology of the heart tissues, chambers, and appendages, and the like), tools for electrophysiology mapping or ablation tools, and the like); stimulation electrodes or electrode implantation tools (such as leads, lead implant devices, and lead deployment systems, leadless pacemakers and associated deployments systems, and the like); neurovascular therapy tools (including for accessing, diagnosis and/or treatment of hemorrhagic or ischemic strokes and other conditions, and the like); gastrointestinal and/or reproductive procedure tools (such as colonoscopic diagnoses and intervention tools, transurethral procedure tools, transesophageal procedure tools, endoscopic bariatric procedure tools, etc.); hysteroscopic and/or falloposcopic procedure tools, and the like; pulmonary procedure tools for therapies involving the airways and/or vasculature of the lungs; tools for diagnosis and/or treatment of the sinus, throat, mouth, or other cavities, and a wide variety of other endoluminal therapies and diagnoses structures. Such tools may make use of known surface or tissue volume imaging technologies (including imaging technologies such as 2-D or 3-D cameras or other imaging technologies; optical coherence tomography technologies; ultrasound technologies such as intravascular ultrasound, transesophogeal ultrasound, intracardiac ultrasound, Doppler ultrasound, or the like; magnetic resonance imaging technologies; and the like), tissue or other material removal, incising, and/or penetrating technologies (such a rotational or axial atherectomy technologies; morcellation technologies; biopsy technologies; deployable needle or microneedle technologies; thrombus capture technologies; snares; and the like), tissue dilation technologies (such as compliant or non-compliant balloons, plastically or resiliently expandable stents, reversibly expandable coils, braids or other scaffolds, and the like), tissue remodeling and/or energy delivery technologies (such as electrosurgical ablation technologies, RF electrodes, microwave antennae, cautery surfaces, cryosurgical technologies, laser energy transmitting surfaces, and the like), local agent delivery technologies (such as drug eluting stents, balloons, implants, or other bodies; contrast agent or drug injection ports; endoluminal repaving structures; and the like), implant and prosthesis deploying technologies, anastomosis technologies and technologies for applying clips or sutures, tissue grasping and manipulation technologies; and/or the like. In some embodiments, the outer surface of the articulation structure may be used to manipulate tissues directly. Non-medical embodiments may similarly have a wide range of tools or surfaces for industrial, assembly, imaging, manipulation, and other uses.

Addressing catheter body 12 of system 10 (and particularly articulation capabilities of actuated portion 20) in more detail, the catheter body generally has a proximal end 22 and a distal end 24 with axis 30 extending between the two. As can be understood with reference to FIG. 2, catheter body 12 may have a short actuated portion 20 of about 3 diameters or less, but will often have an elongate actuated portion 20 extending intermittently or continuously over several diameters of the catheter body (generally over more than 3 diameters, often over more than 10 diameters, in many cases over more than 20 diameters, and in some embodiments over more than 40 diameters). A total length of catheter body 12 (or other flexible articulated bodies employing the actuation components described herein) may be from 5 to 500 cm, more typically being from 15 to 260 cm, with the actuated portion optionally having a length of from 1 to 150 cm (more typically being 2 to 20 cm) and an outer diameter of from 0.65 mm to 5 cm (more typically being from 1 mm to 2 cm). Outer diameters of guidewire embodiments of the flexible bodies may be as small as 0.012" though many embodiments may be more than 2 Fr, with catheter and other medical embodiments optionally having outer diameters as large as 34 French or more, and with industrial robotic embodiments optionally having diameters of up to 1" or more. Exemplary catheter embodiments for structural heart therapies (such as trans-catheter aortic or mitral valve repair or implantation, left atrial appendage closure, and the like) may have actuated portions with lengths of from 3 to 30 cm, more typically being from 5 to 25 cm, and may have outer profiles of from 10 to 30 Fr, typically being from 12 to 18 Fr, and ideally being from 13 to 16 Fr. Electrophysilogy therapy catheters (including those having electrodes for sensing heart cycles and/or electrodes for ablating selected tissues of the heart) may have sizes of from about 5 to about 12 Fr, and articulated lengths of from about 3 to about 30 cm. A range of other sizes might also be implemented for these or other applications.

Referring now to FIGS. 1A, 1B, and 1C, system 10 may be configured to articulate actuated portion 20. Articulation will often allow movement continuously throughout a range of motion, though some embodiments may provide articulation in-part or in-full by selecting from among a plurality of discrete articulation states. Catheters having opposed axial extension and contraction actuators are described herein that may be particularly beneficial for providing continuous controlled and reversible movement, and can also be used to modulate the stiffness of a flexible structure. These continuous and discrete systems share many components (and some systems might employ a combination of both approaches). First addressing the use of a discrete state system, FIG. 1A, system 10 can, for example, increase an axial length of actuated portion 20 by one or more incremental changes in length $\Delta L$. An exemplary structure for implementation of a total selectable increase in length $\Delta L$ can combine a plurality of incremental increases in length $\Delta L = \Delta L_1 + \Delta L_2 + \ldots$ ), as can be understood with reference to FIG. 4D. As shown in FIGS. 1B and 1C, system 10 may also deflect distal end 24 to a first bent state having a first bend angle 31 between unarticulated axis 30 and an articulated axis 30' (as shown schematically in FIG. 1B), or to a second bent state having a total bend angle 33 (between articulated axis 30 and articulated axis 30"), with this second bend angle being greater than the first bend angle (as shown schematically in FIG. 1C). An exemplary structure for combining multiple discrete bend angle increments to form a total bend angle 33 can be understood with reference to FIG. 4C. Regardless, the additional total cumulative bend angle 33 may optionally be implemented by imposing the first bend 31 (of FIG. 1B) as a first increment along with one or more additional bend angle increments 35. The incremental changes to actuated portion 20 may be provided by fully inflating and/or deflating actuation balloons of the catheter system. Bend capabilities may be limited to a single lateral orientation, but will more typically be available in different lateral orientations, most typically in any of 3 or 4 orientations (for example, using balloons positioned along two pairs of opposed lateral axes, sometimes referred to as the +X, −X, +Y and −Y orientations), and by combining different bend orientations, in intermediate orientations as well. Continuous positioning may be implemented using similar articulation structures by partially inflating or deflating balloons or groups of balloons.

System 10 may also be configured to provide catheter 12 with any of a plurality of discrete alternative total axial lengths. As with the bend capabilities, such length actuation may also be implemented by inflating balloons of a balloon array structure. To provide articulation with the simple balloon array structures described herein, each actuation may be implemented as a combination of discrete, predetermined actuation increments (optionally together with one or more partial or modulated actuation) but may more often be provided using modulated or partial inflation of balloons.

Referring now to FIGS. 1-1 and 2, embodiments of articulation system 10 will move the distal end 24 of catheter 12 toward a desired position and/or orientation in a workspace relative to a base portion 21, with the base portion often being adjacent to and proximal of actuated portion 20. Note that such articulation may be relatively (or even completely) independent of any bending of catheter body 12 proximal of base portion 21. The location and orientation of proximal base 21 (relative to handle 14 or to another convenient fixed or movable reference frame) may be identified, for example, by including known catheter position and/or orientation identification systems in system 10, by including radiopaque or other high-contrast markers and associated imaging and position and/or orientation identifying image processing software in system 10, by including a flexible body state sensor system along the proximal portion of catheter body 12, by foregoing any flexible length of catheter body 12 between proximal handle 14 and actuated portion 20, or the like. A variety of different degrees of freedom may be provided by actuated portion 20. Exemplary embodiments of articulation system 10 may allow, for example, distal end 24 to be moved with 2 degrees of freedom, 3 degrees of freedom, 4 degrees of freedom, 5 degrees of freedom, or 6 degrees of freedom relative to base portion 21. The number of kinematic degrees of freedom of articulated portion 20 may be much higher in some embodiments, particularly when a number of different alternative subsets of the balloon array could potentially be in different inflation states to give the same resulting catheter tip and/or tool position and orientation.

Note that the elongate catheter body 12 along and beyond actuated portion 20 may (and often should) remain flexible before, during, and after articulation, so as to avoid inadvertently applying lateral and/or axial forces to surrounding tissues that are beyond a safe threshold. Nonetheless, embodiments of the systems described herein may locally and controllable increase a stiffness of one or more axial portions of catheter body 12, along actuated portion 20, proximal of actuated portion 20, and/or distal of actuated portion 20. Such selective stiffening of the catheter body may be implemented with or without active articulation capabilities, may extend along one or more axial portion of catheter body 12, and may alter which portions are stiffened and which are more flexible in response to commands from the user, sensor input (optionally indicating axial movement of the catheter), or the like.

As shown in FIG. 2, actuated portion 20 may comprise an axial series of 2 or more (and preferably at least 3) actuatable sub-portions or segments 20', 20", 20''', with the segments optionally being adjacent to each other, or alternatively separated by relatively short (less than 10 diameters) and/or relatively stiff intermediate portions of catheter 12. Each sub-portion or segment may have an associated actuation array, with the arrays working together to provide the desired overall catheter shape and degrees of freedom to the tip or tool. At least 2 of the sub-portions may employ similar articulation components (such as similar balloon arrays, similar structural backbone portions, similar valve systems, and/or similar software). Commonality may include the use of corresponding actuation balloon arrays, but optionally with the characteristics of the individual actuation balloons of the different arrays and the spacing between the locations of the arrays varying for any distal tapering of the catheter body. There may be advantages to the use of differentiated articulation components, for example, with proximal and distal sub portions, 20', 20''' having similar structures that are configured to allow selective lateral bending with at least two degrees of freedom, and intermediate portion 20" being configured to allow variable axial elongation. In many embodiments, however, at least two (and preferably all) segments are substantially continuous and share common components and geometries, with the different segments having separate fluid channels and being separately articulatable but each optionally providing similar movement capabilities.

For those elongate flexible articulated structures described herein that include a plurality of axial segments, the systems will often determine and implement each commanded articulation of a particular segment as a single consistent articulation toward a desired segment shape state that is distributed along that segment. In some exemplary embodiments, the nominal or resting segment shape state may be constrained to a 3 DOF space (such as by continuous combinations of two transverse lateral bending orientations and an axial (elongation) orientation in an X-Y-Z work space). In some of the exemplary embodiments described herein (including at least some of the helical extension/contraction embodiments), lateral bends along a segment may be at least approximately planar when the segment is in or near a design axial length configuration (such as at or near the middle of the axial or Z range of motion), but may exhibit a slight but increasing off-plane twisting curvature as the segment moves away from that design configuration (such as near the proximal and/or distal ends of the axial range of motion). The off-plane bending may be repeatably accounted for kinematically by determining the changes in lateral orientation of eccentric balloons resulting from winding and unwinding of helical structures supporting those balloons when the helical structures increase and decrease in axial length. For example, a segment may be commanded (as part of an overall desired pose or movement) to bend in a −Y orientation with a 20 degree bend angle. If the bend is to occur at a design axial length (such as at the middle of the axial range of motion), and assuming balloons (or opposed balloon pairs) at 4 axial bend locations can be used to provide the commanded bend, the balloons (or balloon pairs) may each be inflated or deflated to bend the segment by about 5 degrees (thereby providing a total bend of 5*4 or 20 degrees) in the −Y orientation. If the same bend is to be combined with axial lengthening of the segment to the end of its axial range of motion, the processor may determine that the segment may would exhibit some twist (say 2 degrees) so that there would be a slight +X component to the commanded bend, so that the processor may compensate for the twist by commanding a corresponding −X bend component, or by otherwise compensating in the command for another segment of the flexible body.

Figure 3:
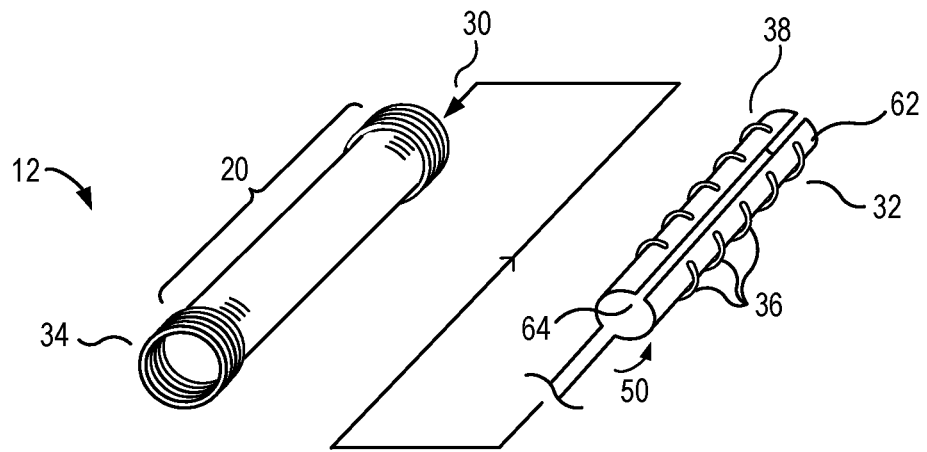
FIG. 3 is a simplified exploded perspective view showing a balloon array that can be formed in a substantially planar configuration and rolled into a cylindrical configuration, and which can be mounted coaxially to a helical coil or other skeleton framework for use in the catheter of the system of FIGS. 1 and 2.
Figure 5:
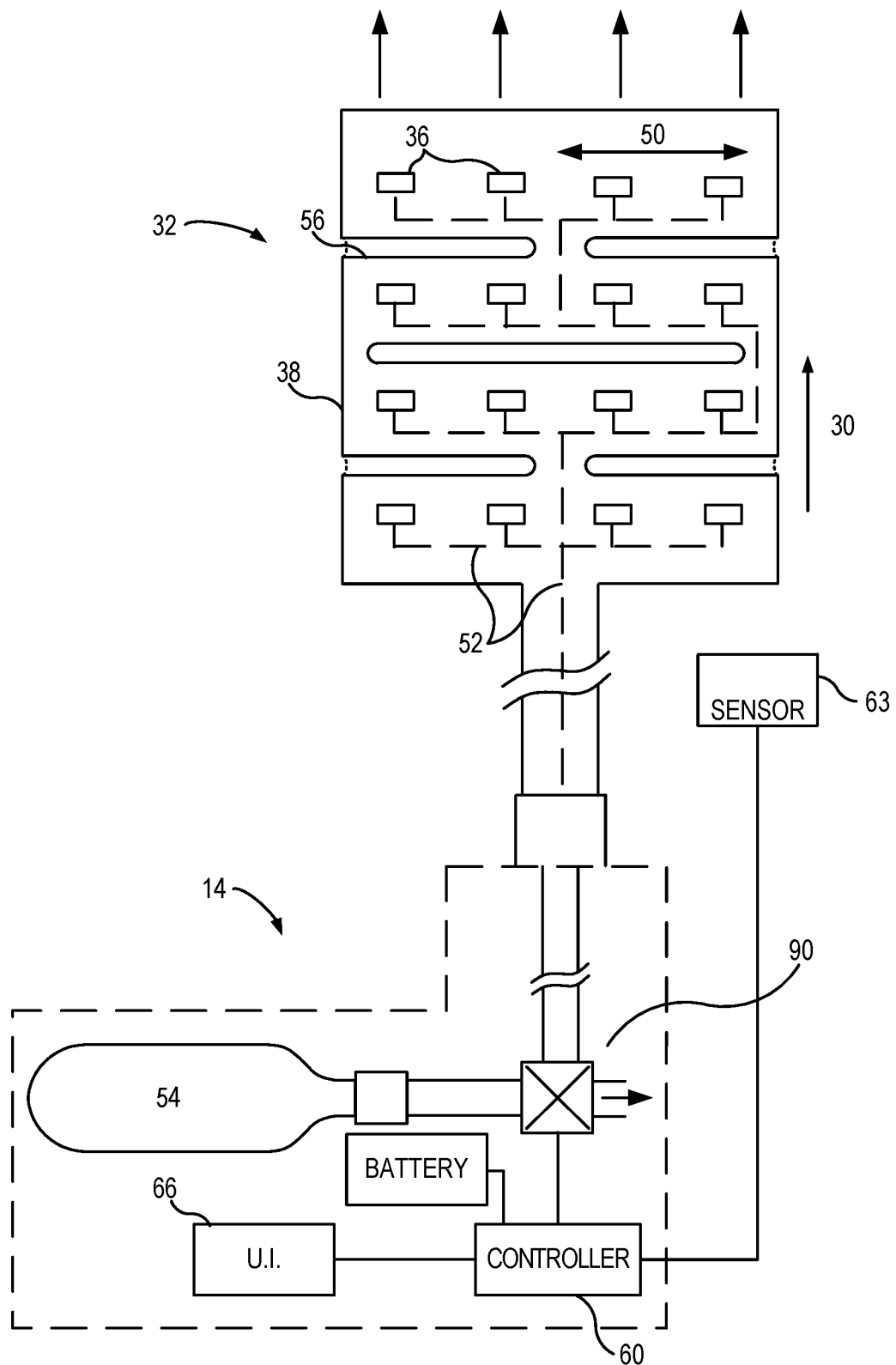
FIG. 5 schematically illustrates components for use in the catheter system of FIG. 1, including the balloon array, inflation fluid source, fluid control system, and processor.

Referring to FIGS. 3 and 5, catheter body 12 of system 10 includes an actuation array structure 32 mounted to a structural skeleton (here in the form of a helical coil 34). Exemplary balloon array 32 includes fluid expandable structures or balloons 36 distributed at balloon locations along a flexible substrate 38 so as to define an M×N array, in which M is an integer number of balloons distributed about a circumference 50 of catheter 12 at a given location along axis 30, and N represents an integer number of axial locations along catheter 12 having actuation balloons. Circumferential and axial spacing of the array element locations will generally be known, and will preferably be regular. This first exemplary actuation array includes a 4×4 array for a total of 16 balloons; alternative arrays may be from 1×2 arrays for a total of 2 balloons to 8×200 arrays for a total of 1600 balloons (or beyond), more typically having from 3×3 to 6×20 arrays. While balloon arrays of 1×N may be provided (particularly on systems that rely on rotation of the catheter body to orient a bend), M will more typically be 2 or more, more often being from 3 to 8, and preferably being 3 or 4. Similarly, while balloon arrays of M×1 may be provided to allow imposition of a single bend increment at a particular location in any of a number of different desired lateral orientations, array 32 will more typically have an N of from 2 to 200, often being from 3 to 20 or 3 to 100. In contraction/expansion embodiments described below, multiple arrays may be provided with similar M×N arrays mounted in opposition. Not all array locations need have inflatable balloons, and the balloons may be arranged in more complex arrangements, such as with alternating circumferential numbers of balloons along the axis, or with varying or alternating separation between balloons along the axial length of the array.

The balloons of a particular segment or that are mounted to a common substrate may be described as forming an array, with the actuation balloon array structure optionally being used as a sub-array in a multi-segment or opposed articulation system. The combined sub-arrays together may form an array of the overall device, which may also be described simply as an array or optionally an overall or combined array. Exemplary balloon arrays along a segment or sub-portion of articulated portion 20 include 1×8, 1×12, and 1×16 arrays for bending in a single direction (optionally with 2, 3, 4, or even all of the balloons of the segment in fluid communication with a single common inflation lumen so as to be inflated together) and 4×4, 4×8, and 4×12 arrays for X-Y bending (with axially aligned groups of 2-12 balloons coupled with 4 or more common lumens for articulation in the +X, −X, +Y, and −Y orientations). Exemplary arrays for each segment having the opposed extension/retraction continuous articulation structures described herein may be in the form of a 3×2N, 3×3N, 4×2, or 4×3N balloons arrays, for example, 3×2, 3×4, 3×6, 3×8, 3×10, 3×12, 3×14, and 3×16 arrays with 6 to 48 balloons, with the 3 lateral balloon orientations separated by 120 degrees about the catheter axis. Extension balloons will often be axially interspersed with contraction balloons along each lateral orientation, with separate 3×N arrays being combined together in a 3×2N extension/contraction array for the segment, while two extension balloons may be positioned axially between each contraction balloon for 3×3N arrangements. The contraction balloons may align axially and/or be in plane with the extension balloons they oppose, though it may be advantageous in some embodiments to arrange opposed balloons offset from a planer arrangement, so that (for example) two balloons of one type balance one balloon of the other, or vice versa. The extension balloons along each orientation of the segment may share a common inflation fluid supply lumen while the contraction balloons of the segment for each orientation similarly share a common lumen (using 6 fluid supply lumens per segment for both 3×2N and 3×3N arrays). An extension/contraction catheter may have from 1 to 8 such segments along the articulated portion, more typically from 1 to 5 segments, and preferably being 2 to 4 segments. Other medical and non-medical elongate flexible articulated structures may have similar or more complex balloon articulation arrays.

As can be seen in FIGS. 3, 4A, 4B, and 4C, the skeleton will often (though not always) include an axial series of loops 42. When the loops are included in a helical coil 34, the coil may optionally be biased so as to urge adjacent loops 42 of the coil 34 toward each other. Such axially compressive biasing may help urge fluid out and deflate the balloons, and may by applied by other structures (inner and/or outer sheath(s), pull wires, etc.) with or without helical compression. Axial engagement between adjacent loops (directly, or with balloon walls or other material of the array between loops) can also allow compressive axial forces to be transmitted relatively rigidly when the balloons are not inflated. When a particular balloon is fully inflated, axial compression may be transmitted between adjacent loops by the fully inflated balloon wall material and by the fluid within the balloons. Where the balloon walls are non-compliant, the inflated balloons may transfer these forces relatively rigidly, though with some flexing of the balloon wall material adjacent the balloon/skeleton interface. Rigid or semi-rigid interface structures which distribute axial loads across a broader balloon interface region may limit such flexing. Axial tension forces (including those associated with axial bending) may be resisted by the biasing of the skeleton (and/or by other axial compressive structures). Alternative looped skeleton structures may be formed, for example, by cutting hypotube with an axial series of lateral incisions across a portion of the cross-section from one or more lateral orientations, braided metal or polymer elements, or the like. Non-looped skeletons may be formed using a number of alternative known rigid or flexible robotic linkage architectures, including with structures based on known soft robot structures. Suitable materials for coil 34 or other skeleton structures may comprise metals such as stainless steel, spring steel, superelastic or shape-memory alloys such as Nitinol™ alloys, polymers, fiber-reinforced polymers, high-density or ultrahigh-density polymers, or the like.

When loops are included in the skeleton, actuation array 32 can be mounted to the skeleton with at least some of the balloons 36 positioned between two adjacent associated loops 42, such as between the loops of coil 34. Referring now to FIG. 4C, an exemplary deflated balloon 36i is located between a proximally adjacent loop 42i and a distally adjacent loop 42ii, with a first surface region of the balloon engaging a distally oriented surface of proximal loop 34i, and a second surface region of the balloon engaging a proximally oriented surface of distal loop 42ii. The walls of deflated balloon 36i have some thickness, and the proximal and distal surfaces of adjacent loops 42i and 42ii maintain a non-zero axial deflated offset 41 between the loops. Axial compression forces can be transferred from the loops through the solid balloon walls. Alternative skeletal structures may allow the loops to engage directly against each other so as to have a deflated offset of zero and directly transmit axial compressive force, for example by including balloon receptacles or one or more axial protrusions extending from one or both loops circumferentially or radially beyond the balloon and any adjacent substrate structure. Regardless, full inflation of the balloon will typically increase the separation between the adjacent loops to a larger full inflation offset 41'. The simplified lateral cross-sections of FIGS. 4B, 4C, and 4D schematically show a direct interface engagement between a uniform thickness thin-walled balloon and a round helical coil loop. Such an interface may result in relatively limited area of the balloon wall engaging the coil and associated deformation under axial loading. Alternative balloon-engaging surface shapes along the coils (often including locally increased convex radii, locally flattened surfaces, and/or local concave balloon receptacles) and/or along the coil-engaging surfaces of the balloon (such as by locally thickening the balloon wall to spread the engagement area), and/or providing load-spreading bodies between the balloons and the coils may add axial stiffness. A variety of other modifications to the balloons and balloon/coil interfaces may also be beneficial, including adhesive bonding of the balloons to the adjacent coils, including folds or material so as to inhibit balloon migration, and the like.

Inflation of a balloon can alter the geometry along catheter body 12, for example, by increasing separation between loops of a helical coil so as to bend axis 30 of catheter 12. As can be understood with reference to FIGS. 1B, 1C and 4-4C, selectively inflating an eccentric subset of the balloons can variably alter lateral deflection of the catheter axis. As can be understood with reference to FIGS. 1A, 4, and 4D, inflation of all (or an axisymmetric subset) of the balloons may increase an axial length of the catheter structure. Inflating subsets of the balloons that have a combination of differing lateral orientations and axial positions can provide a broad range of potential locations and orientations of the catheter distal tip 26, and/or of one or more other locations along the catheter body (such as where a tool is mounted).

Some or all of the material of substrate 38 included in actuation array 32 will often be relatively inelastic. It may, however, be desirable to allow the skeleton and overall catheter to flex and/or elongate axially with inflation of the balloons or under environmental forces. Hence, array 32 may have cutouts 56 so as to allow the balloon array to move axially with the skeleton during bending and elongation. The array structure could alternatively (or in addition) be configured for such articulation by having a serpentine configuration or a helical coiled configuration. Balloons 36 of array 32 may include non-compliant balloon wall materials, with the balloon wall materials optionally being formed integrally from material of the substrate or separately. Note that elastic layers or other structures may be included in the substrate for use in valves and the like, and that some alternative balloons may include elastic and/or semi-compliant materials.

Figure 4A:
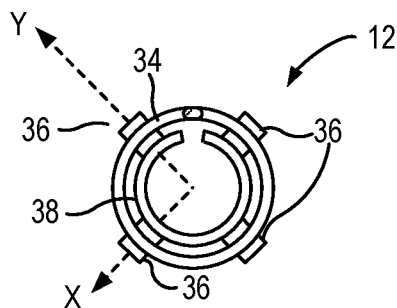
FIGS. 4A and 4B are a simplified cross-section and a simplified transverse cross-section, respectively, of an articulatable catheter for use in the system of FIG. 1, shown here with the balloons of the array in an uninflated, small axial profile configuration and between loops of the coil.
Figure 4B:
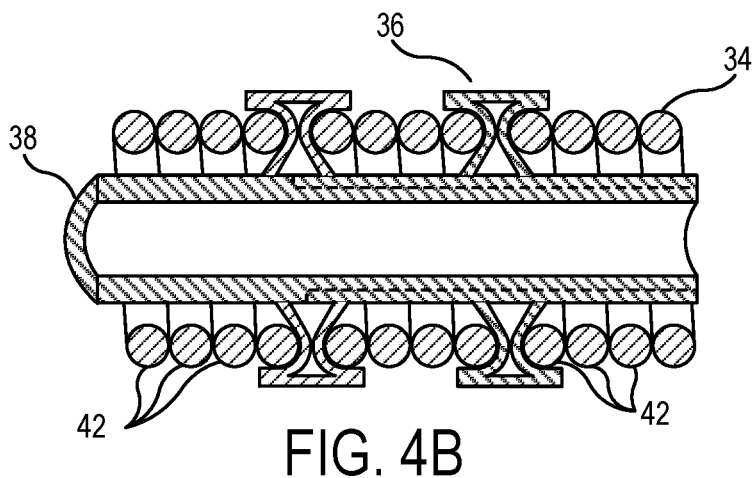
Figure 4C:
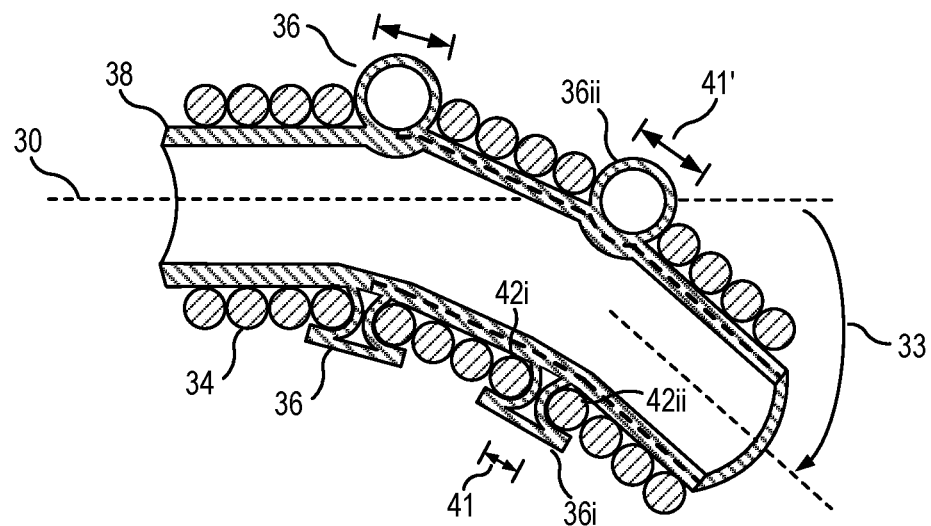
FIG. 4C is a simplified transverse cross-section of the articulatable catheter of FIGS. 4A and 4B, with a plurality of axially aligned balloons along one side of the articulatable region of the catheter inflated so that the catheter is in a laterally deflected state.
Figure 4D:
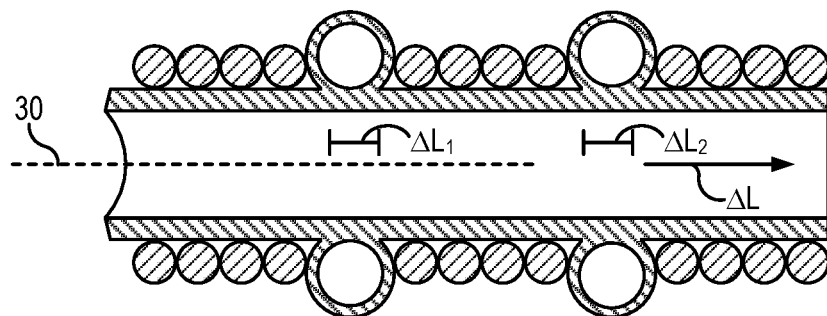
FIG. 4D is a simplified transverse cross-section of the articulatable catheter of FIG. 4, with a plurality of laterally opposed balloons inflated so that the catheter is in an axially elongated state.

Referring to FIGS. 3, 4A, and 5, substrate 38 of array 32 is laterally flexible so that the array can be rolled or otherwise assume a cylindrical configuration when in use. The cylindrical array may be coaxially mounted to (such as being inserted into or radially outwardly surrounding) the helical coil 34 or other structural backbone of the catheter. The cylindrical configuration of the array will generally have a diameter that is equal to or less than an outer diameter of the catheter. The opposed lateral edges of substrate 38 may be separated by a gap as shown, may contact each other, or may overlap. Contacting or overlapping edges may be affixed together (optionally so as to help seal the catheter against radial fluid flow) or may accommodate relative motion (so as to facilitate axil flexing). In some embodiments, lateral rolling or flexing of the substrate to form the cylindrical configuration may be uniform (so as to provide a continuous lateral curve along the major surfaces), while in other embodiments intermittent axial bend regions of the substrate may be separated by axially elongate relatively flat regions of the substrate so that a cylindrical shape is approximated by a prism-like arrangement (optionally so as to limit bending of the substrate along balloons, valves, or other array components).

It will often (though not always) be advantageous to form and/or assemble one or more components of the array structure in a flat, substantially planar configuration (and optionally in a linear configuration as described below). This may facilitate, for example, partial or final formation of balloons 36 on substrate 38, or alternatively, attachment of pre-formed balloons to the substrate. The flat configuration of the substrate may also facilitate the use of known extrusion or microfluidic channel fabrication techniques to provide fluid communication channels 52 so as to selectively couple the balloons with a fluid inflation fluid source or reservoir 54, and the like. Still further advantages of the flat configuration of the substrate may include the use of electrical circuit printing techniques to fabricate electrical traces and other circuit components, automated 3-D printing techniques (including additive and/or removal techniques) for forming valves, balloons, channels, or other fluid components that will be supported by substrate 38, and the like. When the substrate is in a rolled, tubular, or flat planar configuration, the substrate will typically have a first major surface 62 adjacent balloons 36, and a second major surface 64 opposite the first major surface (with first major surface 62 optionally being a radially inner or outer surface and second major surface 64 being a radially outer or inner surface, respectively, in the cylindrical configuration). To facilitate flexing substrate 38 and array 32 into the rolled configuration, relief cuts or channels may be formed extending into the substrate from the first and/or second major surfaces, or living hinge regions may otherwise be provided between relatively more rigid portions of the substrate. To further avoid deformation of the substrate adjacent any valves or other sensitive structures, local stiffening reinforcement material may be added, and/or relief cuts or apertures may be formed partially surrounding the valves. In some embodiments, at least a portion of the array components may be formed or assembled with the substrate at least partially in a cylindrical configuration, such as by bonding layers of the substrate together while the substrate is at least locally curved, forming at least one layer of the substrate as a tube, selectively forming cuts in the substrate (optionally with a femtosecond, picosecond, or other laser) to form fluid, circuit, or other components or allow for axial flexing and elongation (analogous to cutting a stent to allow for axial flexing and radial expansion) and/or to form at least some of the channels, and bonding the layers together after cutting.

As can be understood with reference to FIGS. 5 and 5A, substrate 38 of array 32 may include one or more layers of flexible substrate material. The substrate layers may comprise known flexible and/or rigid microfluidic substrate materials, such as polydimethylsiloxane (PDMS), polyimide (PI), polyethylene (PE) and other polyolefins, polystyrene (PS), polyethylene terephthalate (PET), polypropylene (PP), polycarbonate (PC), nanocomposite polymer materials, glass, silicon, cyclic olefin copolymer (COC), polymethyl methacrylate (PMMA), polyetheretherketone (PEEK), polyester, polyurethane (PU), and/or the like. These and still further known materials may be included in other components of actuation array 32, including known polymers for use in balloons (which will often include PET, PI, PE, polyether block amide (PEBA) polymers such as PEBAX™ polymers, nylons, urethanes, polyvinyl chloride (PVC), thermoplastics, and/or the like for non-compliant balloons; or silicone, polyurethane, semi-elastic nylons or other polymers, latex, and/or the like for compliant or semi-compliant balloons). Additional polymers than may be included in the substrate assembly may include valve actuation elements (optionally including shape memory alloy structures or foils; phase-change actuator materials such as paraffin or other wax, electrical field sensitive hydrogels, bimetallic actuators, piezoelectric structures, dielectric elastomer actuator (DEA) materials, or the like). Hence, while some embodiments may employ homogenous materials for actuation array 32, many arrays and substrate may instead be heterogeneous.

Fortunately, techniques for forming and assembling the components for actuation array 32 may be derived from a number of recent (and relatively widely-reported) technologies. Suitable techniques for fabricating channels in substrate layer materials may include laser micromachining (optionally using femtosecond or picosecond lasers), photolithography techniques such as dry resist technologies, embossing (including hot roller embossing), casting or molding, xerographic technologies, microthermoforming, stereolithography, 3-D printing, and/or the like. Suitable 3-D printing technologies that may be used to form circuitry, valves, sensors, and the like may include stereolithography, digital light processing, laser sintering or melting, fused deposition modeling, inkjet printing, selective deposition lamination, electron beam melting, or the like. Assembly of the components of actuation array 32 may make use of thermal or adhesive bonding between layers and other components, though laser, ultrasound, or other welding techniques; microfasteners, or the like may also be used. Electrical element fabrication of conductive traces, actuation, signal processor, and/or sensor components carried by substrate 38 may, for example, use ink-jet or photolithography techniques, 3-D printing, chemical vapor deposition (CVD) and/or more specific variants such as initiated chemical vapor deposition (iCVD), robotic microassembly techniques, or the like, with the electrical traces and other components often comprising inks and other materials containing metals (such as silver, copper, or gold) carbon, or other conductors. Many suitable fabrication and assembly techniques have been developed during development of microfluidic lab-on-a-chip or lab-on-a-foil applications. Techniques for fabricating medical balloons are well developed, and may optionally be modified to take advantage of known high-volume production techniques (optionally including those developed for fabricating bubble wrap, for corrugating extruded tubing, and the like). Note that while some embodiments of the actuation array structures described herein may employ fluid channels sufficiently small for accurately handling of picoliter or nanoliter fluid quantities, other embodiments will include channels and balloons or other fluid-expandable bodies that utilize much larger flows so as to provide desirable actuation response times. Balloons having at least partially flexible balloon walls may provide particular advantages for the systems described herein, but alternative rigid fluid expandable bodies such as those employing pistons or other positive displacement expansion structures may also find use in some embodiments.

The structures of balloons 36 as included in actuation array 32 may be formed of material integral with other components of the array, or may be formed separately and attached to the array. Balloons 36 may be formed from or attached to a first sheet of substrate material that can be bonded or otherwise affixed to another substrate layer or layers. The material of the balloon layer may optionally cover portions of the channels directly, or may be aligned with apertures that open through an intermediate substrate layer surface between the channels and the balloons. Alternative methods for fabricating individual balloons are well known, and the formed balloons may be affixed to the substrate 38 by adhesive bonding. Balloon shapes may comprise relatively simple cylinders or may be somewhat tailored to taper to follow an expanded offset between loops of a coil, to curve with the cylindrical substrate and/or to engage interface surfaces of the skeleton over a broader surface area and thereby distribute actuation and environmental loads. Effective diameters of the balloons in the array may range from about 0.003 mm to as much as about 2 cm (or more), more typically being in a range from about 0.3 mm to about 2 mm or 5 mm, with the balloon lengths often being from about 2 to about 15 times the diameter. Typical balloon wall thicknesses may range from about 0.0002 mm to about 0.004 mm (with some balloon wall thicknesses being between 0.0002 mm and 0.020 mm), and full inflation pressures in the balloons may be from about 0.2 to about 40 atm, more typically being in a range from about 0.4 to about 30 atm, and in some embodiments being in a range from about 10 to about 30 atm, with high-pressure embodiments operating at pressures in a range as high as 20-45 atm and optionally having burst pressures of over 50 atm.

Referring now to FIG. 5, balloons 36 will generally be inflated using a fluid supply system that includes a fluid source 54 (shown here as a pressurized single-use cartridge) and one or more valves 90. At least some of the valves 90 may be incorporated into the balloon array substrate, with the valves optionally being actuated using circuitry printed on one or more layers of substrate 38. With or without substrate-mounted valves that can be used within a patient body, at least some of the valves may be mounted to housing 14, or otherwise coupled to the proximal end of catheter 12. Valves 90 will preferably be coupled to channels 52 so as to allow the fluid system to selectively inflate any of a plurality of alternative individual balloons or subsets of balloons 36 included in actuation array 32, under the direction of a processor 60. Hence, processor 60 will often be coupled to valves 90 via conductors, the conductors here optionally including flex circuit traces on substrate 38.

Referring still to FIG. 5, fluid source 54 may optionally comprise a separate fluid reservoir and a pump for pressurizing fluid from the reservoir, but will often include a simple tank or cartridge containing a pressurized fluid, the fluid optionally being a gas or a gas-liquid mixture. The cartridge will often maintain the fluid at a supply pressure at or above a full inflation pressure range of balloons 36, with the cartridge optionally being gently heated by a resistive heater or the like (not shown) in housing 14 so as to maintain the supply pressure within a desired range in the cartridge during use. Supply pressures will typically exceed balloon inflation pressures sufficiently to provide balloon inflation times within a target threshold given the pressure loss through channels 52 and valves 90, with typical supply pressures being between 10 and 210 atm, and more typically being between 20 and 60 atm. Suitable fluids may include known medical pressurized gases such as carbon dioxide, nitrogen, oxygen, nitrous oxide, air, known industrial and cryogenic gasses such as helium and/or other inert or noble gasses, refrigerant gases including fluorocarbons, and the like. Note that the pressurized fluid in the canister can be directed via channels 52 into balloons 36 for inflation, or the fluid from the canister (often at least partially a gas) may alternatively be used to pressurize a fluid reservoir (often containing or comprising a benign biocompatible liquid such as water or saline) so that the balloon inflation fluid is different than that contained in the cartridge. Where a pressurized liquid or gas/liquid mixture flows distally along the catheter body, enthalpy of vaporization of the liquid in or adjacent to channels 52, balloons 36, or other tissue treatment tools carried on the catheter body (such as a tissue dilation balloon, cryogenic treatment surface, or tissue electrode) may be used to therapeutically cool tissue. In other embodiments, despite the use of fluids which are used as refrigerants within the body, no therapeutic cooling may be provided. The cartridge may optionally be refillable, but will often instead have a frangible seal so as to limit re-use.

As the individual balloons may have inflated volumes that are quite small, cartridges that are suitable for including in a hand-held housing can allow more than a hundred, optionally being more than a thousand, and in many cases more than ten thousand or even a hundred thousand individual balloon inflations, despite the cartridge containing less than 10 ounces of fluid, often less than 5 ounces, in most cases less than 3 ounces, and ideally less than 1 ounce. Note also that a number of alternative fluid sources may be used instead of or with a cartridge, including one or more positive displacement pumps (optionally such as simple syringe pumps), a peristaltic or rotary pump, any of a variety of microfluidic pressure sources (such as wax or other phase-change devices actuated by electrical or light energy and/or integrated into substrate 38), or the like. Some embodiments may employ a series of dedicated syringe or other positive displacement pumps coupled with at least some of the balloons by channels of the substrate, and/or by flexible tubing.

Referring still to FIG. 5, processor 60 can facilitate inflation of an appropriate subset of balloons 36 of actuation array 32 so as to produce a desired articulation. Such processor-derived articulation can significantly enhance effective operative coupling of the input 18 to the actuated portion 20 of catheter body 12, making it much easier for the user to generate a desired movement in a desired direction or to assume a desired shape. Suitable correlations between input commands and output movements have been well developed for teleoperated systems with rigid driven linkages. For the elongate flexible catheters and other bodies used in the systems described herein, it will often be advantageous for the processor to select a subset of balloons for inflation based on a movement command entered into a user interface 66 (and particularly input 18 of user interface 66), and on a spatial relationship between actuated portion 20 of catheter 12 and one or more component of the user interface. A number of differing correlations may be helpful, including orientational correlation, displacement correlation, and the like. Along with an input, user interface 66 may include a display showing actuated portion 20 of catheter body 12, and sensor 63 may provide signals to processor 60 regarding the orientation and/or location of proximal base 21. Where the relationship between the input, display, and sensor are known (such as when they are all mounted to proximal housing 14 or some other common base), these signals may allow derivation of a transformation between a user interface coordinate system and a base coordinate system of actuated portion 20. Alternative systems may sense or otherwise identify the relationships between the sensor coordinate system, the display coordinate system, and/or the input coordinate system so that movements of the input result in catheter movement, as shown in the display. Where the sensor comprises an image processor coupled to a remote imaging system (such as a fluoroscopy, MM, or ultrasound system), high-contrast marker systems can be included in proximal base 21 to facilitate unambiguous determination of the base position and orientation. A battery or other power source (such as a fuel cell or the like) may be included in housing 14 and coupled to processor 60, with the housing and catheter optionally being used as a handheld unit free of any mechanical tether during at least a portion of the procedure. Nonetheless, it should be noted that processor 60 and/or sensor 63 may be wirelessly coupled or even tethered together (and/or to other components such as a separate display of user interface 66, an external power supply or fluid source, or the like).

Regarding processor 60, sensor 63, user interface 66, and the other data processing components of system 10, it should be understood that the specific data processing architectures described herein are merely examples, and that a variety of alternatives, adaptations, and embodiments may be employed. The processor, sensor, and user interface will, taken together, typically include both data processing hardware and software, with the hardware including an input (such as a joystick or the like that is movable relative to housing 14 or some other input base in at least 2 dimensions), an output (such as a medical image display screen), an image-acquisition device or other sensor, and one or more processor. These components are included in a processor system capable of performing the image processing, rigid-body transformations, kinematic analysis, and matrix processing functionality described herein, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Referring now to FIG. 5A, an alternative actuation array and fluid supply system are shown schematically. As in the above embodiment, balloons 36 are affixed along a major surface of substrate 38, optionally prior to rolling the substrate and mounting of the actuation array to the skeleton of the catheter body. In this embodiment, each balloon has an associated dedicated channel 52 of substrate 38, and also an associated valve 90. Processor 60 is coupled with valves 90, and by actuating a desired subset of the valves the associated subset of balloons can be inflated or deflated. In some embodiments, each valve can be associated with more than one balloon 36, so that (for example), opening of a single valve might inflate a plurality (optionally 2, 3, 4, 8, 12, or some other desired number) of balloons, such as laterally opposed balloons so as to elongate the distal portion of the catheter. In these or other embodiments, a plurality of balloons (2, 3, 4, 5, 8, 12, or another desired number) on one lateral side of the catheter could be in fluid communication with a single associated valve 90 via a common channel or multiple channels so that opening of the valve inflates the balloons and causes a multi-balloon and multi-increment bend in the axis of the catheter. Still further variations are possible. For example, in some embodiments, channels 52 may be formed at least in-part by flexible tubes affixed within an open or closed channel of substrate 38, or glued along a surface of the substrate. The tubes may comprise polymers (such as polyimide, PET, nylon, or the like), fused silica, metal, or other materials, and suitable tubing materials may be commercially available from Polymicro Technologies of Arizona, or from a variety of alternative suppliers. The channels coupled to the proximal end of the actuatable body may be assembled using stacked fluidic plates, with valves coupled to some or all of the plates. Suitable electrically actuated microvalues are commercially available from a number of suppliers. Optional embodiments of fluid supply systems for all balloon arrays described herein may have all values mounted to housing 14 or some other structure coupled to and/or proximal of) the proximal end of the elongate flexible body. Advantageously, accurately formed channels 52 (having sufficiently tight tolerance channel widths, depths, lengths, and/or bends or other features) may be fabricated using microfluidic techniques, and may be assembled with the substrate structure, so as to meter flow of the inflation fluid into and out of the balloons of all of the actuation arrays described herein.

A variety of known lab-on-a-chip and lab-on-a-foil production techniques can be used to assemble and seal the substrate layers, with many embodiments employing thermal fusion bonding, solvent bonding, welding (and particularly ultrasound welding), UV-curable adhesives, contact adhesives, nano-adhesives (including doubly cross-linked nano-adhesive or DCNA), epoxy-containing polymers (including polyglycidyl methacrylate), plasma or other surface modifications, and/or the like between layers. For high fluid pressure systems, third generation nano-adhesive techniques such as CVD deposition of less than 400 nanometer layers of DCNA materials may facilitate the use of high-strength polymer materials such as PET. Channels of such high-pressure systems may optionally be defined at least in part by PET and/or fused silica tubing (which may be supported by a substrate along some or all of the channel, and/or may be bundled together with other fused silica tubing along some or all of its length ideally in an organized array with tubing locations corresponding to the balloon locations within the balloon array, analogous to the organization of a coherent fiber optic bundle), or the like. Any valves mounted to the substrate of the balloon array may be electrically actuated using conductive traces deposited on a surface of a substrate layer prior to bonding, with an overlying layer sealing the traces in the interior of the substrate. Valve members may move when a potential is applied to an actuation material using the traces, with that material optionally comprising a shape-memory alloy, piezoelectric, an electrically actuated polymer, or the like. Still further alternative actuation materials may include phase change materials such as wax or the like, with the phase change being induced by electrical energy or optical energy (such as laser light transmitted via an optical fiber or printed pathway between layers of the substrate). In some embodiments, the actuation material and valve member may be formed using 3-D printing techniques. Multiplex circuitry may be included in, deposited on a layer of, or affixed to substrate 38 so that the number of electrical traces extending proximally along catheter body 12 may be less than the number of valves that can be actuated by those valves. The valves may take any of a wide variety of forms, and may employ (or be derived from) known valve structures such as known electrostatically-actuated elastomeric microfluidic valves, microfluidic polymer piston or free-floating gate valves, layered modular polymeric microvalves, dielectric elastomer actuator valves, shape memory alloy microvalves, hydrogel microactuator valves, integrated high-pressure fluid manipulation valves employing paraffin, and the like. Along with electrically actuated microvalves, suitable valves may be optically actuated, fluid actuated, or the like.

It should be understood that many of the valves shown herein are schematic, and that additional or more complex valves and channel systems may be included to control inflation and deflation of the balloons. One or more valves in the system may comprise gate valves (optionally normally closed, normally open or stable), so as to turn inflation fluid flow from the fluid source to at least one balloon on or off Deflation may optionally be controlled by a separate gate valve between each balloon (or groups of balloons) and one or more deflation port of substrate 38 (the fluid from the balloon optionally exiting from the substrate to flow proximally between radially inner and outer sealed layers of the catheter) or housing 14. Alternative 2-way valves may allow i) communication between either the fluid source and the balloon (with flow from the balloon being blocked), or ii) between the balloon and the deflation outflow (with the flow from the fluid source being blocked). Still further alternatives may be employed, including a 3 way valve having both of the above modes and iii) a sealed balloon mode in which the balloon is sealed from communication with the fluid source and from the deflation outflow (with flow from the source also being closed).

Figure 6:
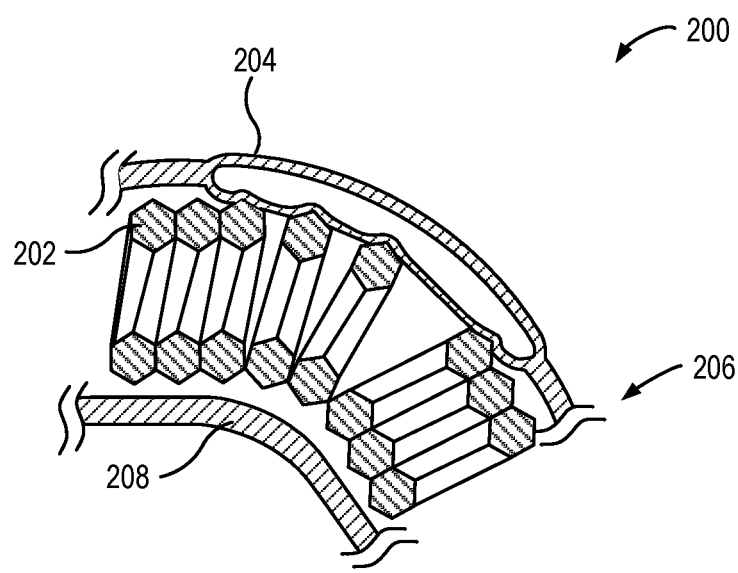
FIG. 6 is a simplified transverse cross-section of catheter wherein one or more balloons can be inflated to radially engage a plurality of loops of a helical coil so as to inhibit bending of a catheter axis.

Referring now to FIG. 6, an optional catheter structure employs an alternative balloon array structure having one or more elongate balloons 204 that each extend axially, with balloons 204 here being formed in a layered substrate 208 so that the balloons together define a balloon array 206 that can frictionally engage or latch against coils to help inhibit lateral bending of a catheter body. When deflated, the loops 202 of the helical coils can move away from (or if separated, toward) each other, allowing the catheter body to flex (and straighten). In contrast, fluid expansion of balloons 208 causes each axial balloon to radially engage a plurality of coils 202, inhibiting movement of the coils toward or away from each other so as to add axial stiffness to the catheter body. Interestingly, this can make it more difficult to bend a straight portion of the catheter, and/or can make it more difficult for a bent portion of the catheter to straighten (or otherwise alter its axial configuration). As described above, substrate 208 may be disposed between inner and outer coils so that the axially oriented balloons radially engage either (or both); or the substrate may be disposed radially outward of the coil to be engaged with the edges of the substrate affixed together so as to limit radial displacement of the balloons and promote firm radial engagement between the expanded balloon and the coil. Still further alternatives are available, including the use of semi-rigid or other radial support materials in the substrate, with or without edges affixed together. As can also be understood with reference to FIGS. 4C and 6, bend-inducing balloons may be combined with bend-inhibiting balloons by including both types of balloons on a single substrate (optionally on opposed sides) or on separate substrates. Advantageously, the substrate, balloon, and fluid supply and control structures of these bend-change-inhibiting balloon arrays may include the characteristics described above for the corresponding structures of the balloon articulation systems.

A number of inflation fluid supply system component arrangements for use in any or all of the articulation, stiffening, and/or bend control systems described herein can be understood with reference to FIGS. 7A-7F. As noted above, the valves, ports, and the like may be included in a proximal housing, may be incorporated into a substrate of the balloon array, or a combination of both. First addressing a simple inflation control arrangement 240 of FIG. 7A, a single on/off gate valve 242 may be along a fluid flow path between a fluid source 244 and a balloon 246. A limited flow exhaust port 248 remains open, and opening of valve 242 allows sufficient fluid from the source to inflate balloon despite a limited flow of fluid out of limited port 248, which can have an orifice or other fixed flow restriction. When gate valve 242 is closed, flow out of the limited port 248 allows the balloon to deflate. The two-valve arrangement 250 of FIG. 7B uses two separate gate valves 242 to independently control flow into and out of the balloon, thereby limiting the loss of fluid while the balloon remains inflated and also preventing deflation speed from being limited more than might otherwise be desired. While the inflow channel into the balloon and out of the balloon are shown as being separate here, both valves may instead be coupled to the inflow channel, with the deflation valve typically being between the inflation valve and the balloon.

Figure 7A:
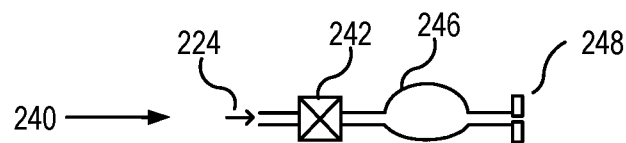
FIGS. 7A-7F schematically illustrate valve and balloon arrangements which may be used and/or combined in the inflation fluid supply systems of the systems and devices described herein.
Figure 7B:
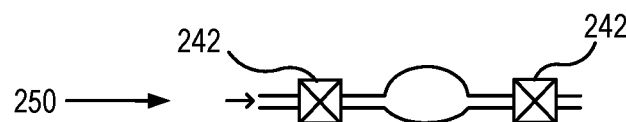
Figure 7C:
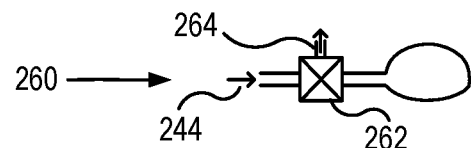

A two-way valve arrangement 260 is shown in FIG. 7C, with a two way valve 262 having a first mode that provides fluid communication between supply 244 and balloon 246, and a second mode that provides fluid communication between the balloon and an exhaust port 264 (while the supply is sealed to the port and balloon).

Figure 7D:
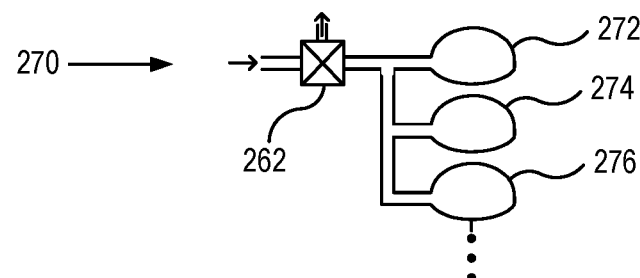

A ganged-balloon arrangement 270 is shown in FIG. 7D, with a two way valve 262 between supply 244 and a plurality of balloons 272, 274, 276, . . . . Such an arrangement allows a number (typically between 2 and 10 balloons) to be inflated and deflated using a single valve, which may be used when a subset of balloons are often to be inflated, such as for elongation of an axial segment, for imposing a desired base curvature (to which other incremental axial bend components may be added), for imposing multi-balloon incremental axial bend components or the like.

Figure 7E:
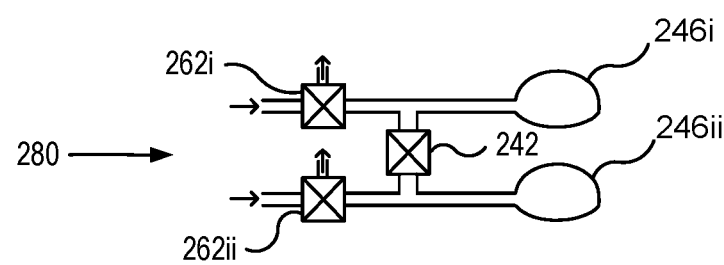

A transfer-bend valve arrangement 280 is shown in FIG. 7E, with two way valves 262i, 262ii each allowing inflation of an associated balloon 246i, 246ii, respectively. Additionally, a transfer gate valve 242 between balloons 246i and 246ii allows inflation fluid to flow from one (or more) balloon to another (one or more) balloon. This may allow, for example, a bend associated with one balloon to be transferred partially or fully to a bend associated with a different balloon in response to environmental forces against the flexible body, such as when a catheter is pushed axially within a bent body lumen (so that the bend transfers axially), when a catheter is rotated within a bent body lumen (so that the bend transfers laterally), a combination of the two, or the like. A transfer valve may also be used, for example, help determine a catheter shape that limits forces imposed between a surrounding lumenal wall and the catheter structure. For this (and potentially other advantageous uses) a valve may be opened between a full-inflation pressure source and one or more balloon to initially inflate such balloon(s) so that the catheter is urged toward an initial state. At least one transfer valve may be opened between the inflated balloon(s) and one or more uninflated balloons so as to drive the catheter configuration having a bend. If the tissue surrounding the bend (and internal balloon compression structures of the catheter) urge deflation of the inflated balloons with sufficient force, and if the surrounding tissue urge the catheter to assume another bend associated with those uninflated balloon(s) so as to mitigate the internal balloon compression structures of the catheter, inflation fluid can be forced from the inflated balloon(s) to the uninflated balloon(s), and the catheter can then allow the tissue to assume a more relaxed shape. Interestingly, changes in the catheter bend configuration associated with inflation fluid flowing between balloons may at least in part be pseudo-plastic, with fluid flow resistance limiting elastic return to the prior state. Use of a flow modulating transfer valve (as opposed to a simple on/off gate valve) may allow corresponding modulation of this pseudo-plastic bend state change. Alternatively, a transfer valve and associated channel may have a tailored flow resistance (such as an orifice or controlled effective diameter section) to tailor the pseudo-plastic properties.

Figure 7F:
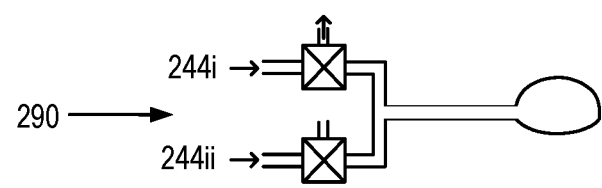

A multi-pressure valve arrangement 290 is shown in FIG. 7F, in which a two-way valve allows inflation or deflation of an associated balloon from a full inflation supply 244i as described above. Alternatively, a partial inflation fluid supply 244ii can direct fluid at a lower (optionally fixed) partial inflation pressure to the same balloon. The partial inflation pressure may be insufficient to overcome the bias of the helical coil and the like toward balloon deflation and a straight-coil configuration, and thus may not alone bend the flexible body (absent tissue or other environmental forces against the catheter), but can selectively reduce the strength of the catheter against a bend associated with the partially inflated balloon. Alternatively, the pressure may be sufficient to partially inflate the balloon and induce a portion of a full-inflation bend. Regardless, one or more partial inflation fluid supply pressures may be provided using one or more associated valves, with the inflation fluid being a one or more incremental pressures between a full balloon inflation pressure and atmospheric pressure. Note that partial inflation may alternatively be provided by modulating a variable valve for a limited inflation time so as to control total fluid flow quantity to one or more balloons, by controlling one or more on/of pulse cycles times of a gate valve, or the like. Still other combinations of inflation fluid directing components may be included in many embodiments, with at least some of the components (and particularly channels between the valves and the balloons) being integrated into the balloon array, at least some of the components (particularly the pressurized fluid canister or other source) being in a proximal housing coupled to a proximal end of the catheter or other flexible body, and others (portions of the channels, valves, ports, valve actuation circuitry, etc.) being in either or distributed in both. In some embodiments, a non-actuating positive inflation fluid pressure (greater than the atmosphere surrounding the balloon array but insufficient to separate loops of a coil) may be maintained in some or all of the balloons that are in a nominally non-inflated state. This may pre-inflate the balloons so that the fluid partially fills the balloon and the balloon wall expands where it does not engage the coil, decreasing the quantity of fluid that flows to the balloon to achieve full inflation.

A wide variety of desirable inflation fluid supply system capabilities can be provided using one or more valve component arrangements described above. For example, rather than including a separate partial inflation pressure fluid supply, a transfer valve can be used to first fully inflate a first balloon, after which a transfer valve can be used to transfer a portion of the fluid from the inflated balloon to one or more other balloons, resulting in gang partial inflation of multiple balloons. A fluid supply system may have a network of channels with a combination of inflation gate valves and deflation gate valves so as to allow selective inclusion of any of a plurality of individual balloons in an inflated subset, selected ganged balloons that pre-define some or all of the members of subsets that will be used simultaneously, and the like.

Figure 8:
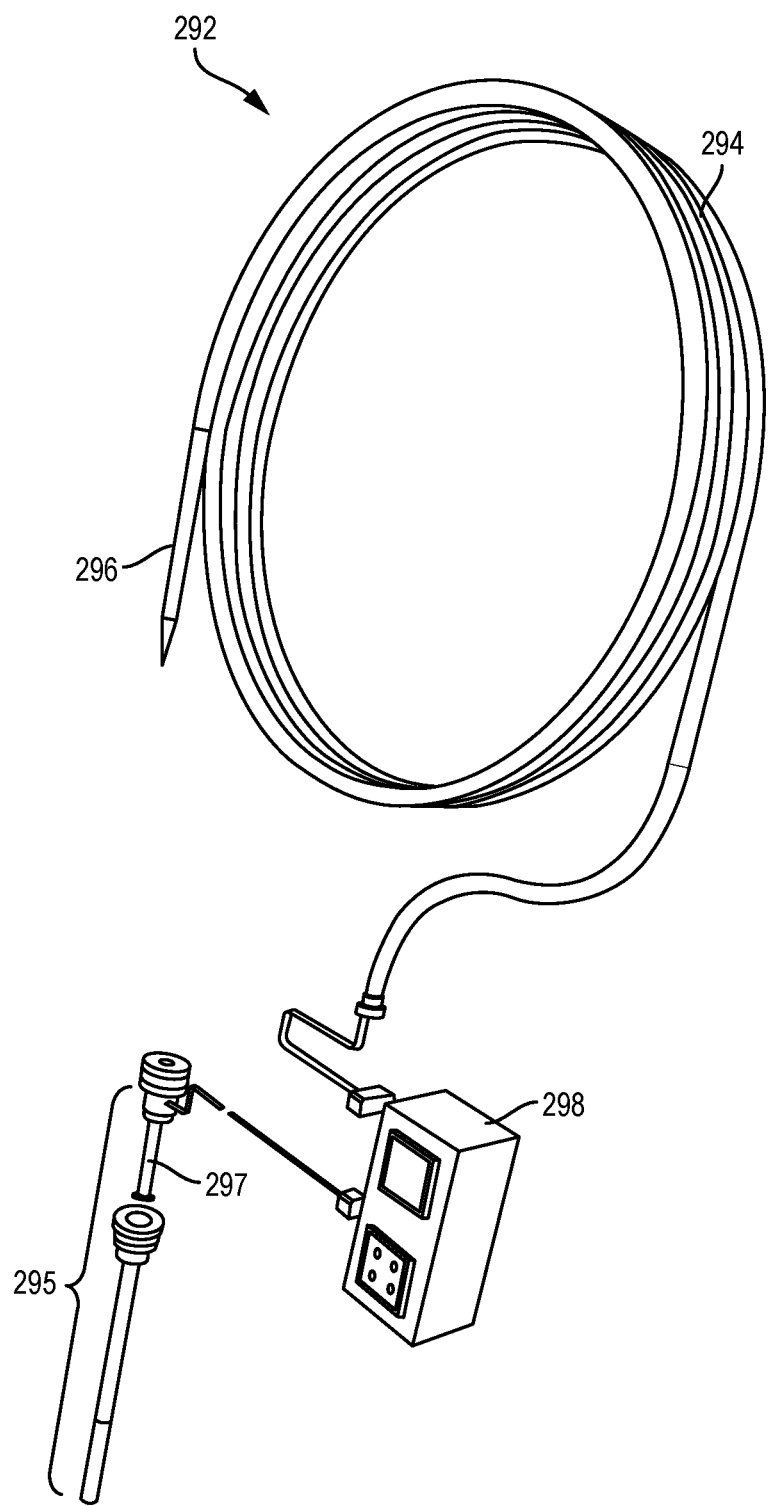
FIG. 8 schematically illustrates a catheter articulation system in which an input of the system is incorporated with an introducer sheath.

Referring now to FIG. 8, components of an exemplary catheter articulation system 292 can be seen, with these components generally being suitable for use in catheter system 1 of FIG. 1. In this embodiment, a catheter 294 has a distal articulated portion 296, with the articulated portion optionally including axially separate articulation sub-portions or segments, and alternatively having a single relatively continuously articulated length. An insertion sheath/input assembly 295 is included in the system user interface, and both assembly 295 and the proximal end of catheter 294 are detachably coupleable with a proximal housing 298 using flexible cables (and quick-disconnect couplers), with the housing containing a battery, a processor, a replaceable compressed fluid cartridge, valves, and the like. Housing 298 also includes or contains additional components of the user interface, and is sized for positioning by a single hand of a user, but need not be moved during use of catheter 294. Commands to effect automated bending and elongation of distal portion 296 during use may optionally be input into the system by bending and axial insertion of input 297 relative to a proximal body of the introducer sheath, thereby employing manual movements of the user which are already familiar to physicians that employ catheter-based diagnostic and therapeutic tools.

Regarding some of the user interface components of articulation system 292, use of input 297 for controlling the articulation state of catheter 294 will be described in more detail hereinbelow. In addition to input 297, a number of additional (or alternative) user interface components may be employed. As generally indicated above, the user interface may include a housing affixed to a proximal end of catheter 294, with the housing having a joystick as described above regarding FIG. 1-1. Trackballs or touchpads may be provided in place of a joystick, and as the catheters and other structures described herein may have more than two degrees of freedom, some embodiments may include two offset joysticks, with a more proximal joystick on the handle being used to laterally deflect the catheter along a proximal X-Y segment and a more distal joystick of the same handle being used to laterally deflect the catheter along a more distal X'-Y' segment. These two deflections may be used to enter movement commands in a manner analogous to positioning of a robotic base using the first joystick and then articulating a wrist mounted to that base with the second joystick, with the joysticks providing either position or velocity control input to the catheter system. An input wheel with a surface that rolls along the axis of the housing can be used for entering axial elongation movement commands, and the housing may have a circumferential wheel that can be turned by the system user to help provide a desired alignment between an orientation of the housing relative to the lateral deflections of the catheter as seen in the remote imaging display. Still further alternative user interface systems may employ computer workstations such as those of known robotic catheter or robotic surgical systems, which may include one or more 3-D joysticks (optionally including an input allowing 4D, 5D, or even more degrees of freedom), housings mimicking those of mechanically steerable catheter systems, or the like. As seen in the embodiment of FIG. 8, still further optional components include a touchscreen (which may show a graphical representation of distal articulated portion 296 (one or more segments of which can be touch-selected and highlighted so that they articulate in response to movement of input 297), pushbuttons, or the like. Still further alternative user interface components may include voice control, gesture recognition, stereoscopic glasses, virtual reality displays, and/or the like.

Figure 9:
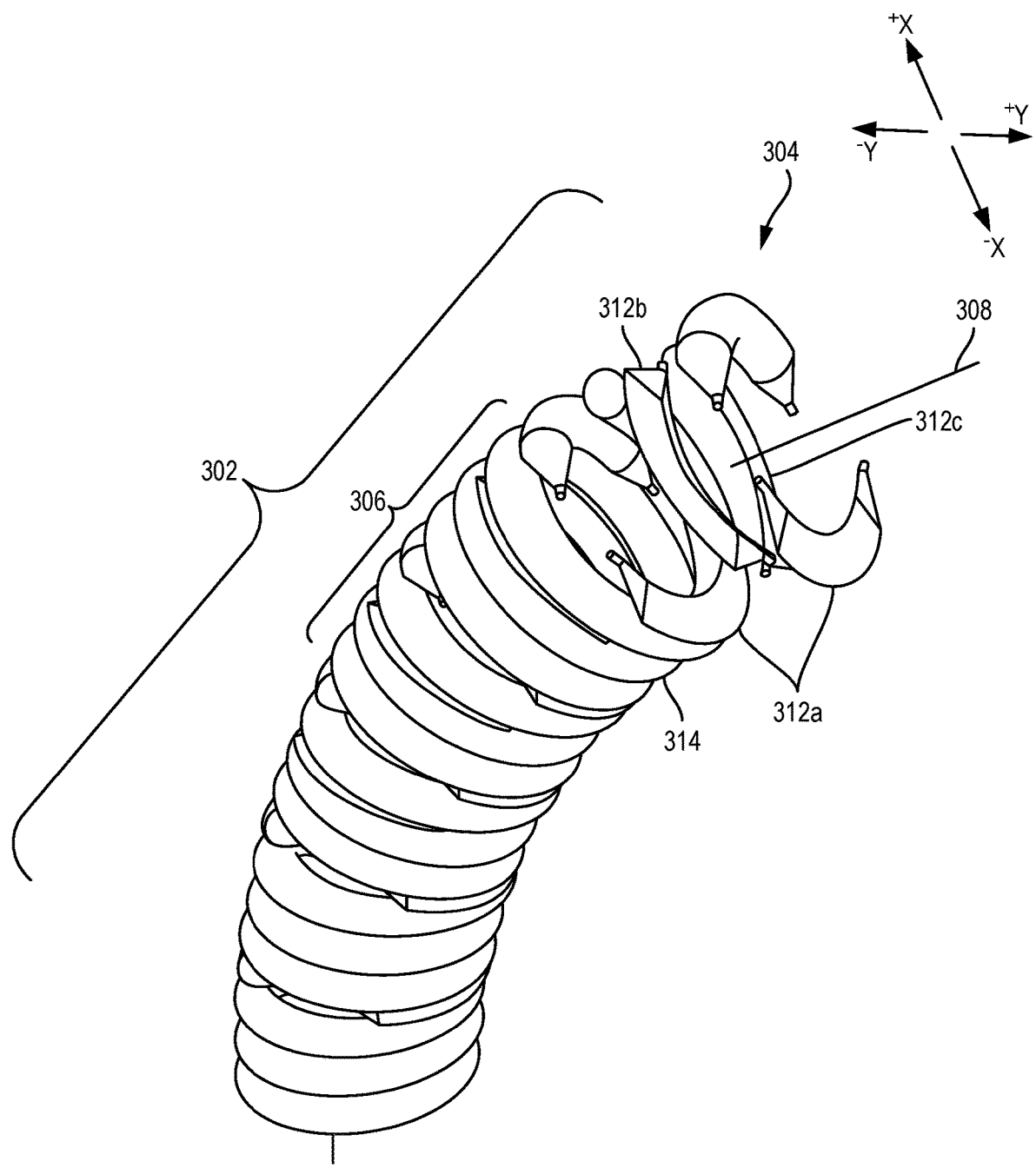
FIG. 9 shows a helical coil with inflated and uninflated balloons of a balloon array, with a distal portion of the coil removed to show the differing lateral orientations of the balloons relative to the axis of the coil.

Referring now to FIG. 9, selected components of an articulated portion 302 of an articulated catheter 304 can be seen in more detail. A plurality of inflated balloons 306 are offset from an axis 308 of catheter 304 along a first lateral orientation +X, so that the balloons urge corresponding pairs of axial (proximal and distal) surfaces on the loops of coil 310 apart. This urges the coil to bend away from inflated balloons 306 away from the +X orientation and toward the −X lateral orientation. Uninflated balloons 312a, 312b, and 312c are offset in the lateral −X, −Y, and +Y orientations, respectively, allowing selective inflations of differing subsets of these balloons to bend axis 308 in differing directions. Inflation of opposed balloons (such as −X and +X, or −Y and +Y, or both) may elongate coil 314 along axis 308. Note that a distal portion of coil 314 has been omitted from the drawing so that the arrangement of the balloons can be more clearly seen. This embodiment shows relatively standard offset balloon shapes, with the axes of the balloons bent to follow the coil. In this and other embodiments, a single balloon between coils may impose a bend in axis 308 in a range from 1 to 20 degrees, more typically being in a range from 2½ to 15 degrees, and often being from 6 to 13 degrees. To allow a single inflation lumen to achieve greater bend angles, 2, 3, 4, or more balloon inflation lumens or ports adjacent the balloons may be in fluid communication with a single common fluid inflation lumen.

Referring now to FIGS. 10A-10D, an exemplary integrated balloon array and array substrate design and fabrication process can be understood. As seen in FIGS. 10A and 10B, a cylinder 318 is defined having a diameter corresponding to a helical coil axis 320 of coil 310, with the coil axis typically corresponding to the central axis of the coil wire (so that the helical axis winds around the central axis of the elongate body). Desired balloon centerlines 322 are here defined between loops of the coil. Alternative balloon centerlines may extend along the coil axis, as can be understood with other embodiments described below. A flat pattern 324 of the balloon centerlines 322 can be unwrapped from cylinder 318, with the flat pattern optionally forming a repeating pattern extending along a helical wrap of the cylinder, the helical pattern unwrap optionally being counterwound relative to coil 310 and typically having a pitch which is greater than that of the coil. As can be understood with reference to FIGS. 10C and 10D, the repeated flat pattern 324 can be used to define a repeating substrate pattern 326, with the substrate pattern here including, for each balloon in this portion of the array, a balloon portion 328, a multi-lumen channel portion 330, and a connector portion 332 for connecting the balloon to the multi-lumen channel portion. The connector portions and balloons here extend from a single side of the multi-lumen channel portion; alternative embodiments may have connector portions and balloons extending from both lateral or circumferential sides. The loops of the substrate helix may also overlap. In other embodiments, the flat pattern (and associated substrate and multi-lumen channels) may wind in the same direction as the coil, with the balloons and channel structures optionally extending along a contiguous strip, the balloons optionally having channels along one or both axial sides of the strip and the balloons protruding radially from the strip and between the loops of the coil so that connector portions 332 may optionally be omitted. Such embodiments may benefit from a thicker and/or polymer coil. Regardless, the helical balloon array structure may facilitate lateral bending of the catheter along its axis and/or axial elongation of the catheter without kinking or damaging the substrate material along the fluid flow channels, as the substrate loops may slide relative to each other along an inner or outer surface of coil 310 (often within a sealed annular space between inner and outer sheaths bordering the inner and outer surfaces of the catheter).

Advantageously, the substrate pattern may then be formed in layers as generally described above, with at least a portion (often the majority) of each balloon being formed from sheet material in a first or balloon layer 334 (optionally by blowing at least a portion of the balloon from suitable sheet material into a balloon tool) and some or all of the channels being formed from sheet material in a second or channel layer 336. The layers can be bonded together to provide sealed fluid communication between the balloons and the other components of the fluid supply system, with the outline shapes of the balloon portions 328, connector portions 332, and channel portions being cut before bonding, after bonding, or partly before and partly after. Note that a portion of the balloon shape may be imposed on the channel layer(s) and that a plurality of channel layers may be used to facilitate fluid communication between a plurality of helically separated balloons (including balloons along a single lateral orientation of the assembled catheter) and a common fluid supply channel. Similarly, a portion (or even all) of the channel structure might alternatively be imposed on the balloon layer, so that a wide variety of architectures are possible. Formation of multiple balloons 334 and channels 330, and bonding of the layers can be performed using parallel or batch processing (with, for example, tooling to simultaneously blow some or all of the balloons for a helical balloon array of an articulation sub-portion, a laser micro-machining station that cuts multiple parallel channels, simultaneous deposition of adhesive materials around multiple balloons and channels), or sequentially (with, for example, rolling tooling and/or roll-by stations for balloon blowing, laser cutting, or adhesive applying tooling), or a combination of both. The number of balloons included in a single helical substrate pattern may vary (typically being from 4 to 80, and optionally being from 4 to 32, and often being from 8 to 24). The balloons may be spaced for positioning along a single lateral catheter bending orientations, along two opposed orientations, along three orientations, along four orientations (as shown), or the like. Channel portion 330 may terminate at (or be integrated with) an interface with a multi-channel cable 334 that extends proximally along the coil (and optionally along other proximal balloon array portions formed using similar or differing repeating balloon substrate patterns). A wide variety of alternative balloon shapes and balloon fabrication techniques may be employed, including blowing a major balloon portion from a first sheet material and a minor portion from a second sheet material, and bonding the sheets surrounding the blow portions together with the bond axially oriented (as shown in FIG. 10) so that the sheets and substrate layers are oriented along a cylinder bordering the coil, or with the bond radially oriented so that the sheet material adjacent the bonds is connected to adjacent substrate by a bent connector portion or tab.

Figures 11A, 11B:
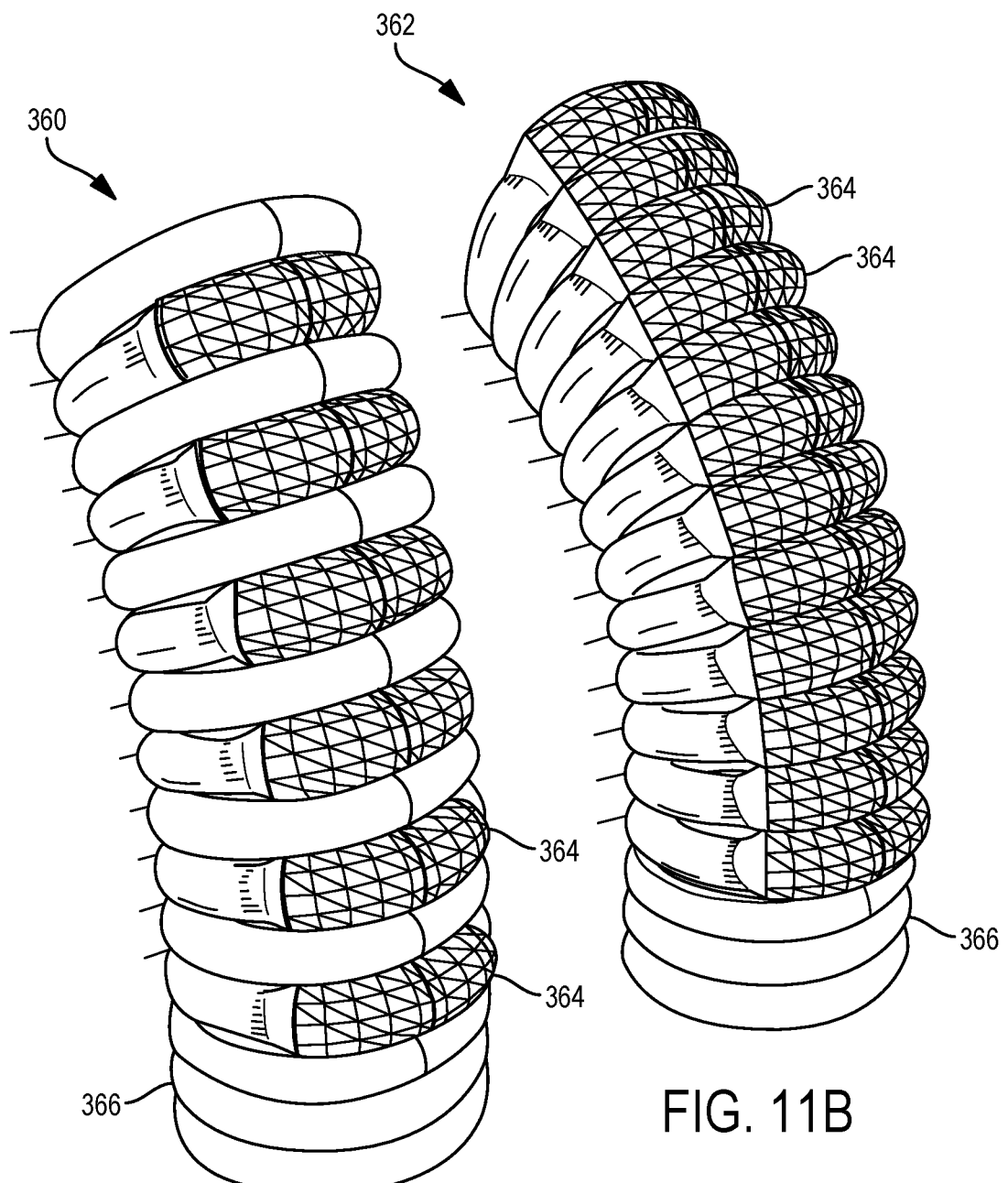
FIGS. 11A and 11B schematically illustrate balloon arrays in which the balloons are disposed over multi-lumen helical coil cores shafts or conduits, and also show the effects of varying balloon inflation density on a radius of curvature of a catheter or other flexible body.

Referring now to FIGS. 11A and 11B, an alternative coaxial balloon/coil arrangement can be understood. In these embodiments, balloons 364 are mounted over a coil 366, with a plurality of the balloons typically being formed from a continuous tube of material that extends along the helical axis of the coil (see helical axis 320 of FIG. 10A). The balloon material will generally have a diameter that varies locally, with the balloons being formed from locally larger diameter regions of the tube, and the balloons being separated by sealing engagement between the tube material and coil therein at locally smaller diameters of the tube. The variation in diameter may be formed by locally blowing the balloons outward from an initial tube diameter, by locally heat-shrinking and/or axially stretching the tube down from an initial tube diameter, or both, and adhesive or heat-bonding between the tube and coil core therein may enhance sealing. In alternative embodiments, metal rings may be crimped around the tubular balloon material to affix (and optionally seal) the tube to the underlying helical coil, with the rings and crimping optionally employing marker band structures and associated techniques. Some or even all of the variation in diameter of the balloon material along the coil may be imposed by the crimped rings, though selective heat shrinking and/or blowing of the balloons and/or laser thermal bonding of the balloon to the coil may be combined with the crimps to provide the desired balloon shape and sealing. Regardless, fluid communication between the inner volume of the balloon (between the balloon wall and the coil core) may be provided through a radial port to an associated lumen within the coil core. As can be understood with reference to coil assembly 360 of FIG. 11A, the balloons may have outer surface shapes similar to those described above, and may similarly be aligned along one or more lateral bending orientations. As can be understood with reference to assemblies 360 and 362 of FIGS. 11A and 11B, bend angles and radii of curvature of the catheter adjacent the balloon arrays may be determined by an axial spacing (and/or number of loops) between balloons, and/or by selective inflation of a subset of balloons (such as by inflating every other balloon aligned along a particular lateral axis, every third aligned balloon, every forth aligned balloon, and so on).

Figure 12:
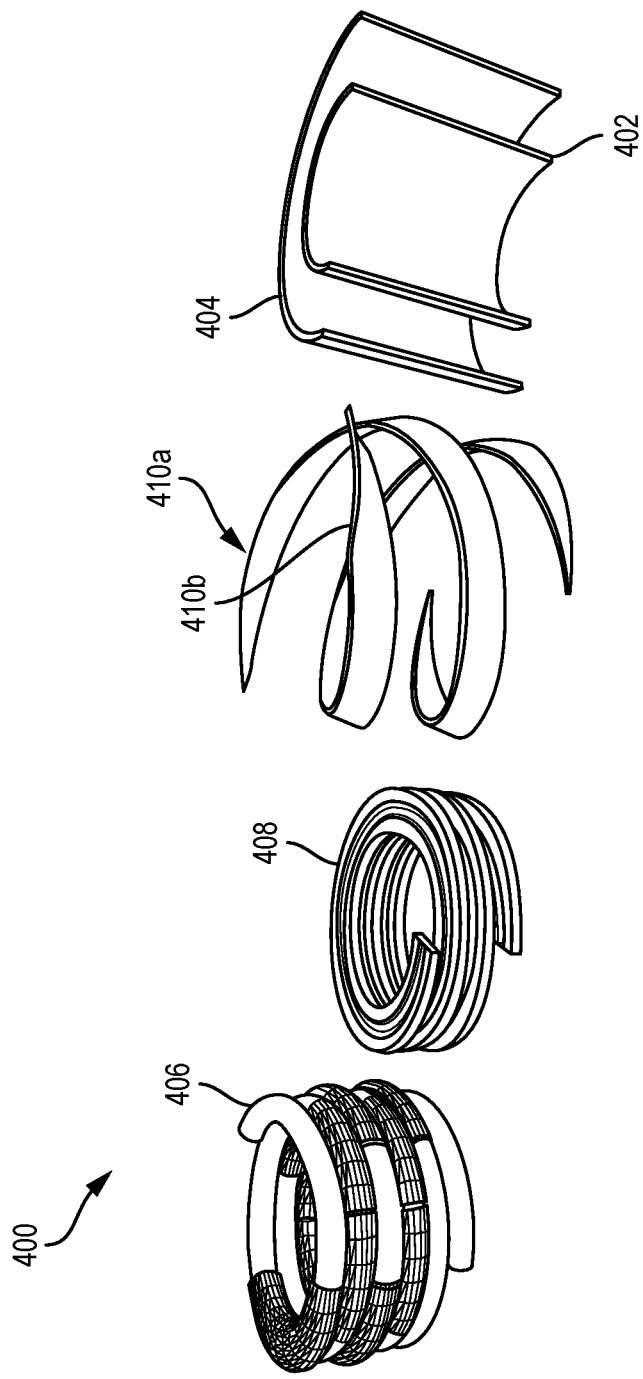
FIG. 12 is an exploded view of components that may be included in an articulated segment of an elongate articulated body, with the components laterally offset from their assembled position.

Referring now to FIG. 12, separation of functionality among exemplary catheter components can be understood with reference to an exploded assembly 400, which shows an axial portion of an articulated catheter, the components here being laterally displaced from each other (and from their assembled coaxial positioning). The fluid-containing components of this portion are preferably contained between an inner sheath 402 and an outer sheath 404, with these sheaths being sealed to each other proximally and distally of the balloon array (or of some portion of the array). By drawing a vacuum between the sealed inner and outer sheaths (optionally using a simple positive syringe pump or the like) and by monitoring of the vacuum with a pressure sensing circuit coupled to a fluid supply shut off-valve, integrity of the fluid transmission and drive components within the patient body can be ensured, and inadvertent release of drive fluid within the patient can be inhibited.

Still referring to FIG. 12, a coaxial helical coil/balloon assembly 406 is disposed radially between the inner and outer sheaths 402, 404. The inner and/or outer sheaths may be configured so as to enhance radial strength and axial flexibility, such as by including circumferential fibers (optionally in the form of a polymer or metallic braid, loops, or windings), axial corrugations, or the like. As described above, balloons of assembly 406 are mounted to a helical core along a helical axis. At least one lumen extends along the helical core and allows the balloons on the core to be inflated and deflated. To help maintain axial alignment of the loops of assembly 406 an alignment spacer coil 408 is interleaved between the assembly loops. Spacer coil 408 has opposed surfaces with indented features so that axial compressive forces (from the environment or inflation of the balloons) squeezes the alignment spacer and keeps the assembly balloons and adjacent loops from being pushed radially out of axial alignment. Note that compression between loops of assembly 406 may be imposed by the coil, by the spacer, by the inner and/or outer sheath, by a pullwire, or by a combination of two or more of these. Note also that alternative embodiments may replace the balloons mounted on the coil with balloons between loops of the coil coupled with a layered array substrate such as those shown in FIGS. 10C and 10D, optionally with a pair of alignment spacer coils on either axial surface of the balloons (and hence between the balloons and the coil). Still further alternatives include multiple interleaved coil/balloon assemblies, and/or other components and arrangements described herein.

As there may be a large total number of balloons in the overall balloon array of some embodiments, and as those arrays may be separated axially into articulated sub-portions of an overall catheter (or other articulated elongate body), and as the available space within the coil core of coil/balloon assembly 406 may be limited, it may be advantageous to have one or more separate structures extending axially within the annular space between inner and outer sheaths 402, 404. Those separate structures can have additional fluid inflation channels that are separate from the fluid inflation channels of the coil/balloon assembly or assemblies, and that can be used for inflating balloon articulation arrays that are mounted distally of the coil/balloon assembly 406. Toward that end, thin flat multi-lumen helical cable structures 410a, 410b may be disposed in the space radially between the coil/balloon assembly 406 and outer sheath 404, and/or between the coil/balloon assembly and inner sheath 402. Cables 410 may comprise a series of small diameter tubular structures (optionally comprising PET or fused silica with appropriate cladding) which may or may not be affixed together and are in a side-by-side alignment, a multichannel structure formed by micromachining and bonding layers (as described above), a multi-lumen extrusion having an elongate cross-section, or the like. Each cable 410a, 410b of a particular axial segment may be coupled to a core of a coil/balloon assembly for a more distal articulated axial segment. A helical or serpentine configuration of the cables may facilitate axial bending and/or elongation without stressing the cables, and the number of cables along an articulation segment may range from 0 (particularly along a distal articulation segment) to 10. Note that a number of alternative arrangements are also possible, including separating the cables from the coil/balloon assembly with an intermediate sheath, enhancing flexibility by using a number of separate fused silica tubes without bundling subsets of the tubes into cables, and the like. One or more stiffening balloons may be incorporated into the cable structure, with the stiffening balloons of each segment optionally being in fluid communication with a common supply lumen, and optionally with a common supply lumen for one, some, or all other segments. The stiffening balloon may comprises a tubular material disposed around a multi-lumen cable extrusion, and may be inflated using a port within the tube into a selected lumen of the extrusion. The stiffening balloon tube may be sealed to the cable extrusion or the like proximally and distally of the port, and may have an expandable length sufficient to extend along some or all of an axial articulation segment or sub-portion. The cables may be omitted, particularly where the core along a single segment can encompass sufficient channels for the desired degrees of freedom of the catheter.

Figure 13:
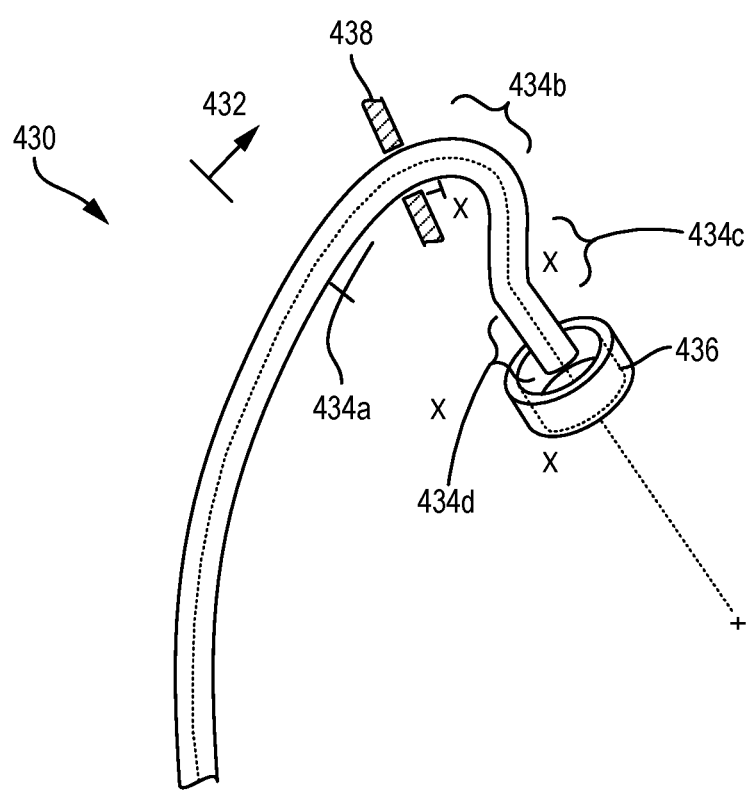
FIG. 13 schematically illustrates bending of a diagnosis or treatment delivery catheter into alignment with a target tissue by actuating a plurality of articulation sub-portions or segments of the catheter.

Referring now to FIG. 13, an exemplary catheter 430 has an articulated portion 432 that includes a plurality of axially separate articulated segments or sub-portions 434a, 434b, 434c, and 434d. Generally, the plurality of articulation segments may be configured to facilitate aligning a distal end of the catheter with a target tissue 436. Suitable articulation segments may depend on the target tissue and planned procedure. For example, in this embodiment the articulation segments are configured to accurately align a distal end of the catheter with the angle and axial location of the native valve tissue, preferably for any patient among a selected population of patients. More specifically, the catheter is configured for aligning the catheter axis at the distal end of the catheter with (and particularly parallel to) an axis of the target tissue, and (as measured along the axis of the catheter) for axially aligning the end of the catheter with the target tissue. Such alignment may be particularly beneficial, for example, for positioning a prosthetic cardiac valve (optionally an aortic valve, pulmonary valve, or the like, and particularly a mitral valve) with tissues of or adjacent a diseased native valve. Suitable catheter articulation capabilities may also, in part, depend on the access path to the target tissue. For alignment with the mitral valve, the catheter may, for example, be advanced distally into the right atrium via the superior or inferior vena cava, and may penetrate from the right atrium through the septum 438 into the left atrium. Suitable transceptal access may be accomplished using known catheter systems and techniques (though alternative septal traversing tools using the articulated structures described herein might alternatively be used). Regardless, to achieve the desired alignment with the native valve tissue, the catheter may be configured to, for example: 1) from distally of (or near) the septum, form a very roughly 90 degree bend (+/− a sufficient angle so as to accommodate varying physiologies of the patients in the population); 2) extend a distance in desired range in three dimensions, including a) apically from the septal penetration site and b) away from the plane of the septal wall at the penetration; and 3) orient the axis of the catheter at the distal end in three dimensions and into alignment with the native valve tissue.

To achieve the desired alignment, catheter 430 may optionally provide consistent multi-axis bend capabilities as well as axial elongation capabilities, either continuously along the majority of articulatable portion 432 of catheter 430, or in articulated segments at regular intervals extending therealong. Alternative approaches may employ more functionally distinguished articulation segments. When present, each segment may optionally have between 4 and 32 balloons, subsets of the balloons within that segment optionally being oriented along from 1 to 4 lateral orientations. In some embodiments, the axis bending balloons within at least one segment may all be aligned along a single bend orientation, and may be served by a single inflation lumen, often served by a modulated fluid supply that directs a controlled inflation fluid volume or pressure to the balloons of the segment to control the amount of bending in the associated orientation. Alternative single lateral bending direction segments may have multiple sets of balloons served by different lumens, as described above. For example, segments 434a and 434b may both comprise single direction bending segments, each capable of imposing up to 60 degrees of bend angle and with the former having a first, relatively large bend radius in the illustrated configuration due to every-other axial balloon being inflated (as can be understood with reference to FIG. 11A) or due to inflation with a limited quantity of inflation fluid. In segment 434b, all but the distal-most four balloons may be inflated, resulting in a smaller bend radius positioned adjacent segment 434a, with a relatively straight section of the catheter distal of the bend. Segment 434c may have balloons with four different bend orientations at a relatively high axial density, here having selected transverse balloons (such as 6+X balloons and 2−Y balloons) inflated so as to urge the catheter to assume a shape with a first bend component away from the septal plane and a second bend component laterally away from the plane of the bends of segments 434a and 434b. Segment 434d may comprise an axial elongation segment, with opposed balloons in fluid communication with the one or more inflation fluid supply lumen of this segment. Axial positioning of the end of the catheter may thus be accurately controlled (within the range of motion of the segment) by appropriate transmission of inflation fluid. Advantageously, such specialized segments may limit the number of fluid channels (and the cost, complexity and/or size of the catheter) needed to achieve a desired number of degrees of freedom and a desired spatial resolution. It should be understood that alternative segment arrangements might be employed for delivery of a prosthetic heart valve or the like, including the use of three segments. The valve might be positioned using a three-segment system by, for example, inserting the catheter so that the septum is positioned along the middle of the three segments, ideally with the catheter traversing the septum at or near the middle of the middle segment.

Figure 14A:
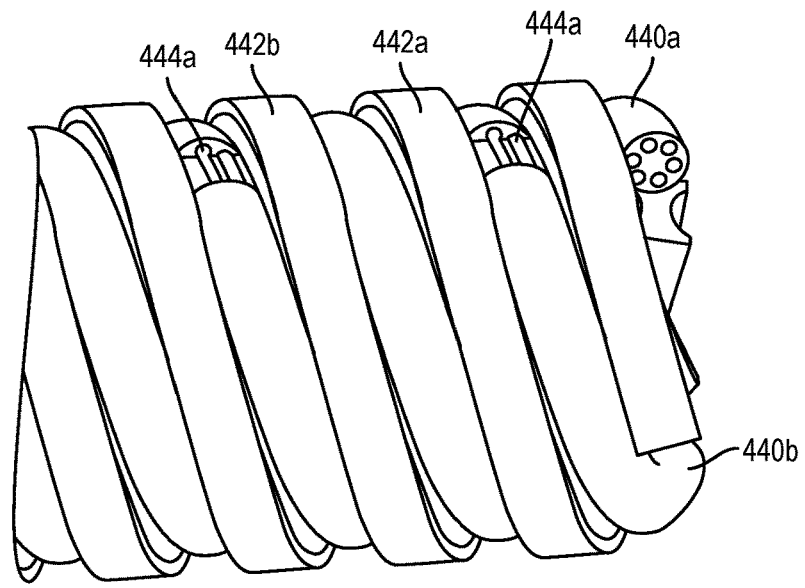
FIGS. 14A-14C illustrate components of an alternative embodiment having a plurality of interleaved multi-lumen polymer helical cores interleaved with a plurality of resilient coil structures having axially oriented surfaces configured to radially restrain the balloons.
Figure 14B:
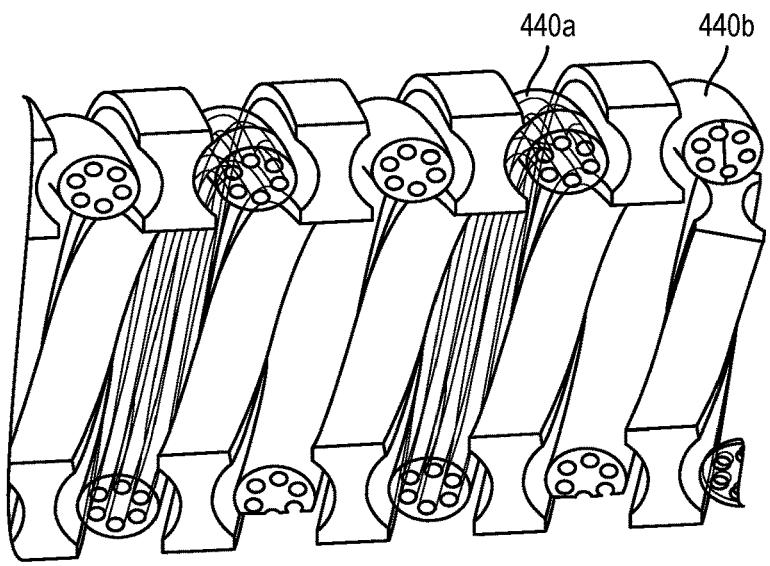
Figure 14C:
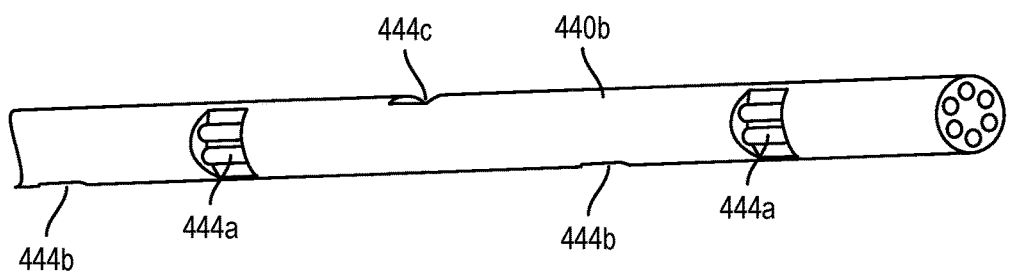

Referring now to FIGS. 14A-14C, a still further embodiment of an articulated catheter includes first and second interleaved helical multi-lumen balloon fluid supply/support structures 440a, 440b, along with first and second resilient helical coils 442a, 442b. In this embodiment, a series of balloons (not shown) are mounted around each of the multi-lumen structures, with the balloons spaced so as to be aligned along three lateral bending orientations that are offset from each other around the axis of the catheter by 120 degrees. Six lumens are provided in each multi-lumen structure, 440a, 440b, with one dedicated inflation lumen and one dedicated deflation lumen for each of the three lateral bending orientations. Radial fluid communication ports between the lumens and associated balloons may be provided by through cuts through pairs of the lumens.

By spacing the cuts 444a, 444b, 444c, as shown, and by mounting balloons over the cuts, the inflation and deflation lumens can be used to inflate and deflate a subset of balloons aligned along each of the three bending orientations. Advantageously, a first articulated segment having such a structure can allow bending of the catheter axis in any combination of the three bend orientations by inflating a desired subset of the balloons along that segment. Optionally, the bend angle for that subset may be controlled by the quantity and/or pressure of fluid transmitted to the balloons using the 6 lumens of just one multi-lumen structure (for example, 440a), allowing the segment to function in a manner analogous to a robotic wrist. Another segment of the catheter axially offset from the first segment can have a similar arrangement of balloons that are supplied by the 6 lumens of the other multi-lumen structure (in our example, 440b), allowing the catheter to position and orient the end of the catheter with flexibility analogous to that of a serial wrist robotic manipulators. In other embodiments, at least some of the balloons supplied by the two multi-lumen structures may axially overlap, for example, to allow increasing bend angles and/or decreasing bend radii by combining inflation of overlapping subsets of the balloons. Note also that a single lumen may be used for both inflation and deflation of the balloons, and that multi-lumen structures of more than 6 lumens may be provided, so that still further combinations these degrees of freedom may be employed.

In the embodiment illustrated in the side view of FIG. 14A and in the cross-section of FIG. 14B, the outer diameter of the helical coils is about 0.130 inches. Multi-lumen structures 440a, 440b have outer diameters in a range from about 0.020 inches to about 0.030 inches (optionally being about 0.027 inches), with the lumens having inner diameters of about 0.004 inches and the walls around each lumen having a minimum thickness of 0.004 inches. Despite the use of inflation pressures of 20 atm or more, the small diameters of the lumens help limit the strain on the helical core structures, which typically comprise polymer, ideally being extruded. Rather than including a resilient wire or the like in the multi-lumen structure, axial compression of the balloons (and straightening of the catheter axis after deflation) is provided primarily by use of a metal in coils 442a, 442b. Opposed concave axial surfaces of coils 442 help maintain radial positioning of the balloons and multi-lumen structures between the coils. Affixing the ends of resilient coils 442 and balloon supply/support structures 440 together to the inner and outer sheaths at the ends of the coils, and optionally between segments may help maintain the helical shapes as well. Increasing the axial thickness of coils 442 and the depth of the concave surfaces may also be beneficial to help maintain alignment, with the coils then optionally comprising polymer structures. Still other helical-maintaining structures may be included in most or all of the helical embodiments described herein, including periodic structures that are affixed to coils 442 or other helical skeleton members, the periodic structures having protrusions that extend between balloons and can engage the ends of the inflated balloon walls to maintain or index lateral balloon orientations.

Many of the embodiments described herein provide fluid-driven articulation of catheters, guidewires, and other elongate flexible bodies. Advantageously, such fluid driven articulation can rely on very simple (and small cross-section) fluid transmission along the elongate body, with most of the forces being applied to the working end of the elongate body reacting locally against the surrounding environment rather than being transmitted back to a proximal handle or the like. This may provide a significant increase in accuracy of articulation, decrease in hysteresis, as well as a simpler and lower cost articulation system, particularly when a large number of degrees of freedom are to be included. Note that the presence of relatively high pressure fluid, and/or low temperature fluid, and/or electrical circuitry adjacent the distal end of an elongate flexible body may also be used to enhance the functionality of tools carried by the body, particularly by improving or adding diagnostic tools, therapeutic tools, imaging or navigations tools, or the like.

Figure 15:
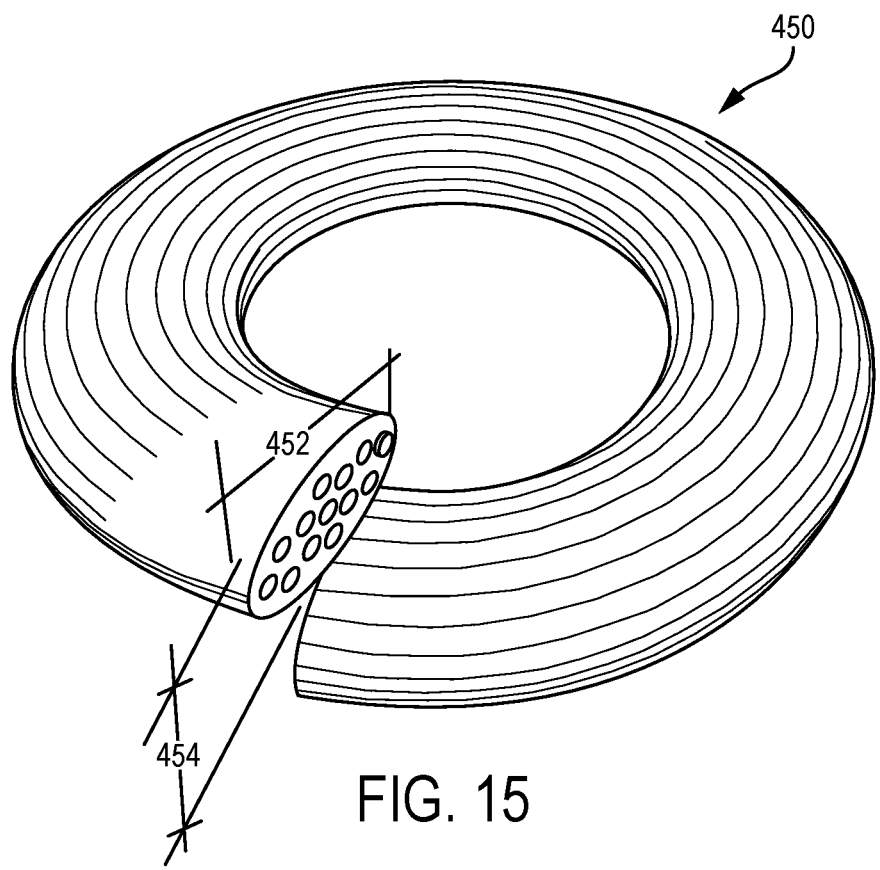
FIG. 15 is a perspective view of an alternative helical balloon core having a radially elongate cross-section to limit inflation fluid flows and provide additional fluid channels and/or channel sizes.

Referring now to FIG. 15, a radially elongate polymer helical balloon core structure 450 generally has a cross section with a radial thickness 452 that is significantly greater than its axial thickness 454. Radial thickness 452 may optionally be, for example 80% or more of the inflated diameter of the surrounding balloon, while axial thickness 454 may be between 20% and 75% of the inflated diameter. As compared to a circular core cross-section, such an elongate cross-section provides additional territory for balloon lumens extending within the coil core (allowing more lumens and separately inflatable balloons or groups of balloons, and/or allowing larger lumen sizes for faster actuation times) with the same the axial actuation stroke of the surrounding balloon. The exemplary cross-sectional shapes include elliptical or other continuously curved shapes to facilitate sealing engagement with the surrounding balloon wall material, with an alternative having proximal and distal regions with circular curvatures corresponding to those of the inflated balloon (so as to enhance axially compressive force transmission against an axially indented coil spring surface configured to evenly engage the inflated balloon).

Figure 16:
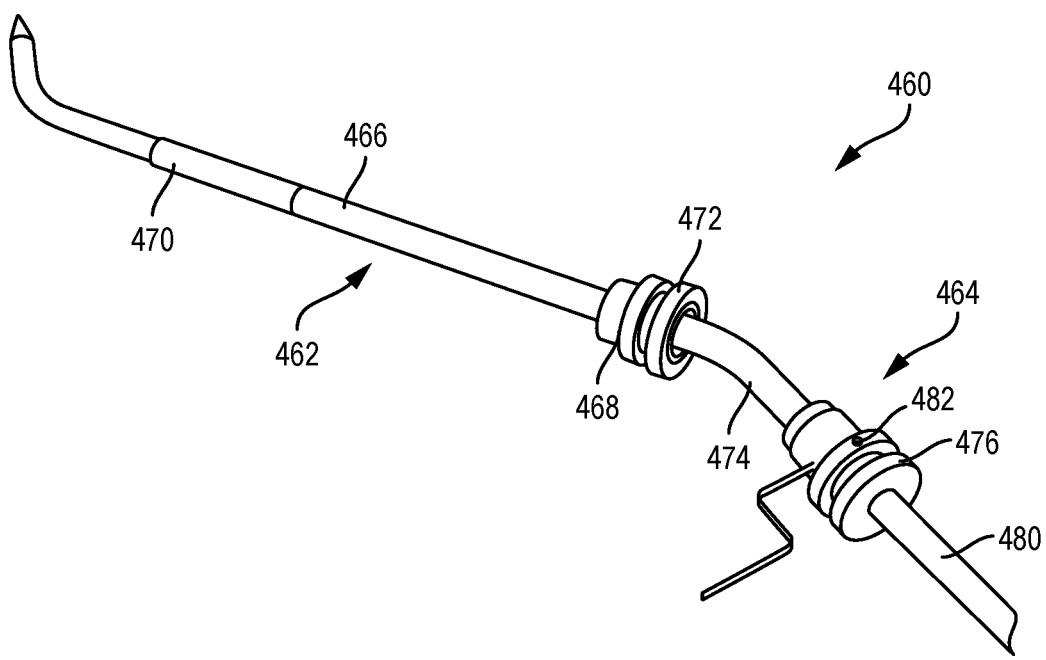
FIG. 16 is a perspective view showing an exemplary introducer sheath/input assembly having a flexible joystick for receiving movement commands using relative movement between hands or fingers of a user.

Referring now to FIG. 16, a perspective view of an exemplary introducer sheath/input assembly for use in the systems of FIGS. 1 and 8 can be seen in more detail. Introducer/input assembly 460 generally includes an introducer sheath assembly 462 and an input assembly 464. Introducer 462 includes an elongate introducer sheath 466 having a proximal end 468 and a distal end 470 with an axial lumen extending therebetween. A proximal housing 472 of introducer 462 contains an introducer hemostasis valve. Input 464 includes a flexible joystick shaft 474 having a distal end slidably extending into the lumen of introducer housing 472, and a proximal end affixed to an input housing 476 containing an input valve. A lumen extends axially through input 464, and an articulatable catheter 480 can be advanced through both lumens of assembly 460. A cable or other data communication structure of assembly 460 transmits movement commands from the assembly to a processor of the catheter system so as to induce articulation of the catheter within the patient. More specifically, when the catheter system is in a driven articulation mode, and a clutch input 482 of introducer/input assembly 460 is actuated, movement of input housing 476 relative to sheath housing 472 induces articulation of one or more articulatable segment of catheter 480 near the distal end of the catheter, with the catheter preferably having any one or more of the articulation structures described herein. The valves within the housings of introducer/input assembly may be actuated independently to axially affix catheter 480 to introducer 462, and/or to input 464.

Figure 17A:
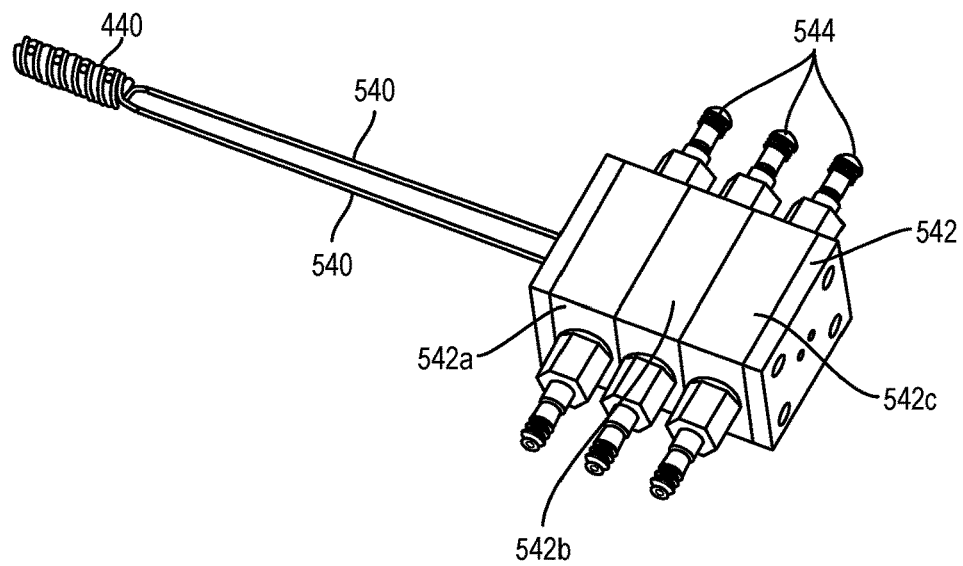
FIGS. 17A and 17B are a perspective view and a cross-section of components of a catheter and fluid supply manifold system.
Figure 17B:
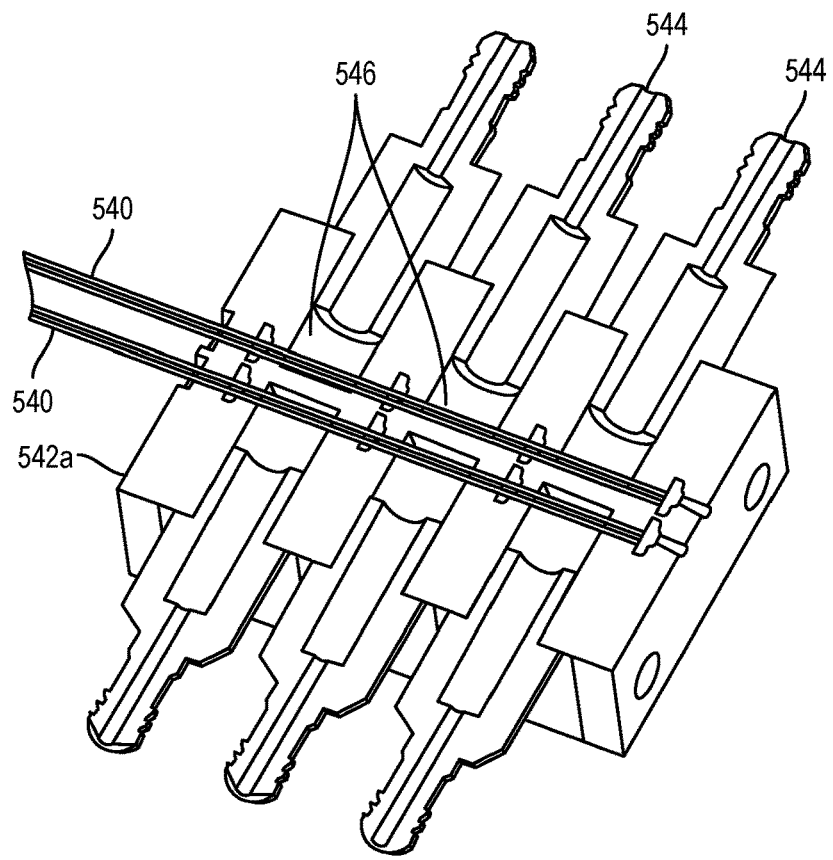

Referring now to FIGS. 17A and 17B, articulation system components related to those of FIGS. 14A-14C can be seen. Two multi-lumen polymer helical cores 440 can be interleaved with axially concave helical springs along the articulated portion of a catheter. Curved transition zones extend proximal of the helical cores to axially straight multi-lumen extensions 540, which may extend along a passive (unarticulated) or differently articulated section of the catheter, or which may extend through articulated segments that are driven by fluid transmitted by other structures (not shown). Advantageously, a portion of each proximal extension 540 near the proximal end can be used as a proximal interface 550 (See FIG. 17C), often by employing an axial series of lateral ports formed through the outer walls of the multi-lumen shaft into the various lumens of the core. This proximal interface 550 can be mated with a receptacle 552 of a modular valve assembly 542, or with a receptacle of non-modular valve assembly, or with a connector or interface body that couples to a manifold so as to provide sealed, independently controlled fluid communication and a controlled flow of inflation fluid to desired subsets of the balloons from a pressurized inflation fluid source, along with a controlled flow of exhaust fluid from the balloons to the atmosphere or an exhaust fluid reservoir.

Extensions 540 extend proximally into a valve assembly 542 so as to provide fluid communication between fluid pathways of the valve assembly and the balloons of the articulated segment. Valve assembly 542 includes an axial series of modular valve units 542a, 542b, 542c, etc. Endplates and bolts seal fluid paths within the valve assembly and hold the units in place. Each valve unit of assembly 542 includes at least one fluid control valve 544, and preferably two or more valves. The valves may comprise pressure modulating valves that sense and control pressure, gate valves, three-way valves (to allow inflation fluid along a channel to one or more associated balloons, to seal inflation fluid in the inflation channel and associated balloons while flow from the fluid source is blocked, and to allow inflation fluid from the channels and balloons to be released), fluid dispersing valves, or the like. O-rings provide sealing between the valves and around the extensions 540, and unthreading the bolts may release pressure on the O-rings and allow the extensions to be pulled distally from the valve assembly, thereby providing a simple quick-disconnect capability. Radial ports 546 are axially spaced along extensions 540 to provide fluid communication between the valves and associated lumens of the multi-lumen polymer extensions, transitions, and helical coils. Advantageously, where a greater or lesser number of inflation channels will be employed, more or fewer valve units may be axially stacked together. While valves 544 are here illustrated with external fluid tubing connectors (to be coupled to the fluid source or the like), the fluid paths to the valves may alternatively also be included within the modular valve units, for example, with the fluid supply being transmitted to each of the valves along a header lumen that extends axially along the assembly and that is sealed between the valve units using additional O-rings or the like. Note that while modular units 542a, 542b, . . . may comprise valves, in alternative embodiments these units may simply comprise ferrules, posts, or other interface structures that allow the assembly to be used as a connector or interface body that helps provide fluid communication between the multi-lumen shaft or core and some of the components of the fluid supply system.

Figure 17C:
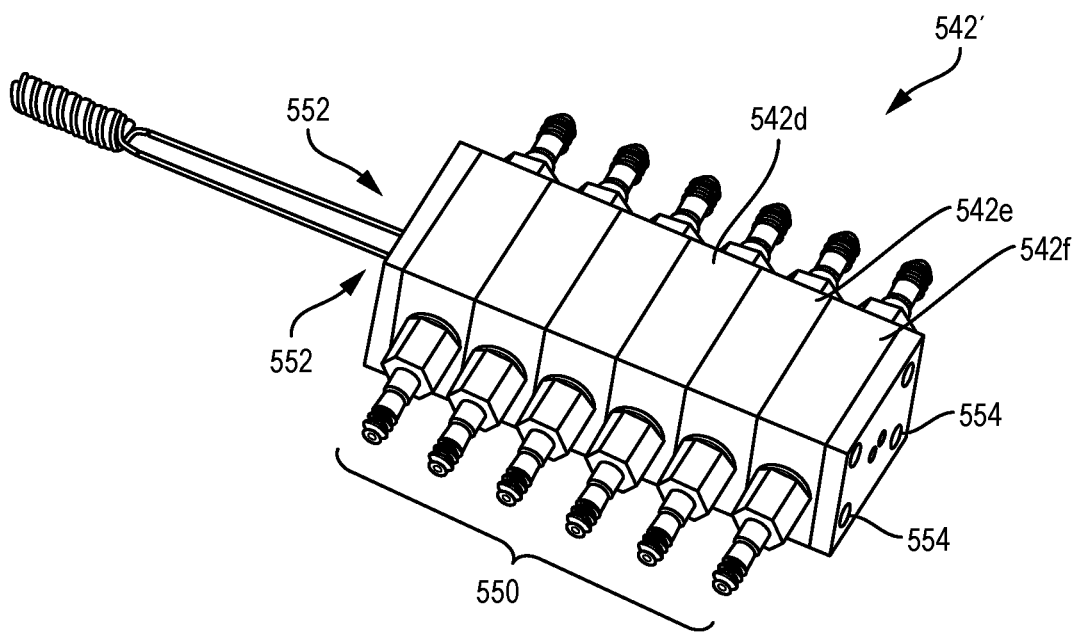
FIG. 17C is a perspective view of a fluid supply manifold having components similar to those of FIGS. 17A and 17B, showing how additional interchangeable modules can be included in the manifold assembly for controlling fluid systems having greater numbers of fluid channels.

Referring now to FIG. 17C, additional modular valve units 542d, 542e, and 542f are included in the valve and manifold assembly 542' so as facilitate independent control of inflation fluid flows to and from lumens of the multi-lumen cores. The modular valve units are preferably interchangeable, and will often include electrical circuitry and a pressure sensor for each inflation lumen, along with the valves, plate structures, and channels. The electrical circuitry for each plate will often be supported by a flex circuit substrate and may optionally be adhesively bonded to one of the major surfaces of the plates, or it may be between layers of the plate or held compressively between plates. Along with conductive traces for communication between the valves, sensors, and system processor, the flex circuit may also support electronics to facilitate multiplexing among the plate modules, plug-and-play plate module capabilities, daisy chaining or networking of the plate modules, and/or the like. In exemplary embodiments described below, the flex circuits substrate may also support (and help provide electrical coupling with MEMS valves and/or MEMS pressure sensors. The flex circuit substrate or another film substrate material may optionally help support O-rings, gaskets, or other seal materials surrounding passages through the plates (or layers thereof), including passages that form receptacles 552, inflation headers, deflation headers, and the like; though some or all of the seals for these structures may instead be independently positioned. As noted above, one or more quick-disconnect fitting 554 may be configured to help seal the ports of the multi-lumen shaft (or of an intermediate body) to the fluid channels of the plates. Where the ports are included on a shaft that extends through the plates, the quick-disconnect fitting may take the form of a compression member that is manually movable between a detachable configuration (in which little or no compression is applied between plates) and a sealed configuration (in which sufficient compression is applied between plates to squeeze seal material from between the plates of the stack and against the shafts). The quick-disconnect fitting may comprise one or more over-center latch, one or more threaded connector, one or more cam unit, or the like.

Figure 18A:
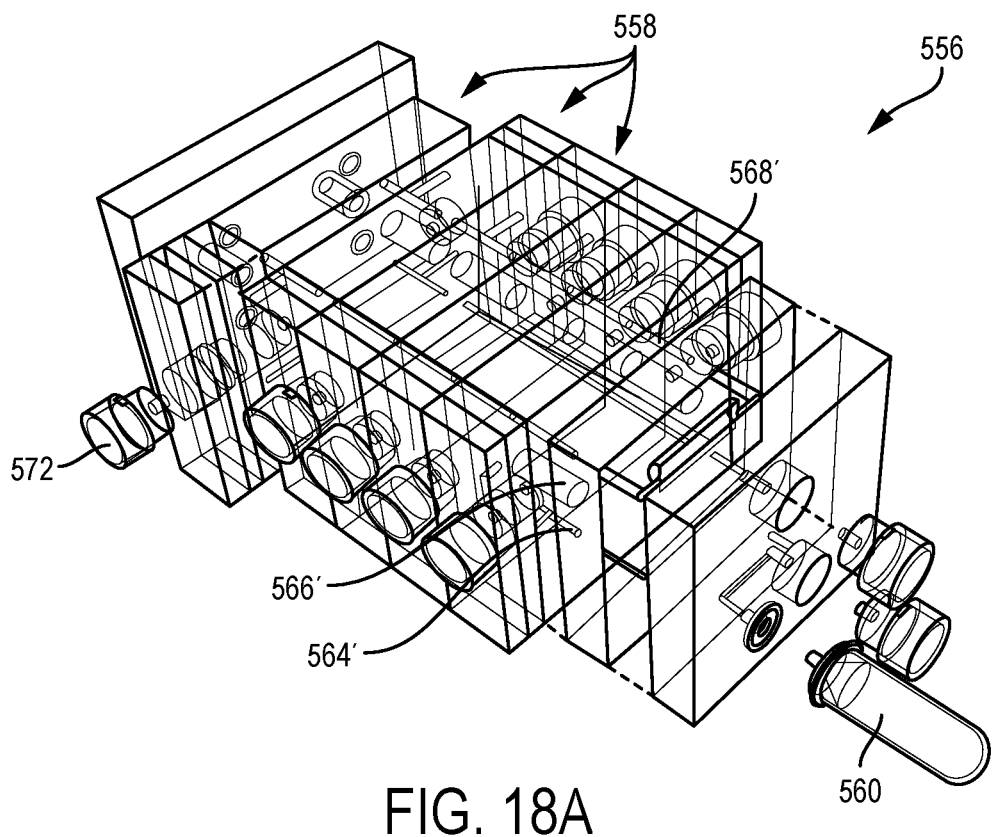
Figure 18:
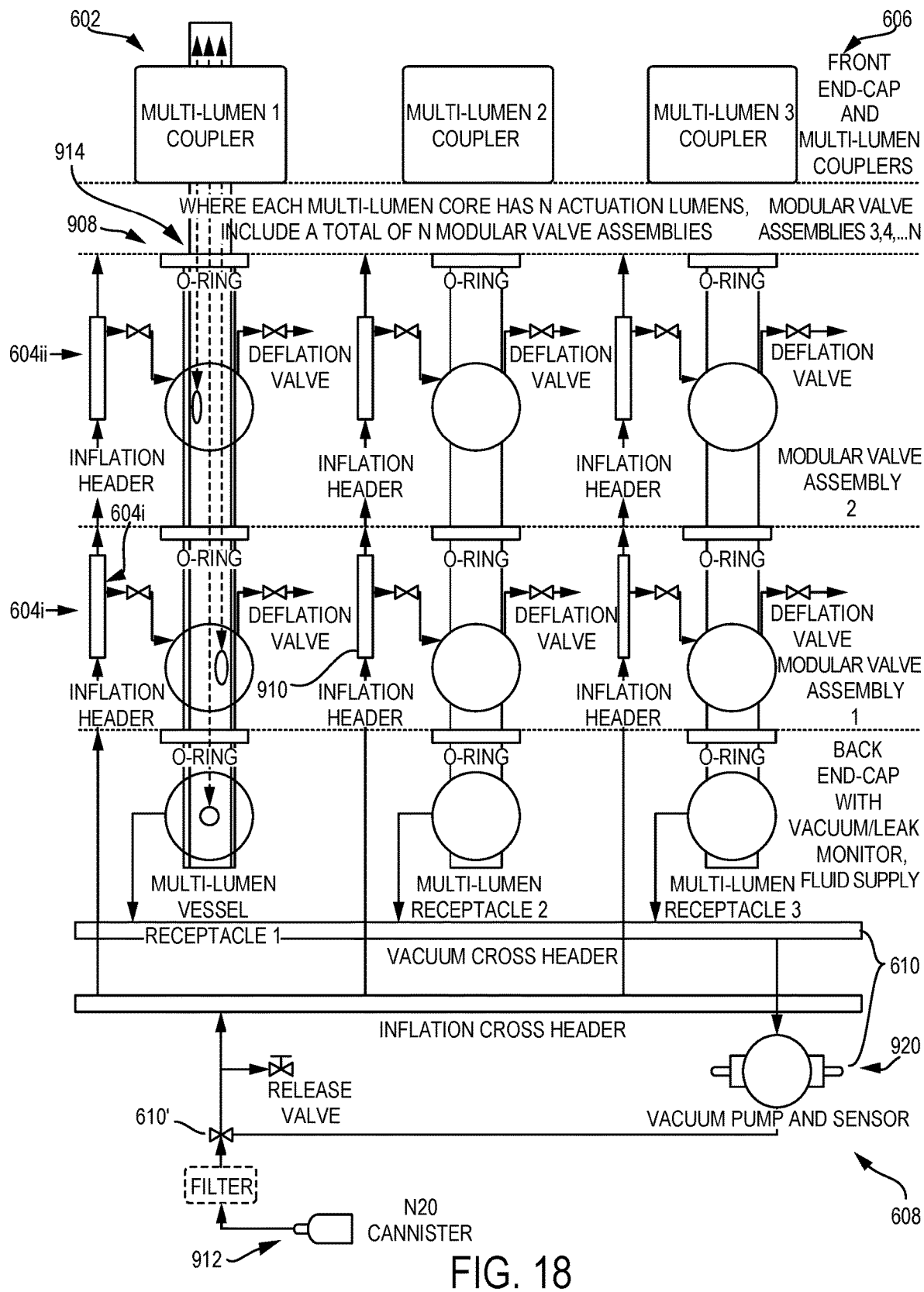
FIG. 18 is a simplified schematic of a modular manifold having a stack of valve plate assemblies through which a multi-lumen connector extends so as to provide controlled fluid flow to and from balloons of an array.

Referring now to FIG. 18, a simplified manifold schematic shows fluid supply and control components of an alternative manifold 602. As generally described above, manifold 602 has a plurality of modular manifold units or valve assembly plates 604i, 604ii, . . . stacked in an array. The stack of valve plates are sandwiched between a front end cap 606 and a back end-cap 608, and during use the proximal portion of the multi-lumen conduit core(s) extend through apertures in the front cap and valve plates so that the proximal end of the core is adjacent to or in the back cap, with the apertures defining a multi-lumen core receptacle. The number of manifold units or modules in the stack is sufficient to include a plate module for each lumen of each of the multi-lumen core(s). For example, where an articulatable structure has 3 multi-lumen core shafts and each shaft has 6 lumens, the manifold assembly may include a stack of 6 plates. Each plate optionally includes an inflation valve and a deflation valve to control pressure in one of the lumens (and the balloons that are in communication with that lumen) for each multi-lumen shaft. In our 3-multi-lumen shaft/6 lumen each example, each plate may include 3 inflation valves (one for a particular lumen of each shaft) and 3 deflation valves (one for that same lumen of each shaft). As can be understood with reference to the multi-lumen shaft shown in receptacle 1 of FIG. 18, the spacing between the ports along the shaft corresponds to the spacing between the fluid channels along the receptacle. By inserting the core shaft fully into the multi-lumen shaft receptacle, the plate channel locations can be registered axially with the core, and with the ports that were drilled radially from the outer surface of the multi-lumen core. The processor can map the axial locations of the valves along the receptacle with the axial locations of the ports along the core shafts, so that a port into a particular lumen of the core can be registered and associated with a fluid channel of specific inflation and deflation valves. One or more inflation headers can be defined by passages axially through the valve-unit plates; a similar deflation header (not shown) can also be provided to monitor pressure and quantity of fluid released from the lumen system of the articulated device. O-rings can be provided adjacent the interface between the plates surrounding the headers and receptacles. Pressure sensors (not shown) can monitor pressure at the interface between each plate and the multi-lumen receptacle.

Along with monitoring and controlling inflation and deflation of all the balloons, manifold 602 can also include a vacuum monitor system 610 to verify that no inflation fluid is leaking from the articulated system within the patient body. A simple vacuum pump (such as a syringe pump with a latch or the like) can apply a vacuum to an internal volume or chamber of the articulated body surrounding the balloon array. Alternative vacuum sources might include a standard operating room vacuum supply or more sophisticated powered vacuum pumps. Regardless, if the seal of the vacuum chamber degrades the pressure in the chamber of the articulated structure will increase. In response to a signal from a pressure sensor coupled to the chamber, a shut-off valve 610' can automatically halt the flow of gas from the canister, close all balloon inflation valves, and/or open all balloon deflation valves. Such a vacuum system may provide worthwhile safety advantages when the articulated structure is to be used within a patient body and the balloons are to be inflated with a fluid that may initially take the form of a liquid but may vaporize to a gas. A lumen of a multi-lumen core shaft may be used to couple a pressure sensor of the manifold to a vacuum chamber of the articulated structure via a port of the proximal interface and an associated channel of the manifold assembly, with the vacuum lumen optionally comprising a central lumen of the multi-lumen shaft and the vacuum port being on or near the proximal end of the multi-lumen shaft.

Figure 18B:
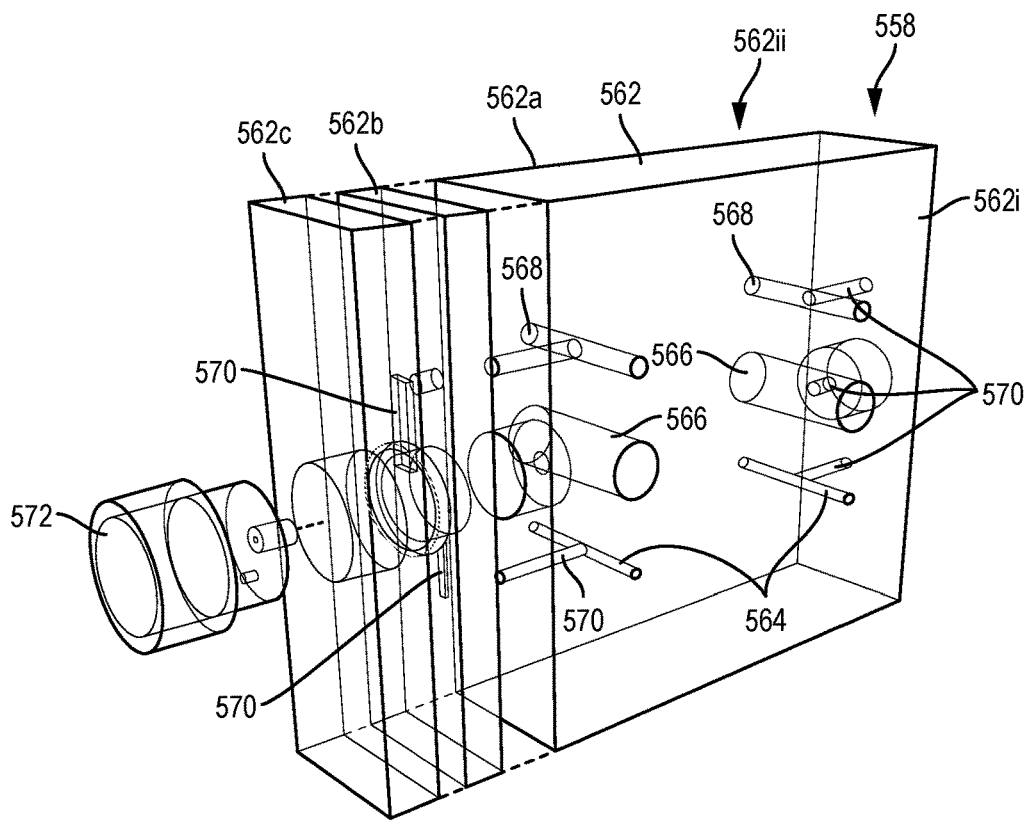
Figure 18C:
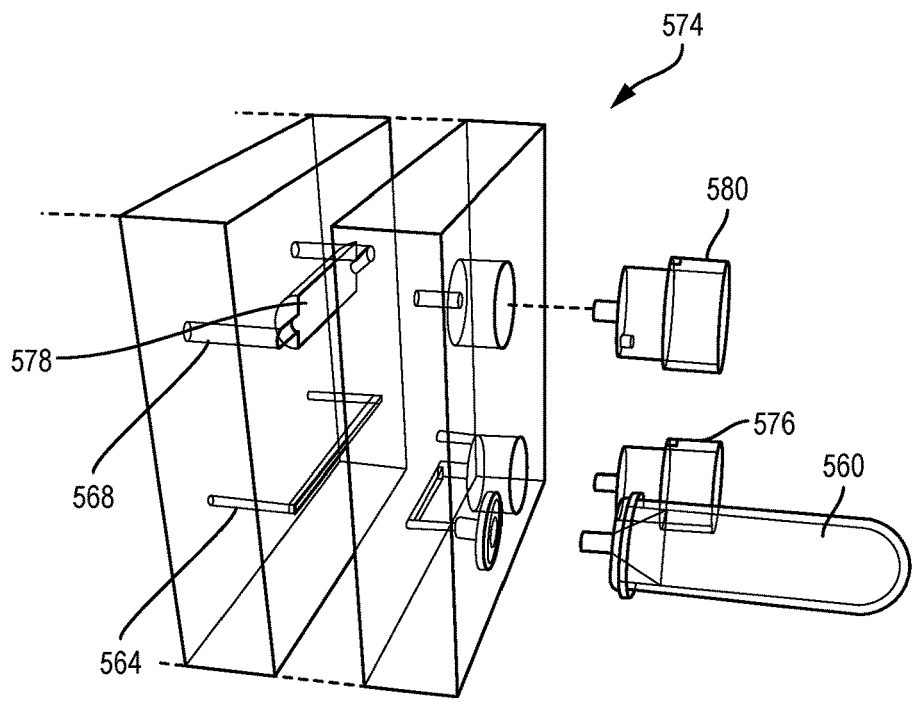

Referring now to FIGS. 18A-18C, an exemplary alternative modular manifold assembly 556 has fluid supply and deflation exhaust channels that are internal to a stack of plate modules 558. Plate modules 558 are stacked between a front end cap and a back end cap, with the front end cap being at the distal end and having passages or apertures for receiving each of the multi-lumen shafts, and the back end being at the proximal end and having a socket for receiving a canister 560 of N2O. As seen most clearly in FIG. 18B, each plate module 558 includes a plate 562 formed using multiple plate layers 562a, 562b, 562c . . . . While the plate layers shown here extend across the stack, other layers may be stacked axially along the stack. Regardless, each plate 562 has opposed proximal and distal major surfaces 562i, 562ii. A series of passages extend through the plate between the major surfaces, including one or more inflation fluid passage 564, one or more receptacle passages 566, and one or more deflation fluid passages 568. When the plates and end caps are assembled within manifold assembly 556, these passages combine to form one or more inflation header 564', one or more receptacle 566', and one or more deflation header 568', with each of the passages providing surfaces that serve as a portion of the assembled structure. Channels 570 extend within plates 562 between the headers 564, 568 and the receptacle, with inflation valves disposed along the channels between the inflation header 564 and receptacle 566 and deflation valves disposed along the channels between the receptacles and the deflation headers 568. Note that the manifold assembly of FIGS. 18A-18C includes multi-coil three way valves 572 that function as both inflation valves and deflation valves, with two three way valves for two multi-lumen core shafts.

Figure 18D:
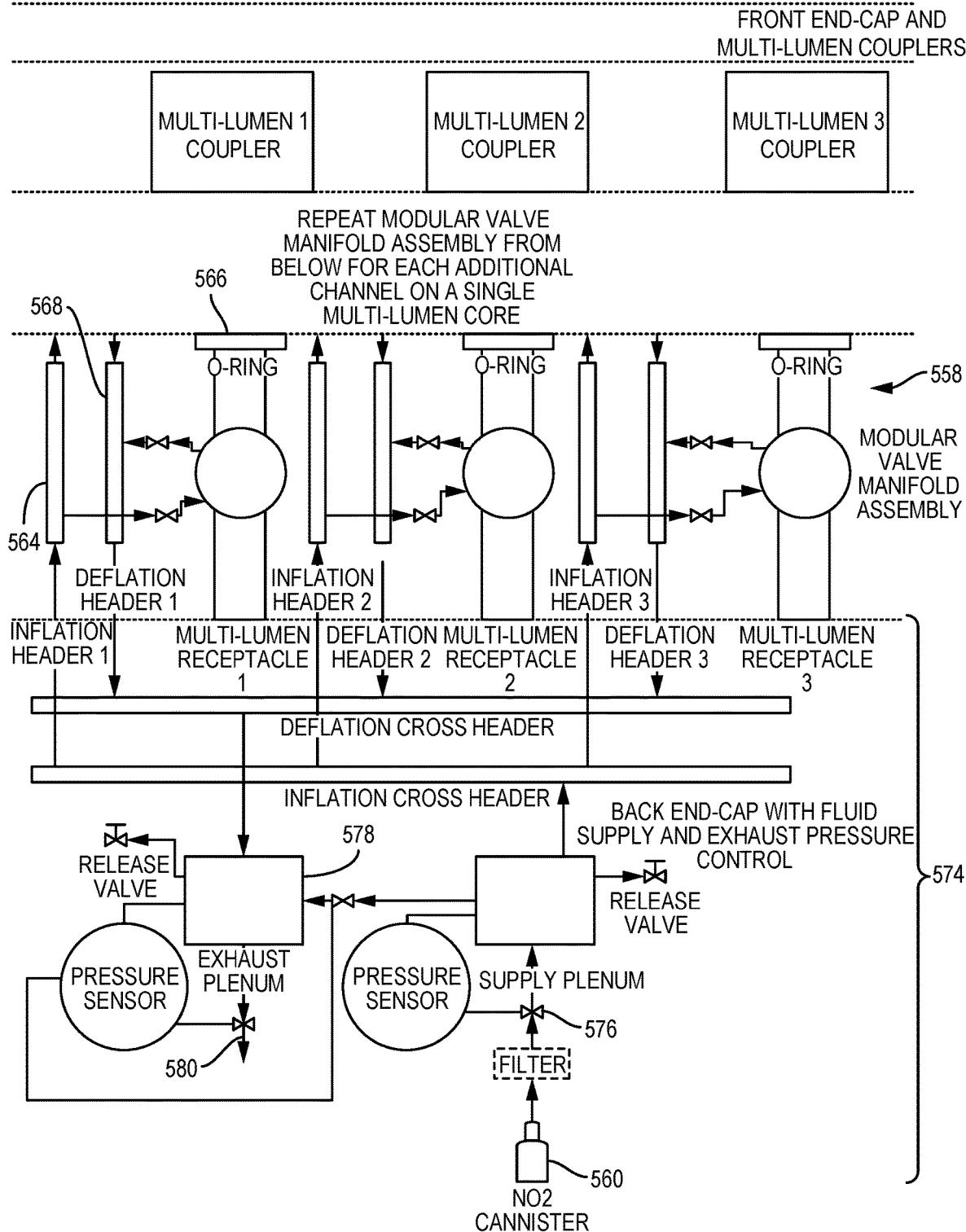
FIGS. 18D and 18E are alternative simplified schematics of modular fluid manifold systems showing additional components and systems that can be combined with those of FIG. 18.

Referring now to FIGS. 18C and 18D, additional optional components of the manifold assembly can be understood. The functionality of one, some, or all of these components may be included in any of the manifold assembly embodiments described herein. Back end cap 574 here includes a system fluid supply valve 576 disposed along channels coupling the inflation fluid canister 560 with the inflation header 564. Note that the end cap may include one or more cross headers to allow separate inflation or exhaust headers for the different multi-lumen core shafts. The system supply valve may halt or allow all of the fluid flow to the remaining components of the manifold and articulation structure. In some embodiments, fluid from canister 560 is used to pressurize a supply plenum, with a pressure sensor and the system supply valve being used to control the supply plenum pressure. This may be beneficial if it is desired to use a non-volatile balloon inflation liquid such as saline or the like, and/or if it is desired to preclude inflation of the balloons above a pressure that is below that of canister 560. However, transmitting inflation fluid directly from canister 560 to the inflation valves of the modular plates may present advantages, including enhanced inflation fluid flows through the small channels of the manifold and articulated structure when transmitting liquid or a liquid/gas mixture using the full canister pressure, as well as the relatively constant pressure that can be provided by vaporization of liquid within the canister. To keep the gas/liquid inflation fluid pressure within the canister even more constant, a resistive heater may be thermally coupled with the outer surface of the canister so as to compensate for the enthalpy of vaporization that occurs therein.

Referring still to FIGS. 18C and 18D, there may be more significant advantages to having an exhaust plenum 578 between one, some or all of the exhaust channels (often between the one or more exhaust header 568) and an exhaust port 580 to atmosphere. A pressure sensor or flow sensor coupled with exhaust plenum 578 can be used to monitor exhaust fluid flow. In some embodiments, a pressure sensor coupled to exhaust plenum 578 and an exhaust valve along a channel coupling the exhaust plenum to the exhaust port 580 can be used as a back-pressure control system to help control exhaust flows, to provide a uniform pressure to a number of balloons (via the deflation valves), or and/or to calibrate the individual pressure sensors of the plate modules. Manual release valves may optionally be included between the inflation and deflation headers and the surrounding environment to allow the system to be fully depressurized in case of failure of a valve or the like.

Figure 18E:
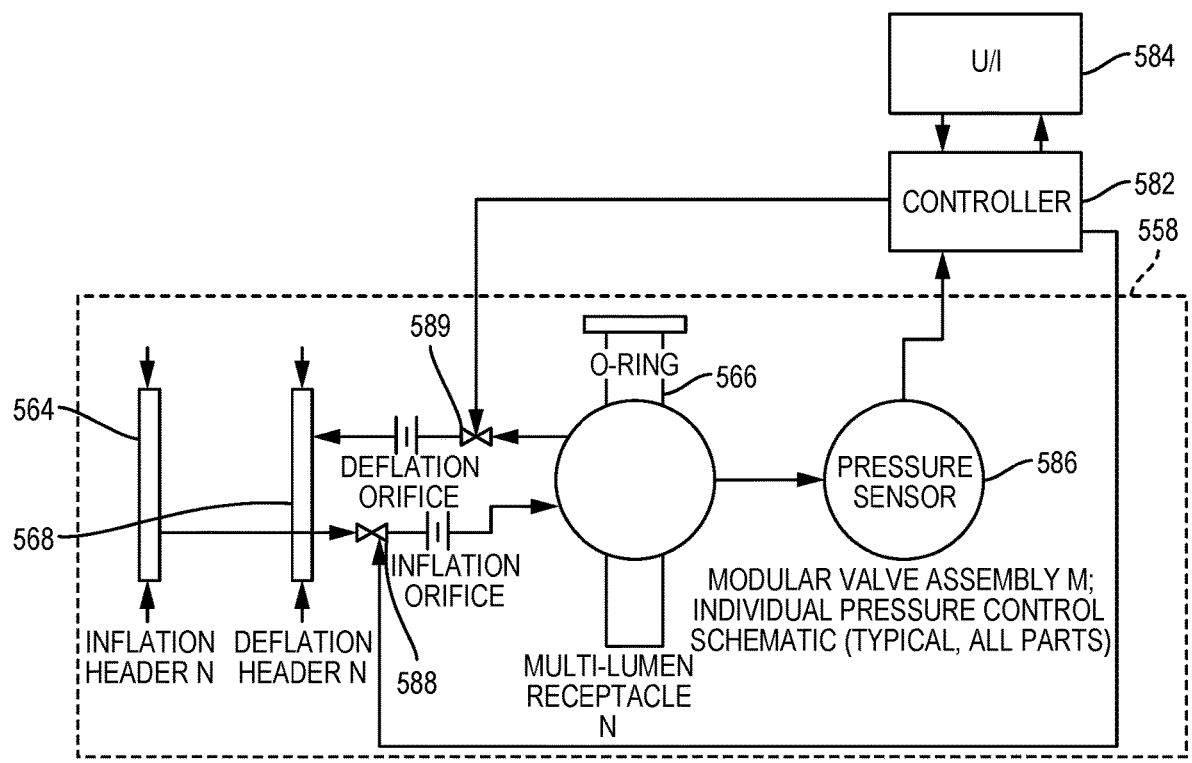

Referring now to FIG. 18E, a simplified pressure control schematic illustrates some of the components of a pressure control system as used to control the pressure in a single channel of a single plate module (as well as in an associated balloon or balloons coupled with the channel via a port of a multi-lumen shaft sealed in fluid communication with the channel. Pressure control of all the channels may be maintained by the system controller 582, with the desired pressures typically being determined by the controller in response to a movement or stiffness command input by the user via a user interface 584. A pressure difference or error signal for a particular channel is determined from a difference between a sensed pressure (as determined using a pressure sensor 586) and the desired pressure for that channel. In response to the error signal, controller 582 transmits commands to an inflation valve 588 and/or a deflation valve 589 so as to raise or lower the pressure in the channel. Though the same fluid is flowing to and from the balloons, there may be significant differences between the flows from the canister through inflation valve 588 (which may comprise liquid, often being primarily liquid or even substantially entirely liquid) and the flows from the balloons through deflation valve 589 (which may comprise gas, often being primarily gas or even substantially entirely gas). To provide accurate inflation and deflation flow control, there may be advantages to including an inflation orifice between the inflation valve and the receptacle (ideally so as to inhibit vaporization prior to the inflation valve), and/or to including a deflation orifice between the receptacle and the deflation header 568. Such orifices may facilitate accurate flow control despite the use of similar valve structures for use as inflation valve 588 and deflation valve 589. There may, however, be beneficial differences between the inflation and deflation valves, including the use of normally closed valves for inflation and normally open valves for deflation (so the balloons will deflate if there is a power failure). Additionally, inflation valve 588 may have a smaller throat and/or a fast response to controllably transmit small volumes of liquid (optionally 50 nl or less, often 25 nl or less, and preferably 15 nl or less, and ideally 10 nl or less to provide desirably small movement increments); while deflation valve 589 will allow gas flows of at least 0.1 scc/s, preferably being at least 0.5 scc/s or even 1 scc/s or more (to provide desirably fast articulation response). Hence, the throat sizes of these two valves may be different in some embodiments. Note that in some embodiments (particularly those with a pressure-controlled plenum between a canister and the inflation valves, or those having non-cryogenic pressurized fluid sources), the fluids flowing to and from may be more similar, for example, with liquid flowing to and from the balloons, gas flowing to and from the balloons, or the like.

Figure 18F:
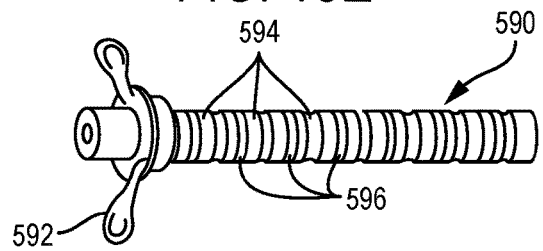
FIGS. 18F and 18G illustrate an interface for coupling any of a plurality of alternative multi-lumen shafts having differing sizes and/or shapes to a stacked-plate fluid manifold assembly.
Figure 18G:
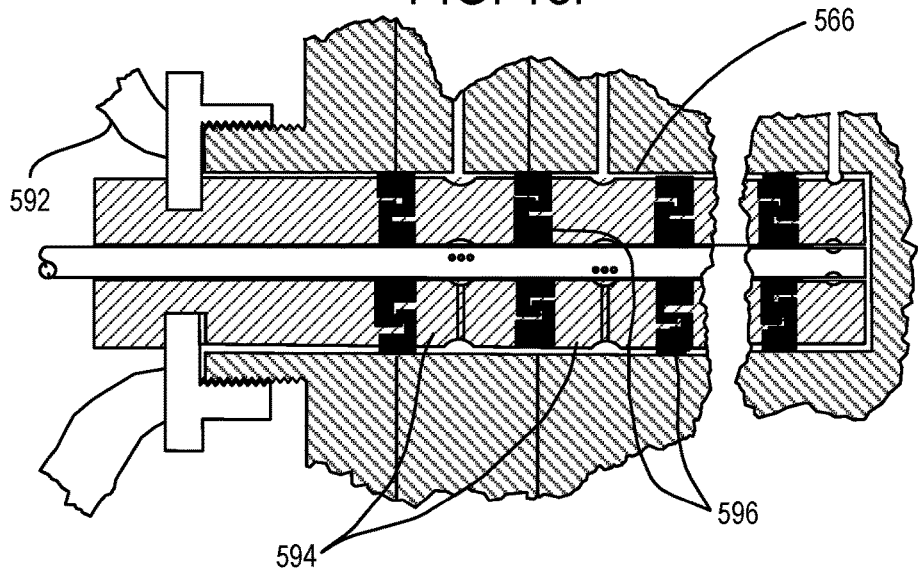

Referring to FIGS. 18F and 18G, it may be desirable to use a manifold assembly (or components thereof) with a number of different types of articulatable structures, for example with catheters having different sizes and/or shapes of multi-lumen shafts. Toward that end, it may be beneficial to include an interface body 590 for coupling a multi-lumen core shaft 592 (or other lumen-contain substrate) of the articulatable structure with a receptacle 566 of a manifold assembly 556. Interface body 590 has a proximal end and a distal end with an axial lumen extending therebetween. The axial lumen receives a multi-lumen shaft proximally, and the shaft may extend entirely through the interface body (so that registration between the ports of the shaft and the channels of the plate modules relies on engagement of the shaft with a surface of the back cap as shown in FIG. 18G, the receptacle comprising a blind hole) or the proximal end of the shaft may engage a bottom of the lumen in the interface body (so that the interface body is registered with the receptacle and the lumen is registered with the interface body). A quick disconnect fitting 592 is near the distal end of the interface body. Interface body 590 comprises a set of relatively rigid annular structures or rings 594 (optionally comprising metal or a relatively high-durometer polyme) interleaved with elastomeric seal material 596 (optionally overmolded on the rings or the like). Indentations optionally run circumferentially around the inner and outer surfaces in the middle of each ring, and one or more gas passages run radially between an inner surface of the ring and an outer surface of the ring, optionally between the indentations. Features may be included on the axial ends of the rings to inhibit separation of the body into axial segments.

Referring still to FIGS. 18F and 18G, the receptacle of the manifold may optionally comprise a smooth blind hole that extends through all valve plates of the stack. The valve plates may have fluid channels running into and out of the receptacle between the plate/plate borders. A feature of the manifold will often facilitate coupling, here being a short threaded tube that extends distally from the manifold around the opening of the receptacle. This feature mates with quick-disconnect fitting 592, shown as a wing-nut to affix the interface body and the multi-lumen shaft to the manifold. To connect the catheter to the manifold, the user inserts the multi-lumen shaft into the interface body, slides them both together into the receptacle of the manifold till the proximal end of the shaft hits the bottom of the receptacle (or till the interface body engages a registration feature). The user can engage and tightens the threads which axially compresses the connector shaft, causing the elastomeric seal material 596 to bulge inward (to seal around the multi-lumen shaft) and outward (to seal around the interface body), separating the receptacle into an axial series of sealed zones, one for each plate. Different interface bodies having different inner diameters and/or different inner cross-sections can be made for different shaft sizes and shapes. A single thread, fastener, or latch may optionally apply axial pressure to seal around a plurality of multi-lumen shafts, or separate quick-disconnect fittings may be included for each shaft.

Figure 19:
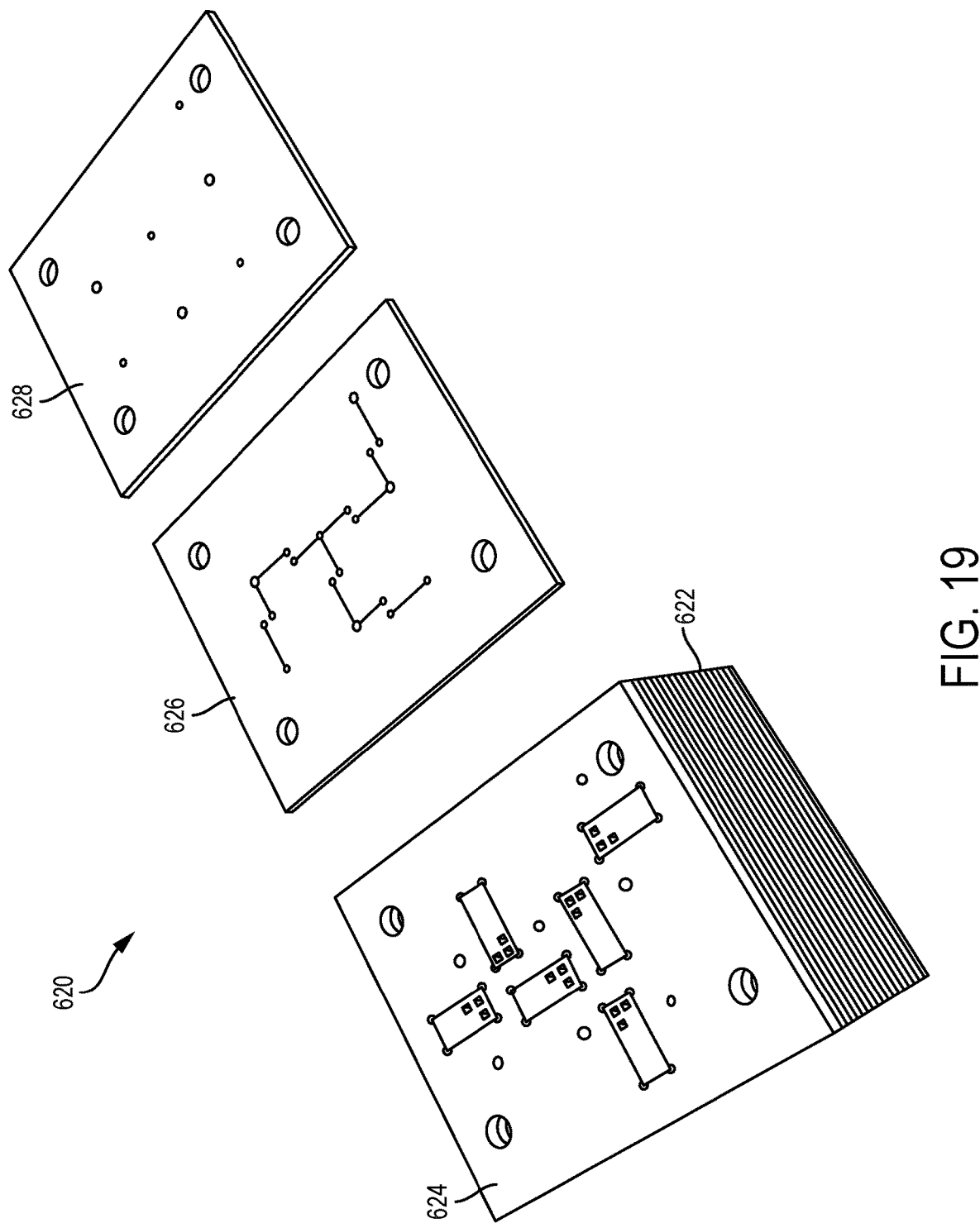
FIG. 19 is a perspective view of a modular manifold with the layers of one of the valve assemblies exploded so as to show the associated valves, axial passages, and lateral channels.

Referring now to FIG. 19, a further alternative manifold structure 620 includes a stack of valve unit plates 622 in which each valve unit is formed with three layers 624, 626, 628. All the layers include axial passages, and these passages are aligned along the axis of the inserted multi-lumen core shafts to define multi-lumen receptacles, inflation headers, deflation headers, and the like. First layer 624 includes valve receptacles containing discrete microelectromechanical system (MEMS) valves, which may be electrically coupled to the processor and/or mounted to the plate layer using a flex circuit adhesively bonded to the back side of the layer (not shown), with the flex circuit optionally having O-rings mounted thereon to seal between adjacent valve unit plates. Second valve layer 626 may have through-holes coupled by channels to provide flow between the valve ports, headers, and multi-lumen receptacles, and may be sealingly bonded between third plate layer 628 and first plate layer 624 (optionally with O-rings engaging the valves around the valve ports. Suitable MEMS valves may be available from DunAn Microstaq, Inc., of Texas, and the assembled modular valve-unit stack may have dimensions of less than 2½"×2½"×2" for a two or three multi-lumen core system having 12 lumens per core (and thus including 36 separately controllable lumen channels, and having an inflation valve and a deflation valve for each lumen for a total of at least 64 valves). Plate layers 624, 626, 628 may comprise polymers (particularly polymers which are suitable for use at low temperatures (such as PTFE, FEP, PCTFE, or the like), metal (such as aluminum, stainless steel, brass, alloys, an amorphous metal alloy such as a Liquidmetal™ alloy, or the like), glass, semiconductor materials, or the like, and may be mechanically machined or laser-micromachined, but will preferable be molded. Alternative MEMS valve systems may have the valve structure integrated into the channel plate structure, further reducing size and weight.

Figure 19A:
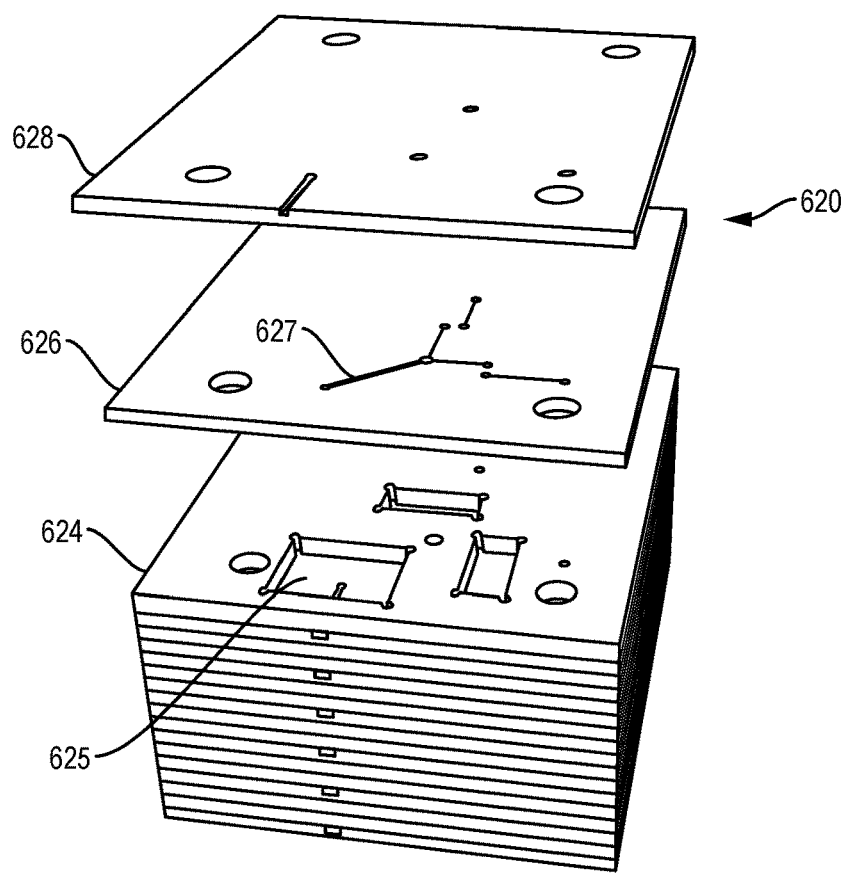
FIGS. 19A and 19B are a simplified perspective view and a schematic cross-sectional view, respectively, of plate layers used in a modular manifold similar to that of FIG. 19, showing channels and passages for one of three multi-lumens shafts.
Figure 19B:
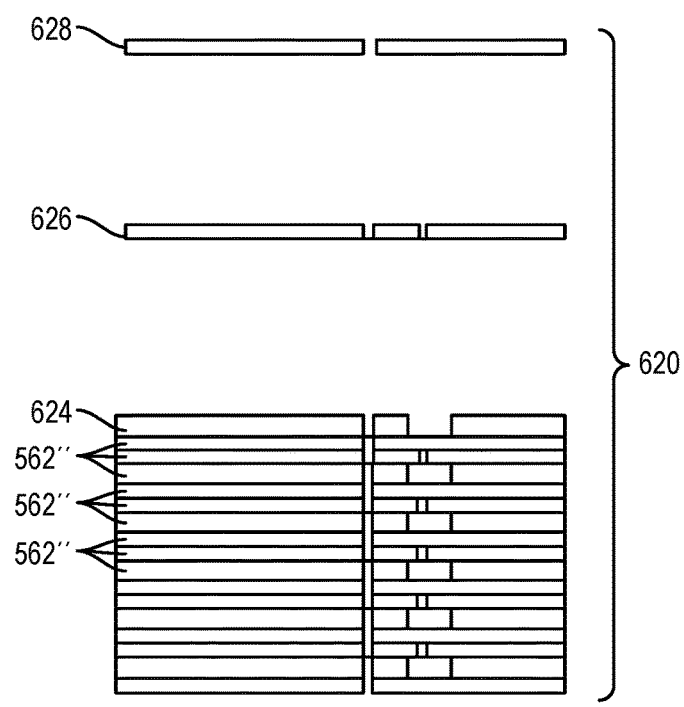

Referring to FIGS. 19A and 19B, additional features that can be included in the plate layer structure of MEMS manifold 620 can be understood. Many of the channels, passages, and features shown here are for interfacing with a single multi-lumen shaft for simplicity; additional features may be included for additional shafts. As control over the fluid channels may benefit from pressure sensors coupled with the channels of each plate module, an aperture for a MEMS pressure sensor 625 is included in first plate 624, with an associated channel 627 (extending between the receptacle and a pressure sensing region of the pressure sensor) being included in second plate 626. Suitable pressure sensors may be commercially available from Merit Sensor Systems and a number of alternative suppliers. As the pressure sensor and the valve may have different thicknesses, it may be beneficial to separate first layer 624 into two layers (with the aperture for the thicker components provided in both, and the aperture for the thinner component only being provided through one). As the pressure sensor may benefit from an external reference pressure, a relief channel may be formed in third plate 628 extending from a reference pressure location on the sensor to an external port. As can be understood with reference to FIG. 19B, the layers combine to form a plate structure 562", with each plate having opposed proximal and distal major surfaces. The plates (and the components supported thereon to make up the plate modules) can be stacked to form the modular manifold array.

Many of the flexible articulated devices described above rely on inflation of one or more balloons to articulate a structure from a first resting state to a second state in which a skeleton of the flexible structure is resiliently stressed. By deflating the balloons, the skeleton can urge the flexible structure back toward the original resting state. This simple system may have advantages for many applications. Nonetheless, there may be advantages to alternative systems in which a first actuator or set of actuators urges a flexible structure from a first state (for example, a straight configuration) to a second state (for example, a bent or elongate configuration), and in which a second actuator or set of actuators are mounted in opposition to the first set such that the second can actively and controllably urge the flexible structure from the second state back to the first state. Toward that end, exemplary systems described below often use a first set of balloons to locally axially elongate a structural skeleton, and a second set of balloons mounted to the skeleton to locally axially contract the structural skeleton. Note that the skeletons of such opposed balloon systems may have very little lateral or axial stiffness (within their range of motion) when no balloons are inflated.

Figure 20B:
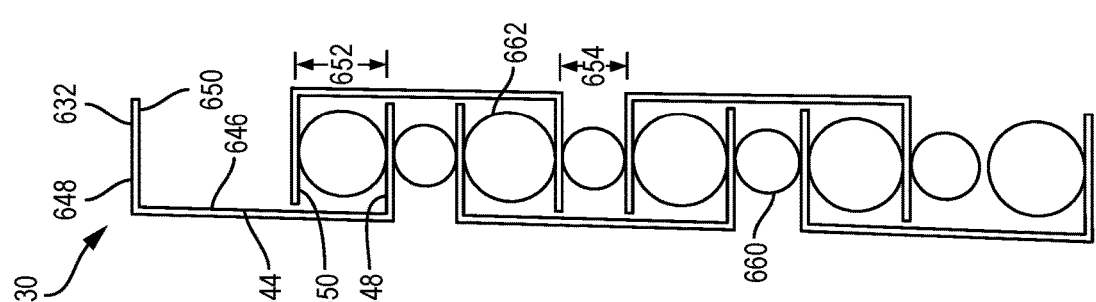
Figure 20A:
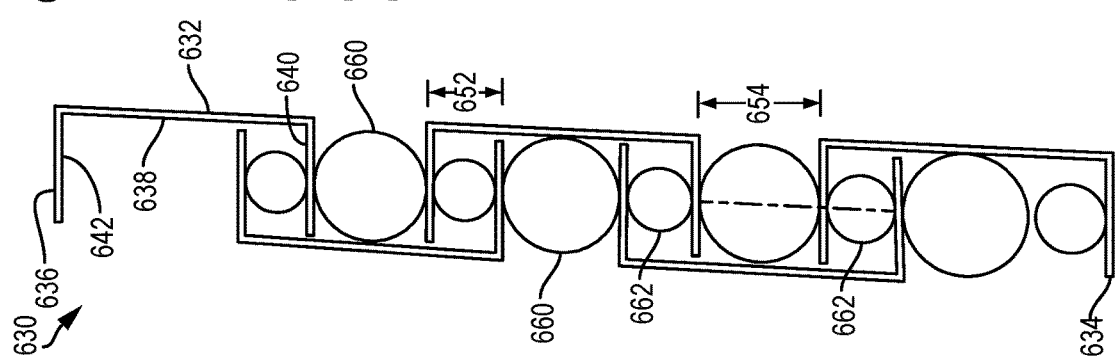

Referring now to FIGS. 20A and 20B, a simplified exemplary C-channel structural skeleton 630 (or portion or cross section of a skeleton) is shown in an axially extended configuration (in FIG. 20A), and in an axially contracted configuration (in FIG. 20B). C-frame skeleton 630 includes an axial series of C-channel members or frames 632 extending between a proximal end 634 and a distal end 636, with each rigid C-channel including an axial wall 638, a proximal flange 640, and a distal flange 642 (generically referenced as flanges 640). The opposed major surfaces of the walls 644, 646 are oriented laterally, and the opposed major surfaces of the flanges 648, 650 are oriented axially (and more specifically distally and proximally, respectively. The C-channels alternate in orientation so that the frames are interlocked by the flanges. Hence, axially adjacent frames overlap, with the proximal and distal surfaces 650, 648 of two adjacent frames defining an overlap offset 652. The flanges also define additional offsets 654, with these offsets being measured between flanges of adjacent similarly oriented frames.

In the schematics of FIGS. 20A and 20B, three balloons are disposed in the channels of each C-frame 632. Although the balloons themselves may (or may not) be structurally similar, the balloons are of two different functional types: extension balloons 660 and contraction balloons 662. Both types of balloons are disposed axially between a proximally oriented surface of a flange that is just distal of the balloon, and a distally oriented surface of a flange that is just proximal of the balloon. However, contraction balloons 662 are also sandwiched laterally between a first wall 638 of a first adjacent C-channel 632 and a second wall of a second adjacent channel. In contrast, extension balloons 660 have only a single wall on one lateral side; the opposite sides of extension balloons 660 are not covered by the frame (though they will typically be disposed within a flexible sheath or other components of the overall catheter system).

A comparison of C-frame skeleton 630 in the elongate configuration of FIG. 20A to the skeleton in the short configuration of FIG. 20B illustrates how selective inflation and deflation of the balloons can be used to induce axial extension and contraction. Note that the C-frames 632 are shown laterally reversed from each other in these schematics. In FIG. 20A, extension balloons 660 are being fully inflated, pushing the adjacent flange surfaces apart so as to increase the axial separation between the associated frames. As two contraction balloons 662 are disposed in each C-channel with a single extension balloon, and as the size of the channel will not significantly increase, the contraction balloons will often be allowed to deflate at least somewhat with expansion of the extension balloons. Hence, offsets 654 will be urged to expand, and contraction offsets 652 will be allowed to decrease. In contrast, when skeleton 630 is to be driven toward the axially contracted configuration of FIG. 20B, the contraction balloons 662 are inflated, thereby pushing the flanges of the overlapping frames axially apart to force contraction overlap 652 to increase and axially pull the local skeleton structure into a shorter configuration. To allow the two contraction balloons 662 to expand within a particular C-channel, the expansion balloons 660 can be allowed to deflate.

While the overall difference between C-frame skeleton 630 in the contracted configuration and in the extended configuration is significant (and such skeletons may find advantageous uses), it is worthwhile noting that the presence of one extension balloon and two contraction balloons in a single C-channel may present disadvantages as compared to other extension/contraction frame arrangements described herein. In particular, the use of three balloons in one channel can limit the total stroke or axial change in the associated offset that some of the balloons may be able to impose. Even if similar balloon/core assemblies are used as extension and contraction balloons in a three-balloon wide C-channel, the two contraction balloons may only be used for about half of the stroke of the single extension balloon, as the single extension stroke in the channel may not accommodate two full contractions strokes. Moreover, there are advantages to limiting the number of balloon/core assemblies used in a single articulated segment.

Note that whichever extension/contraction skeleton configuration is selected, the axial change in length of the skeleton that is induced when a particular subset of balloons are inflated and deflated will often be local, optionally both axially local (for example, so as to change a length along a desired articulated segment without changing lengths of other axial segments) and—where the frames extend laterally and/or circumferentially—laterally local (for example, so as to impose a lateral bend by extending one lateral side of the skeleton without changing an axial length of the other lateral side of the skeleton). Note also that use of the balloons in opposition will often involve coordinated inflating and deflating of opposed balloons to provide a maximum change in length of the skeleton. There are significant advantages to this arrangement, however, in that the ability to independently control the pressure on the balloons positioned on either side of a flange (so as to constrain an axial position of that flange) allows the shape and the position or pose of the skeleton to be modulated. If both balloons are inflated evenly at with relatively low pressures (for example, at less than 10% of full inflation pressures), the flange may be urged to a middle position between the balloons, but can move resiliently with light environmental forces by compressing the gas in the balloons, mimicking a low-spring force system. If both balloons are evenly inflated but with higher pressures, the skeleton may have the same nominal or resting pose, but may then resist deformation from that nominal pose with a greater stiffness.

Figure 21B:
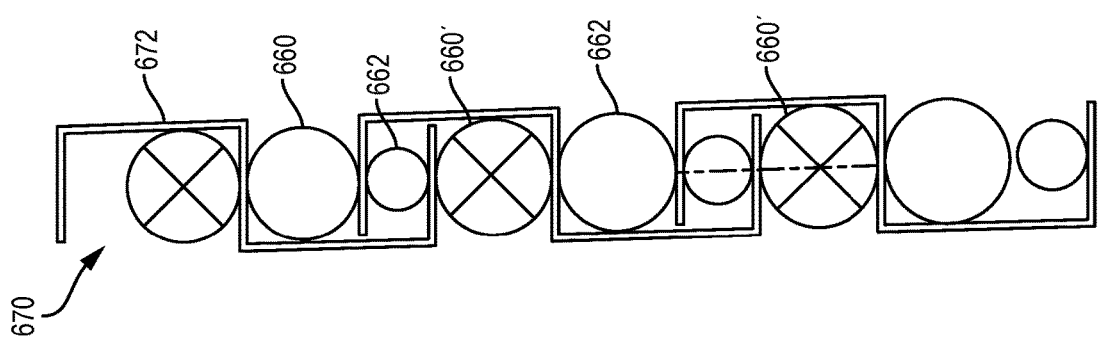
Figure 21A:
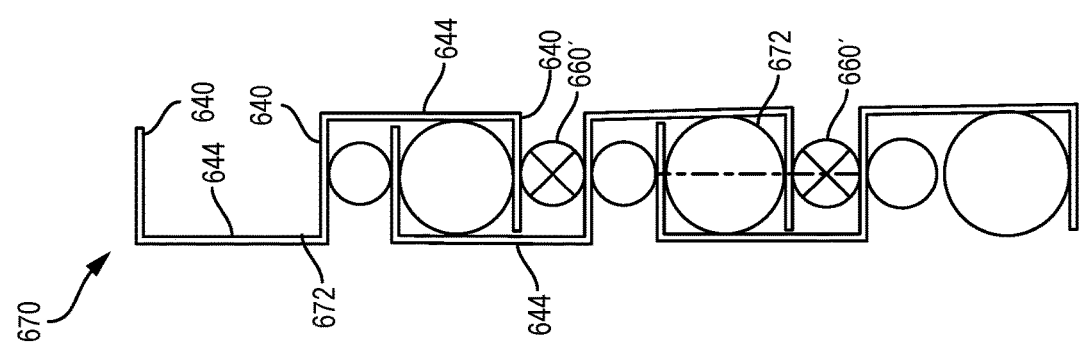

An alternative S-channel skeleton 670 is shown schematically in contracted and extended configurations in FIGS. 21A and 21B, respectively, which may have both an improved stroke efficiency (giving a greater percent change in axial skeleton length for an available balloon stroke) and have fewer components than skeleton 632. S-skeleton 670 has many of the components and interactions described above regarding C-frame skeleton 630, but is here formed of structural S-channel members or frames 672. Each S-channel frame 672 has two walls 644 and three flanges 640, the proximal wall of the frame having a distal flange that is integral with the proximal flange of the distal wall of that frame. Axially adjacent S-channels are again interlocked, and in this embodiment, each side of the S-channel frame has a channel that receives one extension balloon 660 and one contraction balloon 662. This allows all extension balloons and all contraction balloons to take full advantage of a common stroke. Moreover, while there are two extension balloons for each contraction balloon, every other extension balloon may optionally be omitted without altering the basic extension/contraction functionality (though the forces available for extension may be reduced). In other words, if the extension balloons 660' as marked with an X were omitted, the skeleton could remain fully constrained throughout the same nominal range of motion. Hence, S-channel frame 672 may optionally use three or just two sets of opposed balloons for a particular articulation segment.

Figure 22A:
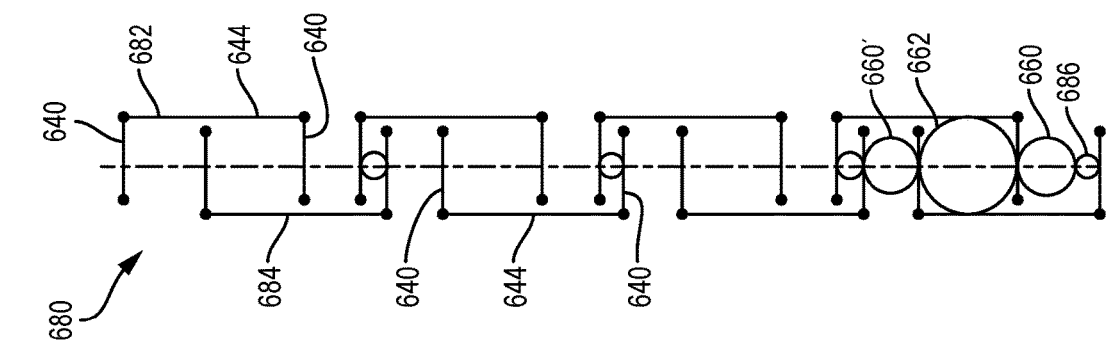

Referring now to FIG. 22A, a modified C-frame skeleton 680 has components that share aspects of both C-frame skeleton 630 and S-frame skeleton 670, and may offer advantages over both in at least some embodiments. Modified C skeleton 680 has two different generally C-frames or members: a C-frame 682, and a bumper C-frame 684. C-frame 682 and bumper frame 64 both have channels defined by walls 644 and flanges 648 with an axial width to accommodate two balloon assemblies, similar to the channels of the S-frames 672. Bumper frame 684 also has a protrusion or nub 686 that extends from one flange axially into the channel. The adjacent axial surfaces of these different frame shapes engage each other at the nub 686, allowing the frames to pivot relative to each other and facilitating axial bending of the overall skeleton, particularly when using helical frame members.

Referring now to FIGS. 22B and 22C, a relationship between the schematic extension/retraction frame illustration of FIGS. 20A-22A and a first exemplary three dimensional skeleton geometry can be understood. To form an axisymmetric ring-frame skeleton structure 690 from the schematic modified C-frame skeleton 680 of FIG. 22B, the geometry of frame members 682, 684 can be rotated about an axis 688, resulting in annular or ring frames 692, 694. These ring frames retain the wall and flange geometry described above, but now with annular wall and flanges being interlocked. The annular C-frames 682, 684 were facing different directions in schematic skeleton 680, so that outer C-frame ring 692 has an outer wall (sometimes being referred to as outer ring frame 692) and a channel that opens radially inwardly, while bumper C-frame ring 694 has a channel that is open radially outwardly and an inner wall (so that this frame is sometimes referred to as the inner ring frame 694). Ring nub 696 remains on inner ring frame 694, but could alternatively be formed on the adjacent surface of the outer ring frame (or using corresponding features on both). Note that nub 696 may add more value where the frame deforms with bending (for example, the frame deformation with articulation of the helical frame structures described below) as the deformation may involve twisting that causes differential angels of the adjacent flange faces. Hence, a non-deforming ring frame structure might optionally omit the nub in some implementations.

Referring now to FIGS. 22C-22F, uniform axial extension and contraction of a segment of ring-frame skeleton 690 is performed largely as described above. To push uniformly about the axis of the ring frames, three balloons are distributed evenly about the axis between the flanges (with centers separated by 120 degrees). The balloons are shown here as spheres for simplicity, and are again separated into extension balloons 660 and contraction balloons 662. In the straight extended configuration of FIG. 22D, the extension balloons 660 of the segment are all fully inflated, while the contraction balloons 662 are all fully deflated. In an intermediate length configuration shown in FIG. 22E, both sets of balloons 660, 662 are in an intermediate inflation configuration. In the short configuration of FIG. 22F, contraction balloons 662 are all fully inflated, while extension balloons 660 are deflated. Note that the state of the balloons remains axisymmetrical, so that the lengths on all lateral sides of the ring frame skeleton 690 remain consistent and the axis of the skeleton remains straight.

Figure 22G:
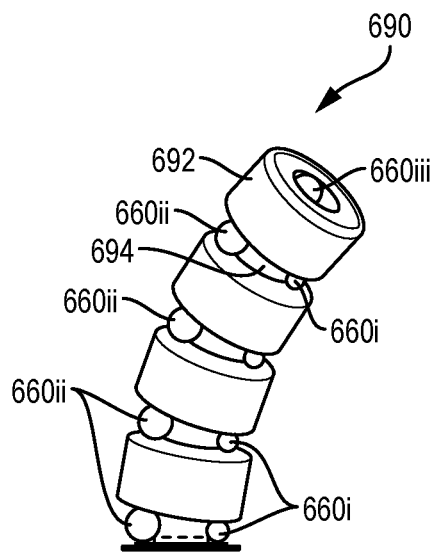
Figure 22H:
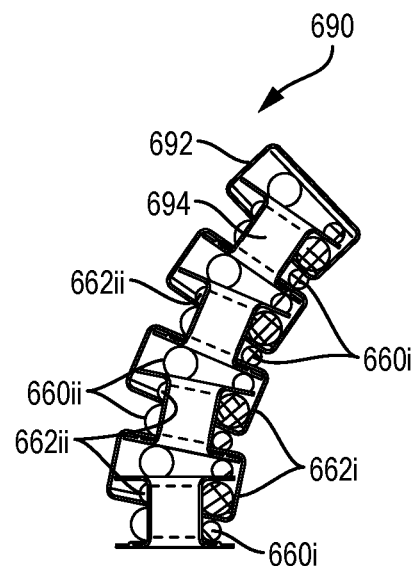

As can be understood with reference to FIGS. 22G and 22H, lateral bending or deflection of the axis of ring-frame skeleton 690 can be accomplished by differential lateral inflation of subsets of the extension and contraction balloons. There are three balloons distributed about the axis between each pair of articulated flanges, so that the extension balloons 660 are divided into three sets 660*i*, 660*ii*, and 660*iii*. Similarly, there are three sets of contraction balloons 662*i*, 662*ii*, and 662*iii*. The balloons of each set are aligned along the same lateral orientation from the axis. In some exemplary embodiments, each set of extension balloons (extension balloons 660*i*, extension balloons 660*ii*, and extension balloons 660*iii*) along a particular segment is coupled to an associated inflation fluid channel (for example, a channel i for extension balloons 660*i*, a channel ii for extension balloons 660*ii*, and a channel iii for extension balloons 660*iii*, the channels not shown here). Similarly, each set of contraction balloons 662*i*, 662*ii*, and 662*iii* is coupled to an associated inflation channel (for example, channels iv, v, and vi, respectively) so that there are a total of 6 lumens or channels per segment (providing three degrees of freedom and three orientation-related stiffnesses). Other segments may have separate fluid channels to provide separate degrees of freedom, and alternative segments may have fewer than 6 fluid channels. Regardless, by selectively deflating the extension balloons of a first lateral orientation 660*i* and inflating the opposed contraction balloons 662*i*, a first side of ring frame skeleton 690 can be shortened. By selectively inflating the extension balloons of the other orientations 660*ii*, 660*iii*, and by selectively deflating the contraction balloons of those other orientations 662*ii*, 662*iii*, the laterally opposed portion of ring frame skeleton 690 can be locally extended, causing the axis of the skeleton to bend. By modulating the amount of elongation and contraction distributed about the three opposed extension/contraction balloon orientations, the skeleton pose can be smoothly and continuously moved and controlled in three degrees of freedom.

Figure 23A:
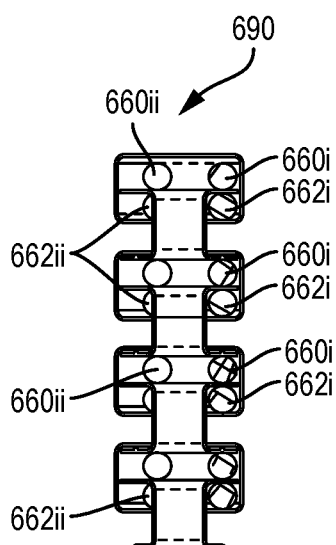
Figure 23B:
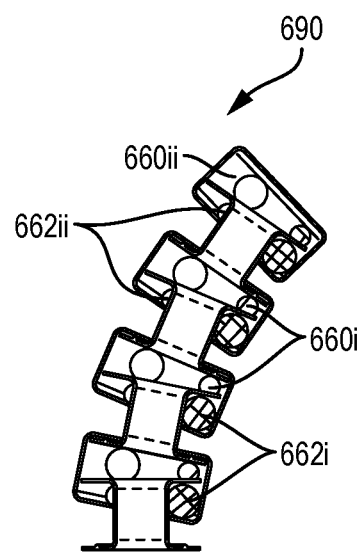

Referring now to FIGS. 23A and 23B, as described above with reference to FIGS. 21A and 21B, while it is possible to include balloons between all the separated flanges so as to maximize available extension forces and the like, there may be advantages to foregoing kinematically redundant balloons in the system for compactness, simplicity, and cost. Toward that end, ring frame skeletons having 1-for-1 opposed extension and contraction balloons (660*i*, 660*ii*, and 660*iii*; and 662*i*, 662*ii*, and 662*iii*) can provide the same degrees of freedom and range of motion as provided by the segments of FIGS. 22G and 22H (including two transverse X-Y lateral bending degrees of freedom and an axial Z degree of freedom), and can also control stiffness, optionally differentially modulating stiffness of the skeleton in different orientations in 3D space. The total degrees of freedom of such a segment may appropriately be referenced as being 4-D (X,Y,Z,&S for Stiffness), with the stiffness degree of freedom optionally having 3 orientational components (so as to provide as many as 5-D or 6-D. Regardless, the 6 fluid channels may be used to control 4 degrees of freedom of the segment.

As can be understood with reference to FIGS. 23C-23E and 23H, elongate flexible bodies having ring-frame skeletons 690' with larger numbers of inner and outer ring frames 692, 694 (along with associated larger numbers of extension and retraction balloons) will often provide a greater range of motion than those having fewer ring frames. The elongation or Z axis range of motion that can be provided by balloon articulation array may be expressed as a percentage of the overall length of the structure, with larger percentage elongations providing greater ranges of motion. The local changes in axial length that a balloon array may be able to produce along a segment having ring frames 690, 690' (or more generally having the extension contraction skeleton systems described herein) may be in a range of from about 1 percent to about 45 percent, typically being from about 2½ percent to about 25 percent, more typically being from about 5 percent to about 20 percent, and in many cases being from about 7½ percent to about 17½ percent of the overall length of the skeleton. Hence, the longer axial segment length of ring frame skeleton 690' will provide a greater axial range of motion between a contracted configuration (as shown in FIG. 23E) and an extended configuration (as shown in FIG. 23C), while still allowing control throughout a range of intermediate axial length states (as shown in FIG. 23D).

As can be understood with reference to FIGS. 23A, 23B, 23D and 23H, setting the balloon pressures so as to axially contract one side of a ring frame skeleton 690' (having a relatively larger number of ring frames) and axially extend the other side laterally bends or deflects the axis of the skeleton through a considerable angle (as compared to a ring frame skeleton having fewer ring frames), with each frame/frame interface typically between 1 and 15 degrees of axial bend angle, more typically being from about 2 to about 12 degrees, and often being from about 3 to about 8 degrees. A catheter or other articulated elongate flexible body having a ring frame skeleton may be bent with a radius of curvature (as measured at the axis of the body) of between 2 and 20 times an outer diameter of the skeleton, more typically being from about 2.25 to about 15 times, and most often being from about 2.4 to about 8 times. While more extension and contraction balloons 660, 662 are used to provide this range of motion, the extension and contraction balloon subsets (660*i*, 660*ii*, and 660*iii*; and 662*i*, 662*ii*, and 662*iii*) may still each be supplied by a single common fluid supply lumen. For example 6 fluid supply channels may each be used to inflate and deflate 16 balloons in the embodiment shown, with the balloons on a single lumen being extension balloons 660*i* aligned along one lateral orientation.

As can be understood with reference to ring frame skeleton 690' in the straight configuration of FIG. 23D, in the continuously bent configuration of FIG. 23H, and in the combined straight and bent configuration of FIG. 23F, exemplary embodiments of the elongate skeleton 690' and actuation array balloon structures described herein may be functionally separated into a plurality of axial segments 690*i*, 690*ii*. Note that many or most of the skeleton components (including frame members or axial series of frame members, and the like) and actuation array components (including the substrate and/or core, some or all of the fluid channels, the balloon outer tube or sheath material, and the like), along with many of the other structures of the elongate flexible body (such as the inner and outer sheaths, electrical conductors and/or optical conduits for diagnostic, therapeutic, sensing, navigation, valve control, and other functions) may extend continuously along two or more axial segments with few or no differences between adjacent segments, and optionally without any separation in the functional capabilities between adjacent segments. For example, an articulated body having a two-segment ring frame skeleton 690' system as shown in FIG. 23H may have a continuous axial series of inner and outer ring frames 692, 694 that extends across the interface between the joints such that the two segments can be bent in coordination with a constant bend radius by directing similar inflation fluid quantities and pressures along the fluid supply channels associated with the two separate segments. As can be understood with reference to FIG. 23G, other than differing articulation states of the segments, there may optionally be few or no visible indications of where one segment ends and another begins.

Despite having many shared components (and a very simple and relatively continuous overall structure), functionally separating an elongate skeleton into segments provides tremendous flexibility and adaptability to the overall articulation system. Similar bend radii may optionally be provided with differing stiffnesses by applying appropriately differing pressures to the opposed balloons 660, 662 of two (or more) segments 690*i*, 690*ii*. Moreover, as can be understood with reference to FIG. 23F, two (or more) different desired bend radii, and/or two different lateral bend orientations and/or two different axial segments lengths can be provided by applying differing inflation fluid supply pressures to the opposed contraction/extension balloon sets 660*i*, 660*ii*, 660*iii*, 662*i*, 662*ii*, 662*iii* of the segments. Note that the work spaces of single-segment and two-segment systems may overlap so that both types of systems may be able to place an end effector or tool at a desired position in 3D space (or even throughout a desired range of locations), but multiple-segment systems will often be able to achieve additional degrees of freedom, such as allowing the end effector or tool to be oriented in one or more rotational degrees of freedom in 6D space. As shown in FIG. 23J, articulated systems having more than two segments offer still more flexibility, with this embodiment of ring frame skeleton 690' having 4 functional segments 690*a*, 690*b*, 690*c*, and 690*d*. Note that still further design alternatives may be used to increase functionality and cost/complexity of the system for a desired workspace, such as having segments of differing length (such as providing a relatively short distal segment 690*a* supported by a longer segment having the combined lengths of 690*b*, 690*c*, and 690*d*. While many of the multi-segment embodiments have been shown and described with reference to planar configurations of the segments where all the segments lie in a single plane and are either straight or in a fully bent configuration, it should also be fully understood that the plurality of segments 690*i*, 690*ii*, etc., may bend along differing planes and with differing bend radii, differing axial elongation states, and/or differing stiffness states, as can be understood with reference to FIG. 23I.

Catheters and other elongate flexible articulated structures having ring frame skeletons as described above with reference to FIGS. 22C-23I provide tremendous advantages in flexibility and simplicity over known articulation systems, particularly for providing large numbers of degrees of freedom and when coupled with any of the fluid supply systems described herein. Suitable ring frames may be formed of polymers (such as nylons, urethanes, PEBAX, PEEK, HDPE, UHDPE, or the like) or metals (such as aluminum, stainless steel, brass, silver, alloys, or the like), optionally using 3D printing, injection molding, laser welding, adhesive bonding, or the like. Articulation balloon substrate structures may initially be fabricated and the balloon arrays assembled with the substrates in a planar configuration as described above, with the arrays then being assembled with and/or mounted on the skeletons, optionally with the substrates being adhesively bonded to the radially inner surfaces of the inner rings and/or to the radially outer surfaces of the outer rings, and with helical or serpentine axial sections of the substrate bridging between ring frames. While extension and retraction balloons 660, 662 associated with the ring frame embodiments are shown as spherical herein, using circumferentially elongate (and optionally bent) balloons may increase an area of the balloon/skeleton interface, and thereby enhance axial contraction and extension forces. A huge variety of modifications might also be made to the general ring-frame skeletal arrangement and the associated balloon arrays. For example, rather than circumferentially separating the balloons into three lateral orientations, alternative embodiments may have four lateral orientations (+X, −X, +Y, and −Y) so that four sets of contraction balloons are mounted to the frame in opposition to four sets of extension balloons. Regardless, while ring-frame skeletons have lots of capability and flexibility and are relatively geometrically simple so that their functionality is relatively easy to understand, alternative extension/contraction articulation systems having helical skeleton members (as described below) may be more easily fabricated and/or more easily assembled with articulation balloon array components, particularly when using the advantageous helical multi-lumen core substrates and continuous balloon tube structures described above.

First reviewing components of an exemplary helical frame contraction/expansion articulation system, FIGS. 24A-24E illustrate actuation balloon array components and their use in a helical balloon assembly. FIGS. 24F and 24G illustrate exemplary outer and inner helical frame members. After reviewing these components, the structure and use of exemplary helical contraction/expansion articulation systems (sometimes referred to herein as helical push/pull systems) can be understood with reference to FIGS. 25 and 26.

Figure 24A:
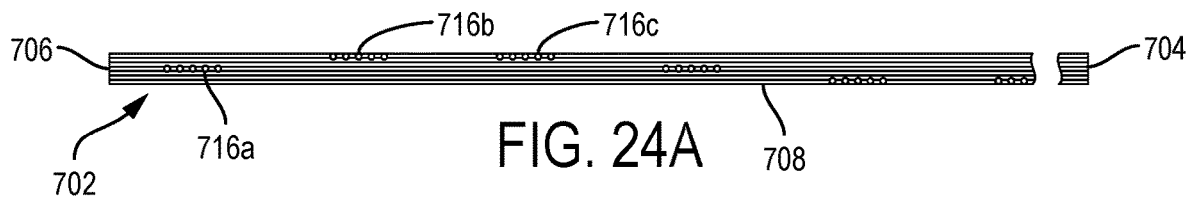
FIGS. 24A-24G illustrate components of another alternative elongate articulated flexible structure having axial expansion balloons and opposed axial contraction balloons, the structures here having helical skeleton members and helical balloon assemblies.
Figure 24B:
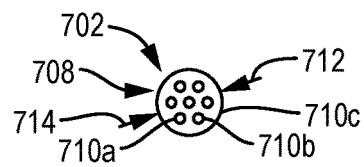

Referring now to FIGS. 24A and 24B, an exemplary multi-lumen conduit or balloon assembly core shaft has a structure similar to that of the core described above with reference to FIGS. 14 and 15. Core 702 has a proximal end 704 and a distal end 706 with a multi-lumen body 708 extending therebetween. A plurality of lumens 710*a*, 710*b*, 710*c*, ... extend between the proximal and distal ends. The number of lumens included in a single core 702 may vary between 3 and 30, with exemplary embodiments have 3, 7 (of which one is a central lumen), 10 (including 1 central), 13 (including 1 central), 17 (one being central), or the like. The multi-lumen core will often be round but may alternatively have an elliptical or other elongate cross-section as described above. When round, core 702 may have a diameter 712 in a range from about 0.010" to about 1", more typically being in a range from about 0.020" to about 0.250", and ideally being in a range from about 0.025" to about 0.100" for use in catheters. Each lumen will typically have a diameter 714 in a range from about 0.0005" to about 0.05", more preferably having a diameter in a range from about 0.001" to about 0.020", and ideally having a diameter in a range from about 0.0015" to about 0.010". The core shafts will typically comprise extruded polymer such as a nylon, urethane, PEBAX, PEEK, PET, other polymers identified above, or the like, and the extrusion will often provide a wall thickness surrounding each lumen of more than about 0.0015", often being about 0.003" or more. The exemplary extruded core shown has an OD of about 0.0276", and 7 lumens of about 0.004" each, with each lumen surrounded by at least 0.004" of the extruded nylon core material.

Referring still to FIGS. 24A and 24B, the lumens of core 702 may have radial balloon/lumen ports 716a, 716b, 716c, . . . , with each port comprising one or more holes formed through the wall of core 702 and into an associated lumen 710a, 710b, 710c, . . . respectively. The ports are here shown as a group of 5 holes, but may be formed using 1 or more holes, with the holes typically being round but optionally being axially elongate and/or shaped so as to reduce pressure drop of fluid flow therethrough. In other embodiments (and particularly those having a plurality of balloons supplied with inflation fluid by a single lumen), having a significant pressure drop between the lumen and the balloon may help even the inflation state of balloons, so that a total cross section of each port may optionally be smaller than a cross-section of the lumen (and/or by limiting the ports to one or two round lumens). Typical ports may be formed using 1 to 10 holes having diameters that are between 10% of a diameter of the associated lumen and 150% of the diameter of the lumen, often being from 25% to 100%, and in many cases having diameters of between 0.001" and 0.050". Where more than one hole is included in a port they will generally be grouped together within a span that is shorter than a length of the balloons, as each port will be contained within an associated balloon. Spacing between the ports will correspond to a spacing between balloons to facilitate sealing of each balloon from the axially adjacent balloons.

Regarding which lumens open to which ports, the ports along a distal portion of the core shaft will often be formed in sets, with each set being configured to provide fluid flow to and from an associated set of balloons that will be distributed along the loops of the core (once the core is bent to a helical configuration) for a particular articulated segment of the articulated flexible body. When the number of lumens in the core is sufficient, there will often be separate sets of ports for different segments of the articulated device. The ports of each set will often form a periodic pattern along the axis of the multi-lumen core 702, so that the ports provide fluid communication into M different lumens (M being the number of different balloon orientations that are to be distributed about the articulated device axis, often being 3 or 4, i.e., lumen 710a, lumen 710b, and lumen 710c) and the pattern repeating N times (N often being the number of contraction balloons along each orientation of a segment). Hence, the multi-lumen core conduit can function as a substrate that supports the balloons, and that defines the balloon array locations and associated fluid supply networks described above. Separate multi-lumen cores 702 and associated balloon arrays may be provided for contraction and expansion balloons.

As one example, a port pattern might be desired that includes a 3×5 contraction balloon array for a particular segment of a catheter. This set of ports might be suitable when the segment is to have three lateral balloon orientations (M=3) and 5 contraction balloons aligned along each lateral orientation (N=5). In this example, the distal-most port 716a of the set may be formed through the outer surface of the core into a first lumen 710a, the next proximal port 716b to lumen 710b, the next port 716c to lumen 710c, so that the first 3 (M) balloons define an "a, b, c" pattern that will open into the three balloons that will eventually be on the distal-most helical loop of the set. The same pattern may be repeated 5 times (for example: a, b, c, a, b, c, a, b, c, a, b, c, a, b, c) for the 5 loops of the helical coil that will support all 15 contraction balloons of a segment to the fluid supply system such that the 5 contraction balloons along each orientation of the segment are in fluid communication with a common supply lumen. Where the segment will include expansion balloons mounted 1-to-1 in opposition to the contraction balloons, a separate multi-lumen core and associated balloon array may have a similar port set; where the segment will include 2 expansion balloons mounted in opposition for each contraction balloon, two separate multi-lumen cores and may be provided, each having a similar port set.

If the same multi-lumen core supplies fluid to (and supports balloons of) another independent segment, another set of ports may be provided axially adjacent to the first pattern, with the ports of the second set being formed into an M'×N' pattern that open into different lumens of the helical coil (for example, where M'=3 and N'=5: d, e, f, d, e, f, d, e, f, d, e, f, d, e, f), and so on for any additional segments. Note that the number of circumferential balloon orientations (M) will often be the same for different segments using a single core, but may be different in some cases. When M differs between different segments of the same core, the spacing between ports (and associated balloons mounted to the core) may also change. The number of axially aligned contraction balloons may also be different for different segments of the same helical core, but will often be the same. Note also that all the balloons (and associated fluid lumens) for a particular segment that are on a particular multi-lumen core will typically be either only extension or only contraction balloons (as the extension and contraction balloon arrays are disposed in helical spaces that may be at least partially separated by the preferred helical frame structures described below). A single, simple pattern of ports may be disposed near the proximal end of core shaft 702 to interface each lumen with an associated valve plate of the manifold, the ports here being sized to minimized pressure drop and the port-port spacing corresponding to the valve plate thickness. Regardless, the exemplary core shown has distal ports formed using groups of 5 holes (each having a diameter of 0.006", centerline spacing within the group being 0.012"), with the groups being separated axially by about 0.103".

Figure 24C:
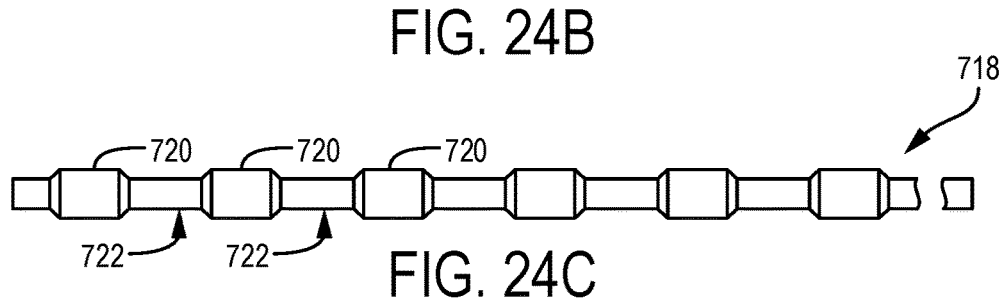
Figure 24D:
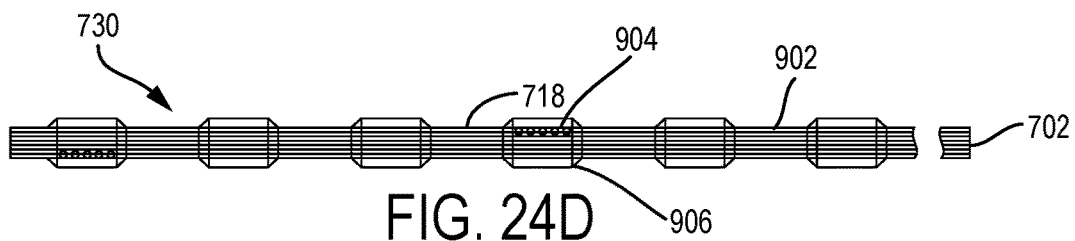

Referring now to FIGS. 24C and 24D, a continuous tube of flexible balloon wall material 718 may be formed by periodically varying a diameter of tube wall material to form a series of balloon shapes 720 separated by smaller profile sealing zones 722. Balloon tube 718 may include between about 9 and about 290 regularly spaced balloon shapes 720, with the sealing zones typically having an inner diameter that is about equal to the outer diameters of the multi-lumen helical core shafts 702 described above. In some embodiments, the inner diameters of the sealing zones may be significantly larger than the outer diameters of the associated cores when the balloon tube is formed, and the diameters of the sealing zones may be decreased (such as by heat shrinking or axially pull-forming) before or during assembly of the balloon tube and core shaft. The sealing zone may have a length of between about 0.025" and about 0.500", often being between about 0.050" and about 0.250". Decreasing the length of the sealing zone allows the length of the balloon to be increased for a given catheter size so as to provide larger balloon/frame engagement interfaces (and thus greater articulation forces), while longer sealing zones may facilitate assembly and sealing between balloons so as to avoid cross-talk between articulation channels.

Referring still to FIGS. 24C and 24D, the balloon shapes 720 of the balloon tube 718 may have diameters that are larger than the diameters of the sealing zones by between about 10% and about 200%, more typically being larger by an amount in a range from about 20% to about 120%, and often being from about 40% to about 75%. The thickness of balloon tube 718 will often vary axially with the varying local diameter of the tube, the locally large diameter portions forming the balloon shapes optionally being in a range from about 0.00008' (or about 2 microns) to about 0.005", typically being from about 0.001" and about 0.003". Balloon tube 718 may initially be formed with a constant diameter and thickness, and the diameter may be locally expanded (by blow forming, by vacuum forming, by a combination of both blow forming and vacuum forming, or by otherwise processing the tube material along the balloon shapes 720), and/or the diameter of the balloon tube may be locally decreased (by heat shrinking, by axial pull-forming, by a combination of both heat shrinking and pull forming, or by otherwise processing the tube material along the sealing zones), with the tube material often being processed so as to both locally expand the diameter along the desired balloon shapes and to locally contract the diameter along the sealing zones. Particularly advantageous techniques for forming balloon tubes may include the use of extruded polymer tubing corrugators, including the vertical small bore corrugators commercially available from Unicore, Corma, Fraenkische, and others. Suitable custom molds for such pipe corrugators may be commercially available from GlobalMed, Custom Pipe, Fraenkische, and others. Still more advanced fabrication techniques may allow blow or vacuum corrugation using a robotic shuttle corrugator and custom molds, particularly when it is desirable to change a size or spacing of balloons along a continuous tube. It should be noted that while a single continuous balloon tube is shown, a plurality of balloon tubes (each having a plurality (or in some cases, at least one) balloon shape) can be sealingly mounted onto a single core. Regardless, the sealing zones will often have a material thickness that is greater than that of the balloon shapes.

The balloon shapes 720 of the balloon tube 718 may each have a relatively simple cylindrical center section prior to assembly as shown. The tapers between the balloon center sections and the sealing zones can take any of a variety of shapes. The tapers may, for example, be roughly conical, rounded, or squared, and will preferably be relatively short so as to allow greater balloon/frame engagement for a given landing zone length. More complex embodiments may also be provided, including forming the balloon shapes with curved cylindrical center sections, optionally while corrugating or undulating the surfaces of the tapers so that the balloon tube overall remains relatively straight. The lengths of each center section is typically sufficient to define an arc-angle of from 5 to 180 degrees about the axis of the desired balloon assembly helix, more typically being from about 10 to about 50 degrees, the lengths of the center sections often being in a range from about 0.010" to about 0.400" for medical applications, more typically being from about 0.020" to about 0.150", and many times being in a range from about 0.025" to about 0.100". The exemplary balloon shapes may have an outer diameter of about 0.051" over a total balloon length (including the tapers) of about 0.059"

Figure 24E:
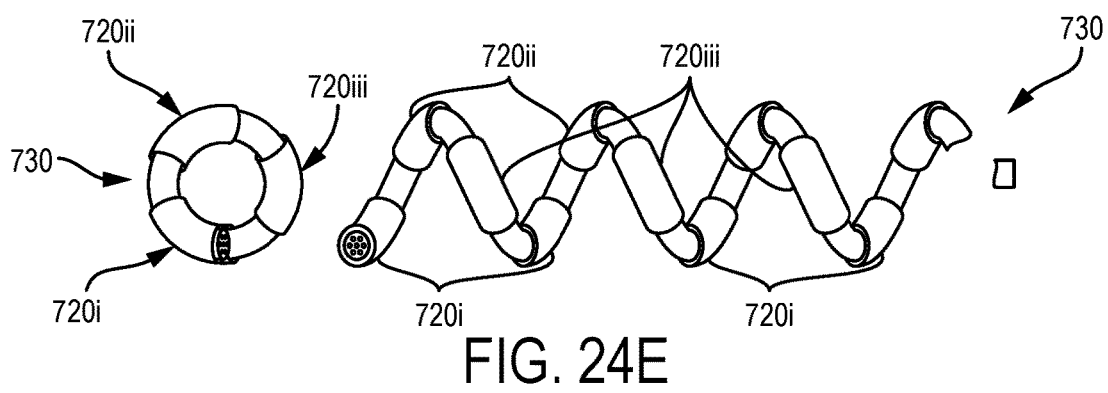
Figure 24F:
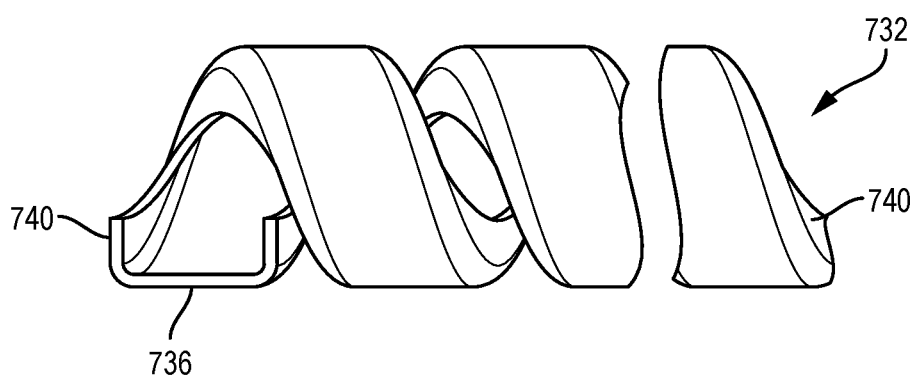
Figure 24G:
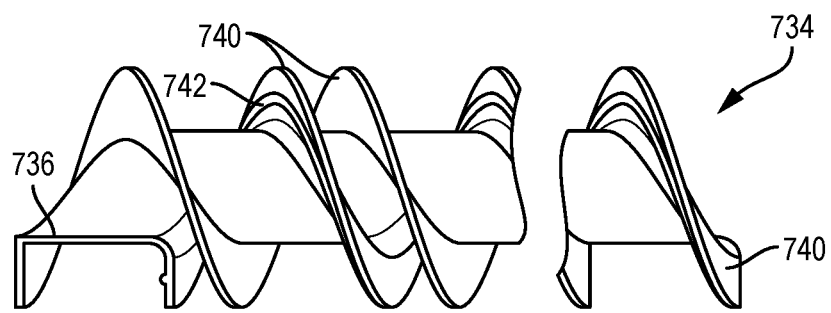

As can be understood with reference to FIGS. 24C, 24D, and 24E, balloon tube 718 may be sealingly affixed to core 702, and the core/balloon tube assembly may then be formed into a desired helical shape. The balloon tube may be sealed over the helical core using adhesive (such as any of those described above, often including UV-cured adhesives) thermal bonding, laser bonding, die bonding, and/or the like. Sealing of the balloons may also benefit from a compression structure disposed over the balloon material to help maintain tube/core engagement when the balloons are inflated. Suitable compression structures or techniques may include short sections of heat-shrink materials (such as PET) shrunk onto the sealing zones, high-strength filament windings wrapped circumferentially around the sealing zones and adhesively bonded, swaging of metallic ring structures similar to marker bands over the sealing zones, small bore crimp clamps over the sealing zones, heat-shrinking and/or pull forming the balloon tube onto the core, or the like. Any two or more of these may also be combined, for example, with the balloon tube being adhesively bonded to the core tube by injecting adhesive into the balloon tube around the sealing zone, heat shrinking the balloon tube and a surrounding PET sleeve over the sealing zone, and then swaging a metallic marker band over the sealing PET sleeve (so that the sleeve provides strain relief). Regardless, ports 716 will preferably be disposed within corresponding balloon shapes 720 and will remain open after the balloon/core assembly 730 is sealed together in the straight configuration shown in FIG. 24D. Shape setting of the balloon/core assembly from the straight configuration to the helically curved configuration of FIG. 24E can be performed by wrapping the assembly around and/or within a mandrel and heating the wrapped assembly. Helical channels may be included in the mandrel, which may also have discrete balloon receptacles or features to help ensure alignment of sets of balloons along the desired lateral balloon axes. Regardless, shape setting of the core/balloon assembly can help set the M different lateral orientations of the balloons, so that the balloons of each set 720*i*, 720*ii*, 720*iii* are aligned.

Referring now to FIGS. 24F and 24G, exemplary inner and outer helical C-channel frames, 732 and 734 respectively, can be seen. Inner helical frame 732 and outer helical frame 734 incorporate the modified C-channel frame 680 of FIG. 22*a*, but with the C-channels defined by axially continuous helical walls 736 with flanges 740 along their proximal and distal helical edges. The helical flanges are axially engaged by opposed balloons and allow inflation of the balloons to locally axially contract and/or extend the skeleton and catheter (or other articulatable body) in a manner that is analogous to the annular flanges of the ring frames described above. An optional helical nub 742 protrudes axially into the channel of inner ring frame 734 to allow the frames to pivot against each other along a flange/flange engagement, so that the nub could instead be included on the flange of the outer frame or on both (or may comprise a separate structure that is axially sandwiched between the flanges of the two frames). Alternative embodiments may forego such a pivotal structure altogether.

Referring now to FIGS. 25A-25D, a segment of an exemplary flexible extension/contraction helical frame articulation structure 750 (sometimes referred to herein as a push/pull helical structure) incorporates the components of FIGS. 24A-24G, and provides the functionality of the annular extension/contraction frame embodiments of FIGS. 22B-22I. Push/pull structure includes a skeleton defined by inner and outer helical frames 732, 734, and also includes three balloon/core assemblies 730a, 730b, and 730c, respectively. Each balloon/core assembly includes a set of balloons at three lateral orientations, 720i, 720ii, and 720iii. Balloon/core assembly 730b extends along a helical space that is axially between a flange of the inner frame and a flange of the outer frame, and that is radially between a wall of the inner frame and a wall of the outer frame, so that the frames overlap along this balloon/core assembly. Hence, when balloons 720 of balloon/core assembly 730 inflate, they push the adjacent flanges apart and increase the overlap of the frames, inducing axial contraction of the skeleton, such that the balloons of this assembly function as contraction balloons. In contrast, balloon/core assemblies 730a and 730c are radially adjacent to only inner frame 732 (in the case of assembly 730a) or outer frame 734 (in the case of assembly 730b). Expansion of the balloons 720 of assemblies 730a, 730c pushes axially against frames so as to decrease the overlap of the frames, and acts in opposition to the inflation of balloons 720 of assembly 730b. Hence, balloons 720 of assemblies 730a, 730c function as extension balloons.

Referring now to FIGS. 25A-25C, when all the contraction balloons 720 of assembly 730b are inflated and all the extension balloons of assemblies 730a, 730c are deflated, the push/pull structure 750 is in a straight short configuration as shown in FIG. 25A. Even partial inflation of the extension balloons and even partial deflation of the contraction balloons articulates push/pull structure 750 to a straight intermediate length configuration, and full inflation of all extension balloons of assemblies 730a, 730c (along with deflation of the contraction balloons) fully axially elongates the structure. As with the ring push/pull frames, inflating contraction balloons 720ii along one lateral orientation of assembly 730b (with corresponding deflation of the extension balloons 720ii of assemblies 730a, 730b) locally decreases the axial length of the skeleton along that side, while selective deflation of contraction balloons 720i of assembly 730b (with corresponding inflation of extension balloons 720i of assemblies 730a and 730c) locally increases the length of the skeleton, resulting in the fully laterally bent configuration of FIG. 25E. Note that extension and contraction balloons along the 720iii orientation may be inflated and deflated with the extension and contraction orientation balloons of orientation 720ii so as to keep the curvature in the plane of the drawing as shown. Stiffness of the structure may be modulated uniformly or locally (with axial and/or orientation variations) as described above regarding the ring frame embodiments. Similarly, the number of extension and contraction balloons along each orientation (which will often be associated with the number of loops of assemblies 730a, 730b, etc) may be determined to provide the desired range of motion, resolution, and response. As described with reference to the push/pull ring frame embodiments, the overall articulated portion of the structure will often be separated into a plurality of independently controllable segments.

Figure 25F:
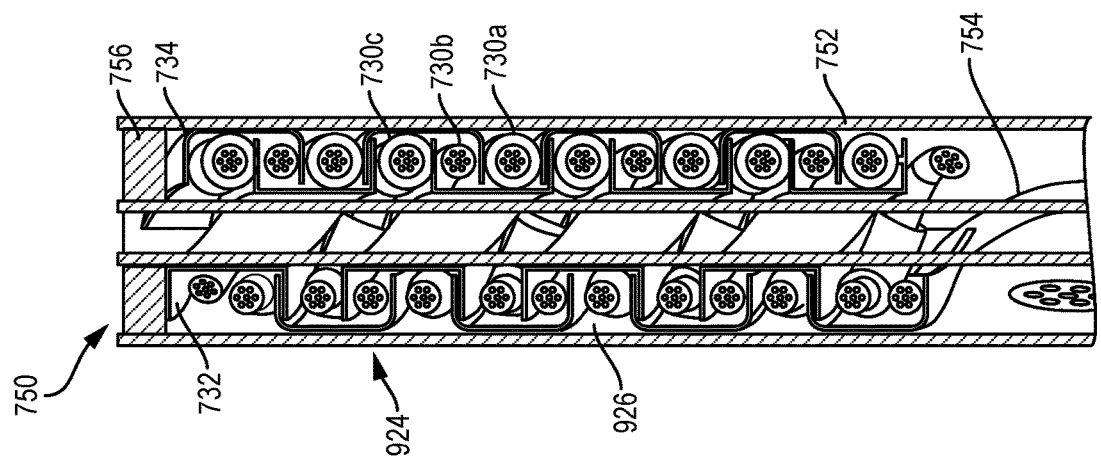

Referring now to FIG. 25F, push/pull structure 750 will often include an outer flexible sheath 752 and an inner flexible sheath 754. Sheaths 752, 754 may be sealed together at a distal seal 756 distal of the inflation lumens and balloons of assemblies 730, and one or more proximal seal (not shown) may be provided proximal of the balloons and/or near a proximal end of the catheter structure, so as to provide a sealed volume or chamber 754' surrounding the articulation balloons. A vacuum can be applied to this sealed volume, and can be monitored to verify that no leaks are present in the balloons or inflation lumen system within a patient body.

Figure 26B:
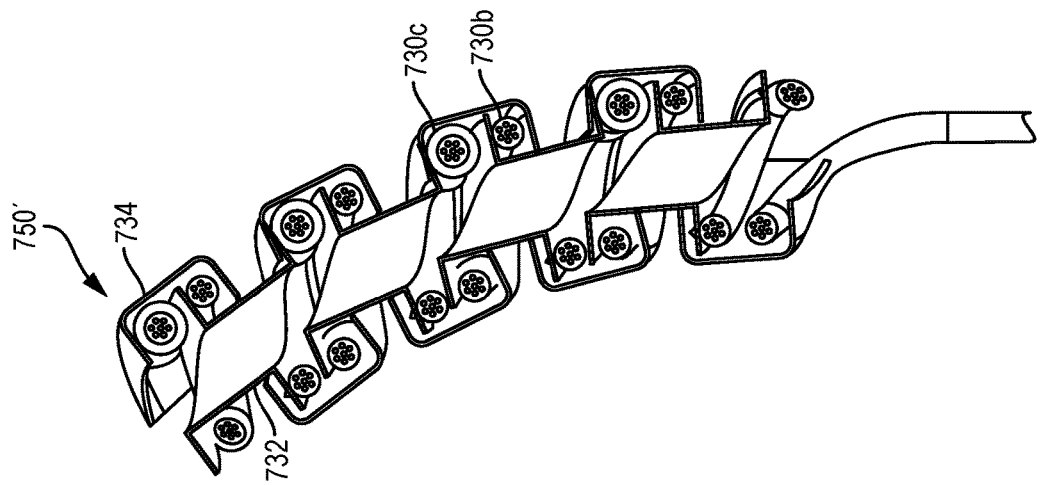
FIGS. 26A and 26B illustrate alternative articulated structures similar to those of FIG. 25, here with two balloon assemblies supported in opposition along the frames.
Figure 26A:
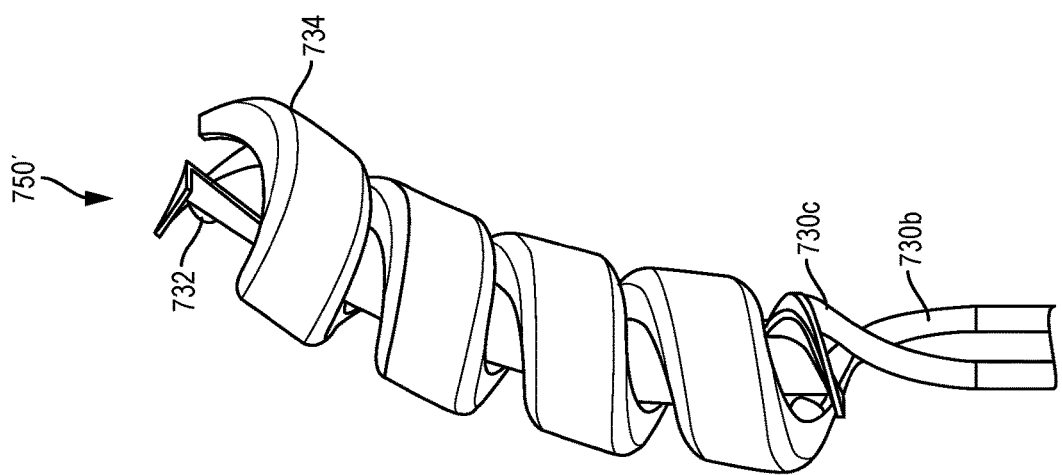

Referring now to FIGS. 26A and 26B, an alternative push/pull structure omits one of the two extension balloon assemblies 730a, 730c, and uses a 1-to-1 extension/contraction balloon opposition arrangement as described above with reference to FIGS. 23A and 23B. Note that this embodiment retains balloon assembly 730c that is radially adjacent to outer frame 734 (so that no balloons are visible even with the sheath removed). Alternative embodiments may retain assembly 730a and forego assembly 730c (so that balloons could be seen through a clear sheath, for example).

Figure 27:
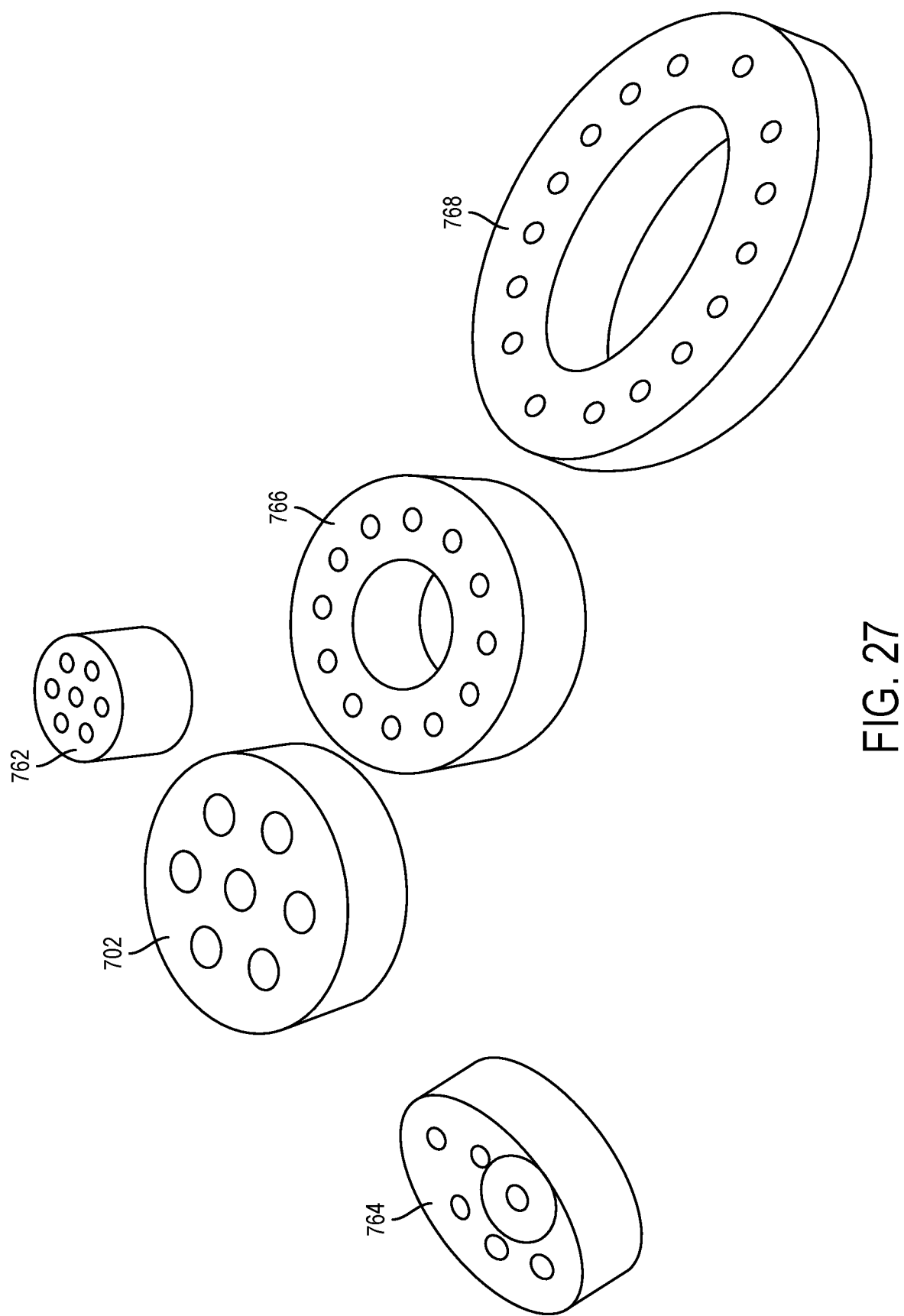
FIG. 27 illustrates alternative multi-lumen conduit or core structures for use in the balloon assemblies of FIGS. 24 and 25, showing a variety of different numbers of channels that can be used with different numbers of articulated segments.

Referring now to FIG. 27, short segments of alternative core structures are shown for comparison. Core shaft 702 has an outer diameter of about 0.028" and 7 lumens, with 6 peripheral lumens having an inner diameter of about 0.004" readily available for formation associated ports and use in transmitting inflation fluid to and from balloons. A central lumen might be used, for example, in monitoring of the vacuum system to verify integrity of the system. Core shaft 702 can be used, for example, in a 14-15 Fr catheter system having two segments that are each capable of providing up to 120 degrees of bending (or alternatively more or less depending on the number of balloons ganged together on each channel), with such a system optionally capable of providing a bend radius sufficient for to fit a 180 degree bend of the catheter within a space of 3 inches or less, ideally within 2½ inches or less, and in some cases within 2 inches or less. Such a system may be beneficial for structural heart therapies, for example, and particularly for mitral valve delivery, positioning, and/or implantation.

Referring still to FIG. 27, other therapies may benefit from smaller catheter profiles, and do not need the bending forces available from a 15 Fr catheter. Electrophysilogy therapies such as AFib ablation from within an atrium of the heart may be good examples of therapies which would benefit from the degrees of freedom that can be provided in small structures using the systems described herein. Scaling the 15 Fr system down for a 7-8 Fr ablation catheter might make use of a directly scaled core 762 having half the overall outer diameter and half the lumen inner diameter of core 702, as the pressure-containing stresses in the material would scale with the lumen diameters. However, there may be cost benefits to maintaining minimum lumen wall thicknesses that are above 0.002", preferably at or above 0.0025", and ideally at or above about 0.003". Toward that end, and to provide 6 contraction or extension lumens for two 3D push/pull segments along a common helical core along with a desirably small bend radius, it may be beneficial to use radially elongate core 764 having a 6 lumens that are all surrounded by at least 0.003" of material. Core 764 has an axial height of half of core 702 and a radial width of that is less than half the balloon diameter of the 14-15 Fr system. There may be benefits to having the radial (elongate) dimension of the cross-section being less than the inflated inner diameter of the balloons mounted thereon, to inhibit trapping of inflation fluid on one axial side of the balloon (away from the inflation port).

Still further advantages may be provided by applying the smaller lumen and wall thickness dimensions of 7 Fr core 762 to a 15 Fr catheter core size, as it results in the 12 inflation lumen core 766. The large 13$^{th}$ lumen of this embodiment may help enhance flexibility of the segments, and can again be used to monitor system integrity using a vacuum system. The 12 lumens may allow, for example, a continuous push/pull structure to have 4 independently controllable 3D shape (4D shape+stiffness) segments. A 16 inflation lumen core 768 combines the smaller lumen and wall thickness with a radially elongate cross-section, allowing 5 independently controllable 3D segments. It should be understood that still further numbers of lumens at smaller profiles are possible using known and relatively low cost multilumen extrusion techniques.

It should be understood that still further alternative embodiments may take advantage of the beneficial components and assemblies described herein. For example, as can be understood from the disclosure above regarding many of the flexible structures of FIGS. 3-12, inflation of a balloon may be resiliently opposed by a helical spring or other biasing structure so that the spring deflates the balloon and urges a flexible body back toward a pre-balloon-inflation state when the inflation fluid is released from the balloon. Rather than relying on 6 dedicated opposed expansion and contraction balloon channels for each segment (providing independent contraction and expansion along each lateral orientation) in the push/pull ring frame and push/pull helical frame embodiments described above, two or more of the channels (from the same segments or from different segments) may be grouped together to act as a common baising structure or fluid spring. As an example, all the contraction balloons along two adjacent segments might open to a single lumen that is inflated to less than full pressure. Modulating pressure to the different sets of extension balloons may still allow the extension balloons to articulate each segment with three independent degrees of freedom, as the grouped contraction balloons could selectively be overpowered by the extension balloons (like the coil springs) or may be allowed to deflate the extension balloons. In some embodiments, rather than relying on partial pressure of extension or contraction balloons, an elastomeric material may be mounted over the core of some or all of the extension or contraction balloons of a segment so as to passively oppose a set of the balloons.

Figure 28:
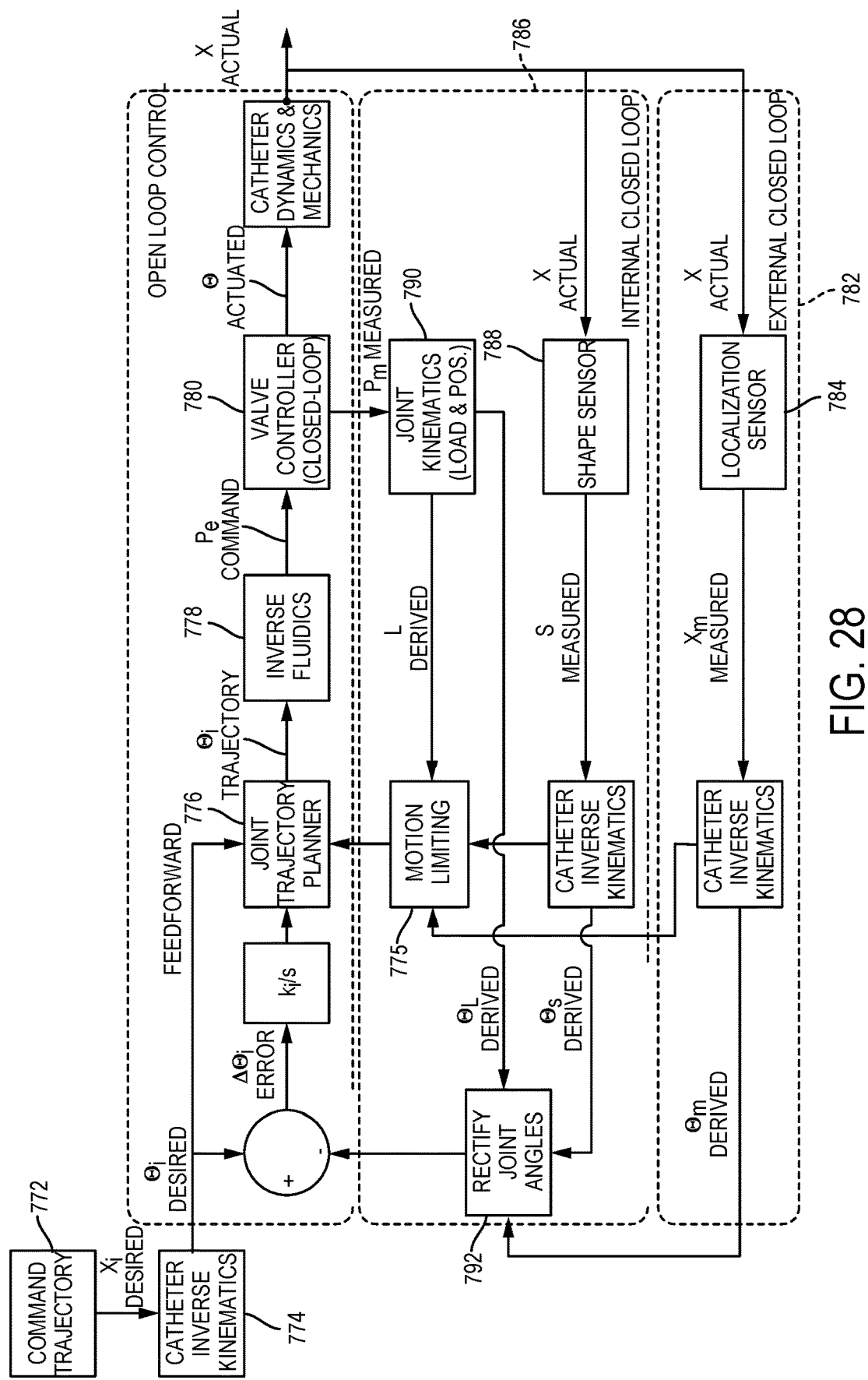
FIG. 28 schematically illustrates control system logic for using the fluid drive systems described herein to articulate catheters and other elongate flexible structures per input provided by a system user.

Referring now to FIG. 28, an articulation controller 770 for directing inflation fluid to and from the actuation balloons of the systems will typically have hardware and/or software configured and programmed to generally seek to cause the articulable structure to assume a new actual position or state $X_{actual}$ in response to a commanded trajectory 772 input by a system user. Many of the articulated flexible structures described herein may be included in robotic systems that can be analyzed and controlled using techniques associated with continuum robots, and the articulated structures will often be under-constrained with more joints then can be directly controlled by the system using standard controller. These excess or redundant degrees of freedom are often managed and made to cooperate using an internal compliance that directs the joints to be at a similar angle relative to the next joint within the segment. These equal joint angles may help lead the system toward a lowest potential energy state for the system. The processor of the system will typically have software modules to determine the next desired position or state of the articulatable structure $X_{iDesired}$, and will apply inverse catheter kinematics 774 to determine the next desired joint state $\Theta_{iDesired}$. A difference between an actual joint state and the next desired joint state is determined to define a joint error, and the desired joint state can be fedforward to a joint trajectory planner 776 along with the joint error to define a joint error trajectory. This joint trajectory can be used in an inverse fluidic calculation 778 to determine command signals that can be fed into a closed-loop valve controller 780 so as to provide an actuated joint state. In some embodiments, closed loop control of the valves may depend on pressure sensing, and may be used to control to specific pressures as determined by valve inverse kinematics. The catheter dynamics and mechanics reaction to the actuated joint state (with the associated environment interactions with the catheter such as tissue forces and the like) result in a new actual position or state $X_{actual}$ of the articulated catheter system.

Feedback on the actual position or state of the articulated system to the controller may be omitted in some embodiments, but other embodiments may benefit from such feedback to provide more precise movements and better correlation (from the system user's perspective) between the command inputs and the actual changes in state. Toward that end, the controller may optionally use one or more closed loop feedback pathways. In some embodiments, a feedback system that is partially or fully external to the articulated structure 782 may sense the actual position or state of the catheter or other articulated structure using a localization sensor 784, such as an electromagnetic navigation system, an ultrasound navigation system, image processing coupled to 3D imaging (such as biplanor fluoroscopy, magnetic resonance imaging, computed tomography, ultrasonography, stereoscopic cameras, or the like; where the imaging modality may optionally also be used to produce images presented to the system user for image guided articulation). In many embodiments, the feedback will be provided using signals obtained from the articulated system itself under an internal closed loop feedback system 786. To obtain a measured shape or state of the articulated structure, a variety of known sensor technologies may be employed as an articulated structure shape sensor 788, including optical fiber shape sensors (such as those using fiber Bragg gratings), electrical shape sensors (such as those which use elastically deformable circuit components), or the like. The measured and/or sensed signals may be processed using inverse kinematics to derive associated measure and/or sensed joint states. Furthermore, balloon array pressure signals will often be available from the pressure sensors of the system, along with information correlating the pressures with the joint or shape state of the articulated system. The history of inflation fluid directed to and exhausted from the articulation balloons may also be used to help determine an estimated inflation fluid quantity present in each balloon (or set of balloons on a common inflation lumen). Where balloons are mounted in opposition or in parallel, the pressure and inflation fluid quantity of these related balloons on separate channels may also be available. Some or all of this pressure information may be processed using a joint kinematics processor 790 to determine a pressure-derived joint position or state (including a derived position of the pressure-articulated joints making up the flexible structure kinematic chain $\Theta_{LDevived}$). The pressure information, preferably along with internal localization information and/or external localization information, may also be used by the joint kinematic processor 790 to derive the loads on the joints, for determining of motion limits 775 as used by the joint trajectory planner 776, and the like. Where more than one is available, the external localization-based feedback joint state, the internal shape-sensor based joint state, and the pressure-derived joint state may be rectified 792 and the rectified (or otherwise any available) joint state compared to the desired joint state to determine the joint error signal.

Figure 29:
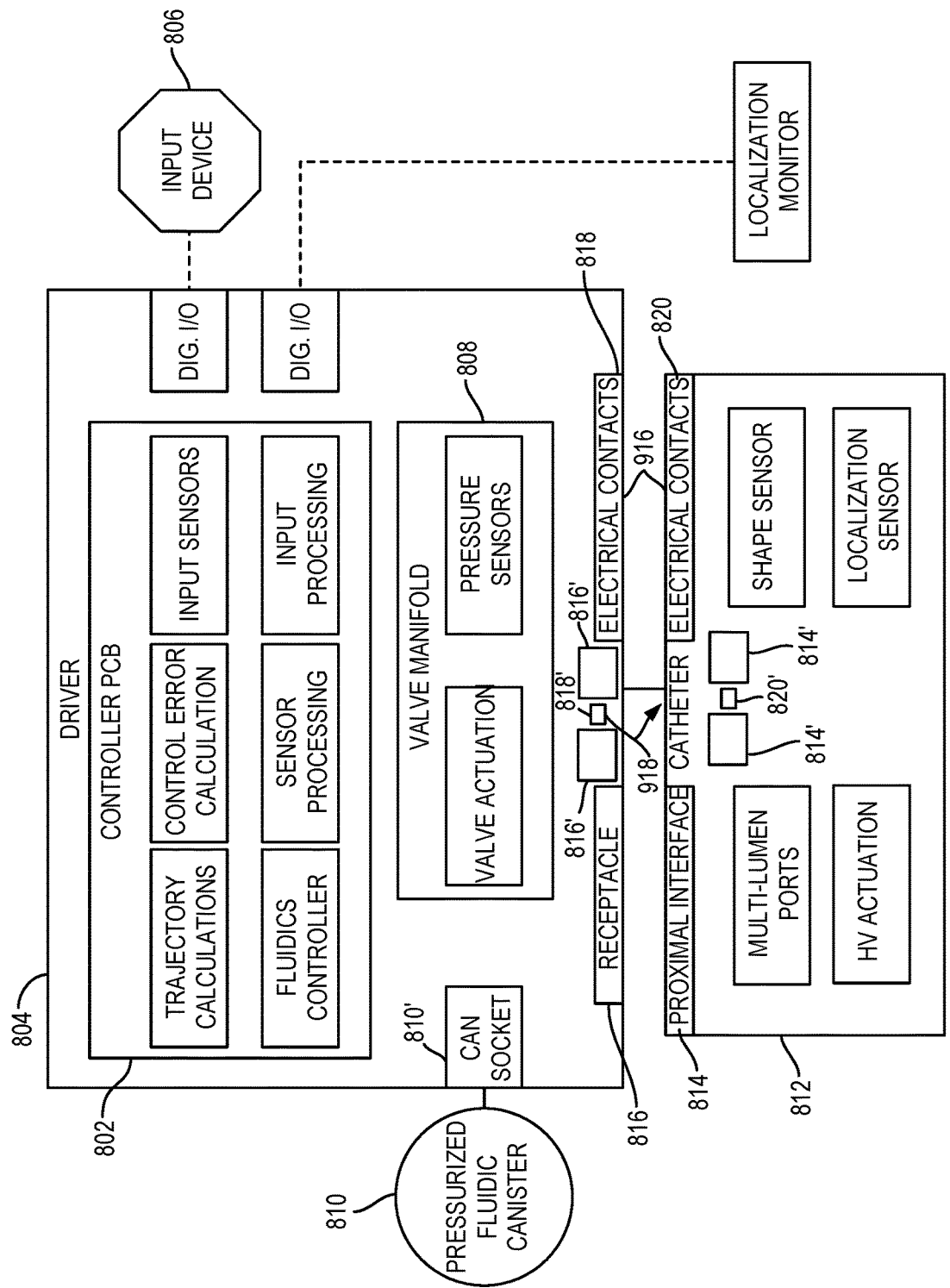
FIG. 29 schematically illustrates a data acquisition and processing system for use within the systems and methods described herein.

Referring now to FIG. 29, an exemplary data processing structure 800 for controlling the shape of a catheter or other articulated elongate flexible bodies described herein can be understood. Much of the data processing occurs on a controller board 802 of reusable driver 804, with the driver optionally comprising a hand-held capital equipment unit. The input device 806 may optionally include a separate workstation with wired or wireless data telemetry (so as to allow, for example, an interventional cardiologist or the like to perform a portion of the procedure while separated from the radiation field of a fluoroscopy system), or input device 806 may be a user interface integrated into the hand-held driver, or both. Preferably, the valve manifold 808 will comprise one of the modular plate manifold structures described herein, and will be contained within the hand-held driver unit 804. Canister 810 may be affixed to the driver (directly or by coupling of the catheter to the driver) using a canister socket or receptacle 810', and will often be included within a hand-held proximal assembly of deployment system that includes the driver, the proximal interface of the catheter, and other proximal components of the catheter (such as the heart valve actuation or deployment device 813, or the like) during use. Similarly, a battery of the system (not shown) may be integrated into the driver 804, may be mounted to the proximal interface of the catheter, or both.

A catheter 812 or other elongate flexible body for use with driver 804 will generally have a proximal interface 814 that mates with a receptacle 816 of the driver. As can be understood with reference to the descriptions above, the mating of the proximal interface with the receptacle will often provide sealed fluid communication between a balloon array of the catheter and the valves of the manifold assembly. Coupling of the proximal interface with the receptacle may also result in coupling of electrical contacts of the driver 818 with electrical contacts of the catheter 820, thereby facilitate access to internal shape sensor data, external localization data (which may employ a powered fiducial on the catheter and an external electromagnetic sensor system, or the like). Articulation state feedback may be provided using electrical interface/receptacle connectors (such as using known electromagnetic internal navigation systems) or optical interface/receptacle connectors 818', 820' (such as using known optical fiber Bragg grating flex sensors). Still further communications between the catheter and the driver may also be facilitated, including transmission of catheter identification data (which may include a catheter type for configuration of the controller, a unique catheter identifier so as to help inhibit undesirable and potentially deleterious re-use of the catheter, and the like). As an alternative to (or in addition to) electrical communication of this data, catheter 812 may have an RFID 814', bar code 814", or other machine-readable tag on or near proximal interface 814, and driver 804 may include a corresponding RFID reader 816', bar code reader 816", or other machine tag reader on or near receptacle 816.

Referring now to FIGS. 30A-30D, an alternative proximal interface 830 of the catheter can be understood, along with how it can be mated to an alternative receptacle 832 of an alternative modular manifold 834. Proximal interface 830 provides sealed communication between axially separated ports of up to three multi-lumen shafts 836, with the ports of the multi-lumen shafts being sealed by axially compressing O-rings 838 or other deformable sealing bodies interleaved between more rigid interface members 840. Threaded compression members 842 maintain axial sealing compression between a proximal-most interface member and a distal-most interface member. Posts 844 of interface members 840 extend laterally and parallel to each other. Each interface member 840 includes a post 844 for each multi-lumen shaft, and the number of interface members included in proximal interface 830 is the same as the number of independently used lumens in each multi-lumen shaft, so that the posts form an array with the total number of posts being equal to the total number of independent multi-lumen channels in the articulated structure. Lumens extend radially from the ports of the multi-lumen shaft, through the posts 844, and to an interface port surrounded by a cap of deformable seal material.

Figure 30A:
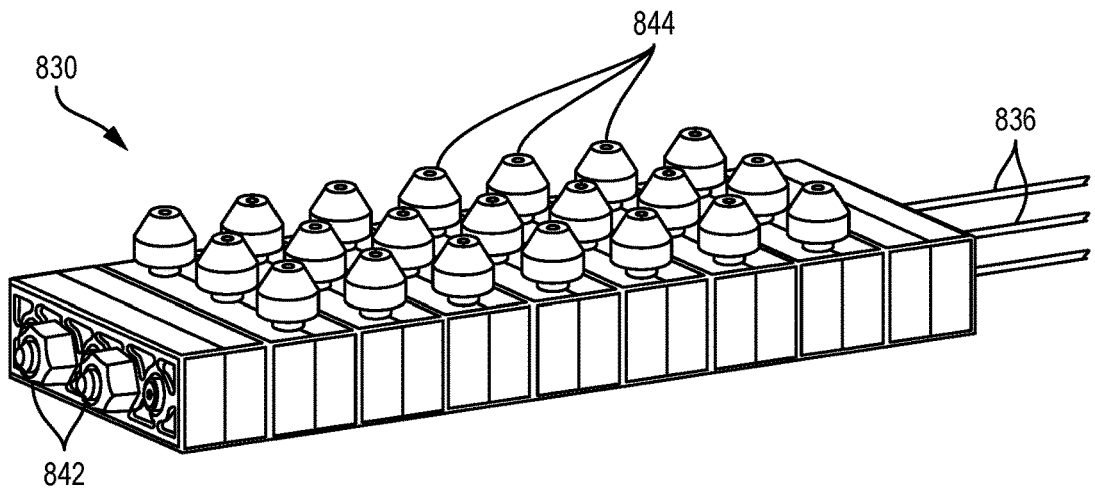
FIGS. 30A-30D illustrate an alternative interface for coupling a modular fluid manifold to a plurality of multi-lumen shafts so as to provide control over articulation of a catheter along a plurality of segments, each having a plurality of degrees of freedom, along with portions of some of the plate modules of the manifold, with the plate modules here having a receptacle member that helps couple the layers of the plates to posts of the interface.
Figure 30B:
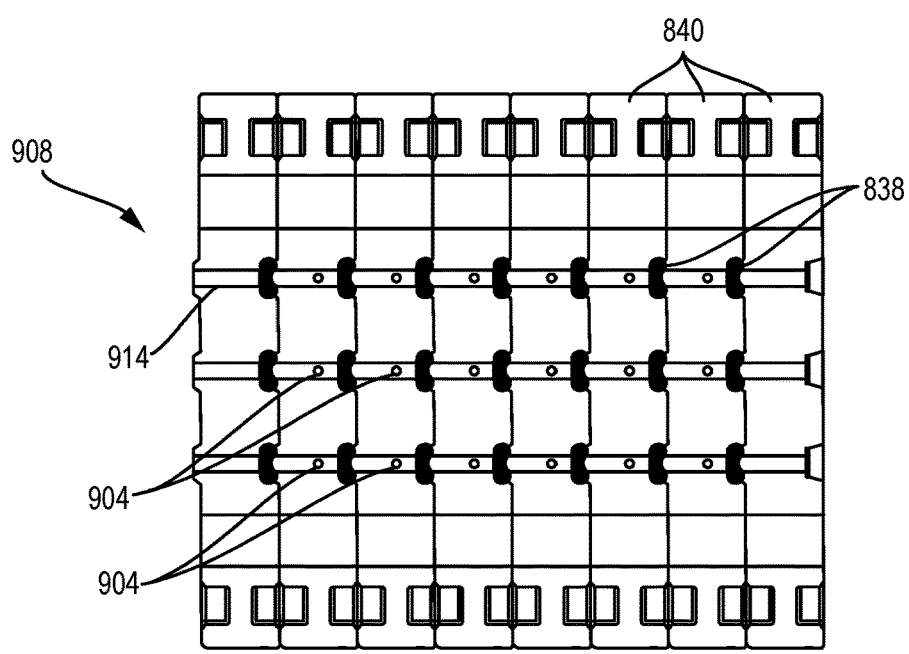
Figure 30C:
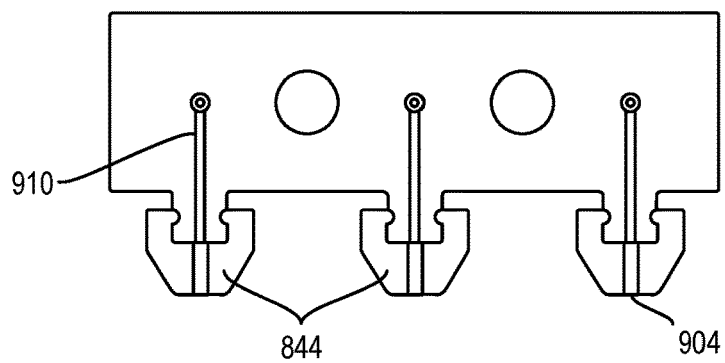
Figure 30D:
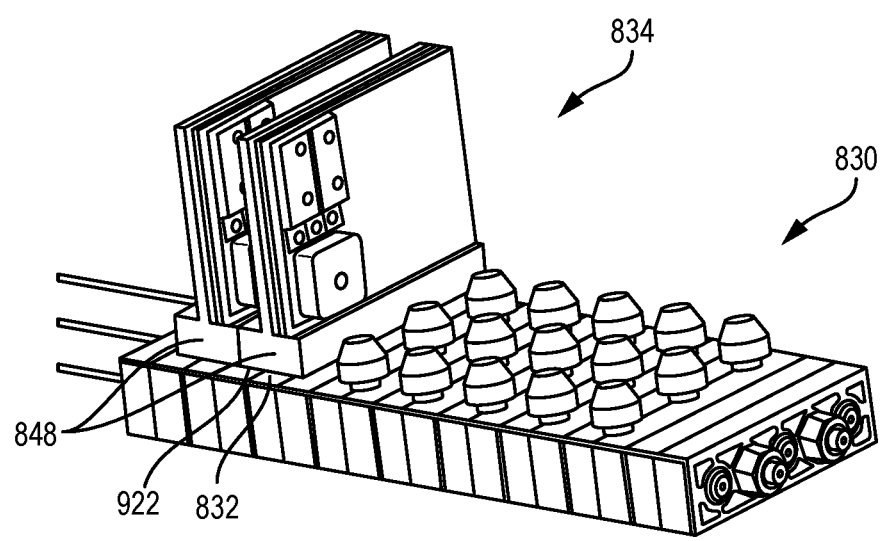

Referring to FIG. 30D, receptacle 832 of manifold assembly 834 has a series of indentations that correspond with posts 844 of proximal interface 830. The indentations have surfaces that correspond to the posts and seal to the deformable caps with the interface ports each in sealed fluid communication with an associated channel of an associated plate module. In this embodiment, the receptacle surfaces of each plate modules is on a receptacle member 848. The receptacle members support plate layers with channels formed between the layers, with MEMS valves and pressure sensors mounted to the plates as described above. Here, however, the plates of adjacent plate modules may not be in direct plate-plate contact, so that the supply and exhaust flows may extend axially through the receptacle members, through the proximal interface, or through another structure of the manifold assembly.

Referring now to FIG. 24D, lumens 902 provide fluid communication with associated ports 904 within associated balloons 906 along the distal articulated segment. Referring to FIG. 18 and FIGS. 30A-30C, associated ports 904 can provide fluid communication with the lumens adjacent the proximal end of the catheter and/or posts 844 of a catheter/manifold interface body. A plurality of regions 908 of the manifold or the catheter/manifold interface body may each have a fluid supply channel 910 that can be coupled to an associated fluid supply 912 of the manifold, with the regions optionally defining a contiguous feature 914. Electrical connectors 916 on or near the receptacle of the manifold and the manifold interface of the catheter body are shown in FIG. 29, as are optical fiber connectors 918. A vacuum source 920 of the manifold is seen in FIG. 18, and the structure of a receptacle having an array of indentations 922 is shown in FIG. 30D. The use of balloons as fluid driven actuators 924 in a chamber 926 can be seen in FIG. 25F.

While the exemplary embodiment have been described in some detail for clarity of understanding and by way of example, a variety of modifications, changes, and adaptations of the structures and methods described herein will be obvious to those of skill in the art. Hence, the scope of the present invention is limited solely by the claims attached hereto.

What is claimed is:

1. An articulation system comprising:
   an articulated structure including:
   an elongate flexible body having a proximal end and a distal end with an axis therebetween,
   a proximal interface adjacent the proximal end of the elongate flexible body having a plurality of ports, the plurality of ports including a first port and a second port,
   a plurality of actuators distal of the plurality of ports and proximal of the distal end and offset eccentrically relative to the axis, the plurality of actuators including a first subset of the plurality of actuators and a second subset of the plurality of actuators, the first subset of the plurality of actuators comprising at least two of the plurality of actuators, the second subset of the plurality of actuators comprising at least two of the plurality of actuators, and a plurality of lumens extending along the elongate flexible body, the plurality of lumens including a first lumen and a second lumen, the first subset of the plurality of actuators being in fluid communication with the first lumen and the first port and aligned axially along a first lateral bending orientation, and the second subset of the plurality of actuators being in fluid communication with the second lumen and the second port and aligned axially along a second lateral bending orientation, the second lateral bending orientation being offset circumferentially relative to the first lateral bending orientation; and a manifold having:

a manifold body with a proximal orientation and a distal orientation with a manifold axis therebetween, the manifold body having a plurality of regions distributed along the manifold axis, each region having a fluid supply channel, and a receptacle traversing the plurality of regions, wherein the receptacle removably receives the proximal interface of the articulated structure with the plurality of ports in sealed fluid communication with the fluid supply channels such that, during use, fluid transmitted from the fluid supply channels actuates the plurality of actuators so as to induce lateral movement of the distal end, with the fluid in the first lumen at a first pressure actuating the first subset of the plurality of actuators to laterally bend the axis of the elongate flexible body along the first lateral bending orientation such that the distal end moves laterally, and with the fluid in the second lumen at a second pressure, independent of the first pressure, to laterally bend the axis of the elongate flexible body along the second lateral bending orientation such that the distal end moves laterally.

2. The articulation system of claim 1, wherein the articulated structure comprises a catheter and the plurality of actuators of the articulated structure include a plurality of balloons, and wherein the fluid transmitted from the fluid supply channels inflates the balloons so that the balloons induce bending of the axis of the elongate flexible body.

3. The articulation system of claim 1, wherein the proximal interface of the articulated structure comprises a contiguous structure and the receptacle comprises a contiguous feature such that alignment of the proximal interface with the receptacle registers the fluid supply channels with the plurality of ports.

4. The articulation system of claim 3, further comprising a quick-disconnect fitting manually movable between a first configuration and second configuration, the quick-disconnect fitting maintaining sealed fluid communication between the plurality of ports and the fluid supply channels in the first configuration, the quick-disconnect fitting allowing removal and replacement of the proximal portion in the second configuration.

5. The articulation system of claim 1, wherein the proximal interface of the articulated structure comprises one or more of a radio frequency identification (RFID) label, an electrical connector, or an optical fiber connector; and wherein the receptacle comprises an RFID reader, an electrical connector, or an optical fiber connector.

6. The articulation system of claim 1, further comprising a pressurized canister containing inflation fluid, the inflation fluid comprising an inflation liquid in the canister, the inflation liquid vaporizing to an inflation gas in use so that the inflation fluid comprises the inflation gas within the plurality of actuators, the pressurized canister matable with a canister receptacle of the manifold so as to transmit the inflation fluid toward the fluid supply channels.

7. The articulation system of claim 6, wherein the inflation liquid comprises nitrous oxide, and wherein less than 10 oz. of the inflation fluid is contained within the canister.

8. The articulation system of claim 1, further comprising a fluid shutoff valve disposed upstream of the fluid channels, a vacuum source, and a vacuum sensing system;
the plurality of actuators being disposed within a chamber and the vacuum source being coupleable thereto, the vacuum sensing system coupling the chamber to the shutoff valve so as to inhibit transmission of inflation fluid to the plurality of actuators of the articulated structure in response to deterioration of vacuum within the chamber.

9. The articulation system of claim 1, wherein one of the receptacle or the proximal interface comprises an array of posts, and wherein the other is sealingly matable with the array of posts to provide sealed fluid communication between the plurality of ports and the fluid supply channels.

10. The articulation system of claim 9, wherein the articulated body has an integer number A of multi-lumen shafts extending proximally from the plurality of actuators, integer number A being greater than 1, each multi-lumen shaft having an integer number B of lumens, the lumens having associated ports and associated actuators, integer number B being greater than 1, and wherein the array of posts comprises an integer number A×integer number B posts.

11. A catheter articulation system comprising:
an articulated catheter including an elongate flexible body having a proximal end and a distal end with an axis therebetween, a proximal interface adjacent the proximal end having a plurality of ports including a first port and a second port, a plurality of fluid-driven actuators distal of the plurality of ports and proximal of the distal end, and a plurality of lumens including a first lumen and a second lumen extending along the elongate flexible body providing fluid communication between the plurality of ports and the plurality of actuators;
a manifold having a manifold body with a receptacle extending across a plurality of regions including a first region having a first fluid supply channel and a second region having a second fluid supply channel, wherein the receptacle removably receives the proximal interface of the articulated catheter with the first port and the second port in sealed fluid communication with the first fluid supply channel and the second fluid supply channel, respectively, such that, during use, fluid transmitted from the first fluid supply channel induces a first pressure in the first lumen so as to bend the axis and move the distal end of the elongate flexible body laterally along a first lateral bending orientation, and fluid transmitted from the second fluid supply channel induces a second pressure in the second lumen so as to bend the axis and move the distal end of the elongate flexible body along a second lateral bending orientation circumferentially offset from the first lateral bending orientation, the second pressure being independent of the first pressure.

12. The system of claim 11, further comprising a disposable pressurized canister containing inflation fluid, the canister having a frangible seal to inhibit reuse, the inflation fluid comprising an inflation liquid in the canister, the inflation liquid vaporizing to an inflation gas in use, the pressurized canister releasably matable with a canister receptacle of the manifold so as to transmit the inflation fluid to pressurize the first fluid supply channel and the second fluid supply channel, wherein the canister is configured so that less than 10 oz. of the inflation fluid is contained within the canister.

13. The system of claim 11, further comprising a fluid shutoff valve disposed upstream of the first fluid supply channel and the second fluid supply channel, a vacuum source, and a vacuum sensing system;
the plurality of actuators being disposed within a chamber and the vacuum source being coupleable thereto, the vacuum sensing system coupling the chamber to the shutoff valve so as to inhibit transmission of the inflation fluid to the plurality of actuators of the catheter in response to deterioration of vacuum within the chamber.

14. The system of claim 11, wherein the manifold includes an inflation fluid source and a plurality of inflation valves disposed between the fluid source and the fluid supply channels so as to selectively transmit fluid from the source to the fluid supply channels for selectively pressurizing the subset of the actuators.

15. The system of claim 14, wherein the manifold includes at least 8 valves, the plurality of actuators configured for driving the distal end of the catheter with at least 4 degrees of freedom.

16. The system of claim 15, wherein the plurality of actuators comprise balloons.

17. An articulation system comprising:
an articulated structure including:
an elongate flexible body having a proximal end and a distal end with an axis therebetween,
a proximal interface adjacent the proximal end of the elongate flexible body having a first port and a second port,
a first plurality of actuators and a second plurality of actuators, the first plurality of actuators and the second plurality of actuators offset eccentrically relative to the axis, the first plurality of actuators aligned along a first lateral bending orientation, the second plurality of actuators aligned along a second lateral bending orientation offset circumferentially from the first lateral bending orientation, and
a first lumen and a second lumen extending along the elongate flexible body, the first lumen providing fluid communication between the first port and the first plurality of actuators, the second lumen providing fluid communication between the second port and the second plurality of actuators; and
a manifold body having a receptacle configured to removably receive the proximal interface of the articulated structure with the first port and the second port in sealed fluid communication with a first fluid supply channel and a second fluid supply channel, respectively, such that, during use, fluid transmitted from the first fluid supply channel to the first lumen at a first pressure actuates the first plurality of actuators to laterally move the distal end of the elongate flexible body in alignment with the first lateral bending orientation, and fluid transmitted from the second fluid supply channel to the second lumen at a second pressure, independent of the first pressure, laterally moves the distal end of the elongate flexible body in alignment with the second lateral bending orientation.

* * * * *

UNITED STATES PATENT AND TRADEMARK OFFICE
CERTIFICATE OF CORRECTION

PATENT NO.         : 10,758,714 B2
APPLICATION NO.    : 15/080979
DATED              : September 1, 2020
INVENTOR(S)        : Keith Phillip Laby and Mark D. Barrish Page 1 of 1

It is certified that error appears in the above-identified patent and that said Letters Patent is hereby corrected as shown below:

In the Claims

Column 66, Line 36, Claim 10: please delete "an interger number Axinteger" and insert --integer number A X integer--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*